US012678175B2

(12) United States Patent
Cushen et al.

(10) Patent No.: US 12,678,175 B2
(45) Date of Patent: Jul. 14, 2026

(54) SURGICAL INSTRUMENT SYSTEM AND IRRIGATION SLEEVE

(71) Applicant: Stryker European Operations Holdings LLC, Portage, MI (US)

(72) Inventors: Patrick Eoin Cushen, Cork (IE); Fintan Tynan, Kilkenny (IE); James G. Walen, Portage, MI (US)

(73) Assignee: Stryker European Operations Holdings LLC, Portage, MI (US)

( * ) Notice: Subject to any disclaimer, the term of this patent is extended or adjusted under 35 U.S.C. 154(b) by 122 days.

(21) Appl. No.: 18/887,659

(22) Filed: Sep. 17, 2024

(65) Prior Publication Data

US 2025/0009363 A1      Jan. 9, 2025

Related U.S. Application Data

(63) Continuation of application No. 17/865,885, filed on Jul. 15, 2022, now Pat. No. 12,121,242, which is a (Continued)

(51) Int. Cl.
*A61B 17/16*          (2006.01)
*B29C 63/00*          (2006.01)
(Continued)

(52) U.S. Cl.
CPC ...... *A61B 17/1633* (2013.01); *A61B 17/1644* (2013.01); *A61B 17/1671* (2013.01);
(Continued)

(58) Field of Classification Search
CPC ..................... A61B 17/1633; A61B 17/1644
See application file for complete search history.

(56) References Cited

U.S. PATENT DOCUMENTS 1,555,003  A      9/1925  Greenberg et al.
2,112,056  A      3/1938  Wappler
(Continued)

FOREIGN PATENT DOCUMENTS

CN          101627894 A      1/2010
DE      202005018372 U1      1/2006
(Continued)

OTHER PUBLICATIONS

Aesculap Inc., "Elan 4 Brochure", https://www.aesculapUSa.com/content/dam/aesculap-US/US/website/aesculap-inc/healthcareprofessionals/or-soultions/pdfs/DOC1372-Rev-C-ELAN-4-Brochure.pdf.bb-.63883499/DOC1372-Rev-C-ELAN-4-Brochure.pdf, 2019, 28 pages.

(Continued)

*Primary Examiner* — Christian A Sevilla
(74) *Attorney, Agent, or Firm* — Howard & Howard Attorneys PLLC

(57) ABSTRACT

A surgical instrument system including an endoscope having an elongated housing extending between a proximal instrument end and a distal instrument end. The surgical instrument system may further include an irrigation sleeve having a sleeve body extending between a proximal sleeve end and a distal sleeve end. The irrigation sleeve may further have a first lumen and a second lumen spaced out of fluid communication with the first lumen, the first lumen formed in the sleeve body for receiving at least a portion of the elongated housing of the endoscope with the distal instrument end arranged adjacent to the distal sleeve end. The second lumen may be formed in the sleeve body and extend between a lumen inlet adapted for fluid communication with an irrigation source and a lumen outlet arranged to direct irrigation fluid toward the distal instrument end.

20 Claims, 40 Drawing Sheets

Related U.S. Application Data continuation of application No. 16/633,202, filed as application No. PCT/US2018/016840 on Feb. 5, 2018, now Pat. No. 11,413,051.

(60) Provisional application No. 62/536,733, filed on Jul. 25, 2017.

(51) Int. Cl.
*B29C 63/18* (2006.01)
*A61B 17/00* (2006.01)
*B29L 31/00* (2006.01)

(52) U.S. Cl.
CPC .......... *B29C 63/0069* (2013.01); *B29C 63/18* (2013.01); *A61B 2017/00526* (2013.01); *A61B 2017/00973* (2013.01); *A61B 17/1626* (2013.01); *A61B 17/1628* (2013.01); *A61B 2017/1651* (2013.01); *A61B 2017/1653* (2013.01); *A61B 2217/007* (2013.01); *B29L 2031/7546* (2013.01)

(56) References Cited

U.S. PATENT DOCUMENTS

| | | | |
|---|---|---|---|
| 2,429,356 A * | 10/1947 | Hicks | A61C 3/02 |
| | | | 433/116 |
| 3,844,272 A | 10/1974 | Banko | |
| 3,937,222 A * | 2/1976 | Banko | A61F 9/00763 |
| | | | 606/107 |
| 4,014,342 A | 3/1977 | Staub et al. | |
| 4,099,528 A * | 7/1978 | Sorenson | A61M 25/0612 |
| | | | 604/44 |
| 4,167,943 A | 9/1979 | Banko | |
| 4,167,944 A | 9/1979 | Banko | |
| 4,176,791 A | 12/1979 | Cattaneo et al. | |
| 4,316,465 A | 2/1982 | Dotson, Jr. | |
| 4,368,734 A | 1/1983 | Banko | |
| 4,369,768 A | 1/1983 | Vukovic | |
| 4,517,977 A | 5/1985 | Frost | |
| RE32,158 E | 5/1986 | Vukovic | |
| 4,596,564 A | 6/1986 | Spetzler et al. | |
| 4,634,420 A | 1/1987 | Spinosa et al. | |
| 4,646,722 A | 3/1987 | Silverstein et al. | |
| 4,674,500 A | 6/1987 | DeSatnick | |
| 4,802,852 A | 2/1989 | Shea | |
| 4,832,685 A | 5/1989 | Haines | |
| 4,850,342 A | 7/1989 | Hashiguchi et al. | |
| 4,941,872 A | 7/1990 | Felix et al. | |
| 4,986,827 A | 1/1991 | Akkas et al. | |
| 5,019,036 A | 5/1991 | Stahl | |
| 5,152,744 A | 10/1992 | Krause et al. | |
| 5,249,745 A | 10/1993 | Bertolotti | |
| 5,269,785 A | 12/1993 | Bonutti | |
| 5,282,821 A | 2/1994 | Donahue | |
| 5,285,795 A | 2/1994 | Ryan et al. | |
| 5,320,635 A | 6/1994 | Smith | |
| 5,322,505 A | 6/1994 | Krause et al. | |
| 5,342,377 A | 8/1994 | Lazerson | |
| 5,417,654 A | 5/1995 | Kelman | |
| 5,421,829 A | 6/1995 | Olichney et al. | |
| 5,437,630 A | 8/1995 | Daniel et al. | |
| 5,492,527 A | 2/1996 | Glowa et al. | |
| 5,510,070 A | 4/1996 | Krause et al. | |
| 5,540,706 A | 7/1996 | Aust et al. | |
| 5,554,100 A | 9/1996 | Leiner et al. | |
| 5,569,254 A | 10/1996 | Carlson et al. | |
| 5,575,756 A | 11/1996 | Karasawa et al. | |
| 5,620,447 A | 4/1997 | Smith et al. | |
| 5,624,393 A | 4/1997 | Diamond | |
| 5,681,262 A | 10/1997 | Isse | |
| 5,685,821 A | 11/1997 | Pike | |
| 5,685,838 A | 11/1997 | Peters et al. | |
| 5,685,851 A | 11/1997 | Murphy et al. | |
| 5,707,350 A | 1/1998 | Krause et al. | |
| 5,709,698 A * | 1/1998 | Adams | A61B 17/32002 |
| | | | 606/167 |
| 5,759,185 A | 6/1998 | Grinberg | |
| 5,782,795 A | 7/1998 | Bays | |
| 5,792,167 A | 8/1998 | Kablik et al. | |
| 5,823,940 A | 10/1998 | Newman | |
| 5,833,692 A | 11/1998 | Cesarini et al. | |
| 5,910,152 A | 6/1999 | Bays | |
| 5,913,867 A | 6/1999 | Dion | |
| 5,916,231 A | 6/1999 | Bays | |
| 5,947,990 A | 9/1999 | Smith | |
| 5,957,945 A | 9/1999 | Bays | |
| 5,989,183 A | 11/1999 | Reisdorf et al. | |
| 6,007,530 A | 12/1999 | Dornhofer et al. | |
| 6,010,477 A | 1/2000 | Bays | |
| 6,030,356 A | 2/2000 | Carlson et al. | |
| 6,042,593 A | 3/2000 | Storz et al. | |
| 6,068,641 A | 5/2000 | Varsseveld | |
| 6,110,103 A | 8/2000 | Donofrio | |
| 6,126,592 A | 10/2000 | Proch et al. | |
| 6,132,448 A | 10/2000 | Perez et al. | |
| 6,183,433 B1 | 2/2001 | Bays | |
| 6,196,967 B1 | 3/2001 | Lim et al. | |
| 6,214,009 B1 | 4/2001 | Toriumi et al. | |
| 6,221,088 B1 | 4/2001 | Bays | |
| 6,238,400 B1 | 5/2001 | Bays | |
| 6,282,442 B1 | 8/2001 | DeStefano et al. | |
| 6,312,438 B1 | 11/2001 | Adams | |
| 6,391,016 B2 | 5/2002 | Bays | |
| 6,419,654 B1 | 7/2002 | Kadan | |
| 6,428,503 B1 | 8/2002 | Kierce | |
| 6,428,539 B1 | 8/2002 | Baxter et al. | |
| 6,447,446 B1 | 9/2002 | Smith et al. | |
| 6,464,711 B1 | 10/2002 | Emans et al. | |
| 6,503,263 B2 | 1/2003 | Adams | |
| 6,620,180 B1 | 9/2003 | Bays et al. | |
| 6,638,289 B1 | 10/2003 | Johnson et al. | |
| 6,652,547 B2 | 11/2003 | Rabiner et al. | |
| 6,656,195 B2 | 12/2003 | Peters et al. | |
| 6,663,628 B2 | 12/2003 | Peters | |
| 6,669,695 B2 | 12/2003 | Luigi | |
| 6,669,710 B2 | 12/2003 | Moutafis et al. | |
| 6,712,757 B2 | 3/2004 | Becker et al. | |
| 6,979,332 B2 | 12/2005 | Adams | |
| 7,077,845 B2 | 7/2006 | Hacker et al. | |
| 7,150,713 B2 | 12/2006 | Shener et al. | |
| 7,247,161 B2 | 7/2007 | Johnston et al. | |
| 7,338,495 B2 | 3/2008 | Adams | |
| 7,413,542 B2 | 8/2008 | Kucklick et al. | |
| 7,445,596 B2 | 11/2008 | Kucklick et al. | |
| 7,488,322 B2 | 2/2009 | Brunnett et al. | |
| 7,500,947 B2 | 3/2009 | Kucklick et al. | |
| 7,674,263 B2 | 3/2010 | Ryan | |
| 7,699,846 B2 | 4/2010 | Ryan | |
| 7,766,819 B2 | 8/2010 | Matsumoto | |
| 7,771,384 B2 | 8/2010 | Ravo | |
| 7,785,337 B2 | 8/2010 | Adams et al. | |
| 7,803,170 B2 | 9/2010 | Mitusina | |
| 7,811,228 B2 | 10/2010 | Adams | |
| 7,854,736 B2 | 12/2010 | Ryan | |
| 7,879,037 B2 | 2/2011 | Brunnett et al. | |
| 7,918,849 B2 | 4/2011 | Bleich et al. | |
| 7,927,361 B2 | 4/2011 | Oliver et al. | |
| 7,998,061 B2 | 8/2011 | Kucklick et al. | |
| 8,012,083 B2 | 9/2011 | Kucklick et al. | |
| 8,016,846 B2 | 9/2011 | McFarlin et al. | |
| 8,029,438 B2 | 10/2011 | Hagihara et al. | |
| 8,061,359 B2 | 11/2011 | Emanuel | |
| 8,062,214 B2 | 11/2011 | Shener et al. | |
| 8,118,731 B2 | 2/2012 | Kucklick et al. | |
| 8,142,464 B2 | 3/2012 | Mitusina | |
| 8,162,966 B2 | 4/2012 | Connor et al. | |
| 8,167,790 B2 | 5/2012 | Kucklick et al. | |
| 8,172,846 B2 | 5/2012 | Brunnett et al. | |
| 8,192,435 B2 | 6/2012 | Bleich et al. | |
| 8,202,288 B2 | 6/2012 | Adams et al. | |
| 8,206,349 B2 | 6/2012 | Slenker et al. | |
| 8,262,683 B2 | 9/2012 | McFarlin et al. | |

(56) References Cited

U.S. PATENT DOCUMENTS

| 8,273,097 | B2 | 9/2012 | Malla et al. |
| 8,393,328 | B2 | 3/2013 | Angel et al. |
| 8,409,109 | B2 | 4/2013 | Tiesma et al. |
| 8,409,235 | B2 | 4/2013 | Rubin |
| 8,419,624 | B2 | 4/2013 | James et al. |
| 8,419,626 | B2 | 4/2013 | Shener-Irmakoglu et al. |
| 8,465,513 | B2 | 6/2013 | McFarlin et al. |
| 8,529,498 | B2 | 9/2013 | Moutafis et al. |
| 8,568,415 | B2 | 10/2013 | Brunnett et al. |
| 8,579,902 | B2 | 11/2013 | Bleich et al. |
| 8,608,766 | B2 | 12/2013 | Malla et al. |
| 8,623,266 | B2 | 1/2014 | Adams |
| 8,672,921 | B2 | 3/2014 | Efinger et al. |
| 8,721,669 | B2 | 5/2014 | Oliver et al. |
| 8,740,773 | B2 | 6/2014 | Kucklick et al. |
| 8,758,227 | B2 | 6/2014 | Kucklick et al. |
| 8,758,378 | B2 | 6/2014 | McFarlin et al. |
| 8,790,301 | B2 | 7/2014 | Slenker et al. |
| 8,814,626 | B2 | 8/2014 | Smith |
| 8,814,780 | B2 | 8/2014 | Kucklick et al. |
| 8,906,053 | B2 | 12/2014 | Oliver et al. |
| 8,915,842 | B2 | 12/2014 | Weisenburgh et al. |
| 9,028,398 | B2 | 5/2015 | Kumar et al. |
| 9,050,036 | B2 | 6/2015 | Poll et al. |
| 9,050,037 | B2 | 6/2015 | Poll et al. |
| 9,078,562 | B2 | 7/2015 | Poll et al. |
| 9,125,550 | B2 | 9/2015 | Shener-Irmakoglu et al. |
| 9,155,454 | B2 | 10/2015 | Sahney et al. |
| 9,186,157 | B2 | 11/2015 | Brunnett et al. |
| 9,211,373 | B2 | 12/2015 | Dexter et al. |
| 9,226,650 | B2 | 1/2016 | Emanuel |
| 9,226,765 | B2 | 1/2016 | Emanuel |
| 9,332,894 | B2 | 5/2016 | Cheng et al. |
| 9,345,386 | B1 | 5/2016 | Cheng |
| 9,375,207 | B2 | 6/2016 | Kucklick et al. |
| 9,498,108 | B1 | 11/2016 | Lombardi |
| 9,585,547 | B2 | 3/2017 | Cheng et al. |
| 9,700,378 | B2 | 7/2017 | Mowlai-Ashtiani |
| 9,839,739 | B2 | 12/2017 | Qian |
| 10,028,644 | B2 | 7/2018 | Konstorum et al. |
| 11,413,051 | B2 | 8/2022 | Cushen et al. |
| 2001/0000041 | A1 | 3/2001 | Selmon et al. |
| 2006/0041186 | A1 | 2/2006 | Vancaillie |
| 2008/0242935 | A1 | 10/2008 | Inoue |
| 2008/0249483 | A1 | 10/2008 | Slenker et al. |
| 2009/0234193 | A1 | 9/2009 | Weisenburgh, II et al. |
| 2009/0270796 | A1 | 10/2009 | Perry et al. |
| 2009/0270894 | A1 | 10/2009 | Rubin et al. |
| 2010/0280491 | A1 | 11/2010 | Tanghoej |
| 2010/0286616 | A1* | 11/2010 | Baroud ............. A61B 17/3472 |
| | | | 604/164.11 |
| 2011/0009699 | A1 | 1/2011 | Slenker et al. |

| 2011/0270081 | A1 | 11/2011 | Burg et al. |
| 2013/0079751 | A1 | 3/2013 | Dexter et al. |
| 2013/0217970 | A1 | 8/2013 | Weisenburgh, II et al. |
| 2014/0107688 | A1 | 4/2014 | Malla et al. |
| 2014/0276832 | A1 | 9/2014 | Hibri et al. |
| 2014/0318582 | A1 | 10/2014 | Mowlai-Ashtiani |
| 2015/0045678 | A1 | 2/2015 | Ohzawa et al. |
| 2015/0087906 | A1 | 3/2015 | Kucklick et al. |
| 2015/0087907 | A1 | 3/2015 | Konstorum et al. |
| 2015/0087911 | A1 | 3/2015 | Konstorum et al. |
| 2016/0354243 | A1 | 12/2016 | Chandrakant et al. |
| 2017/0189040 | A1 | 7/2017 | Anand et al. |
| 2021/0153878 | A1 | 5/2021 | Cushen et al. |
| 2022/0346809 | A1 | 11/2022 | Cushen et al. |

FOREIGN PATENT DOCUMENTS

| EP | 791336 | A1 * | 8/1997 |
| JP | H10513379 | A | 12/1998 |
| JP | 2003520078 | A | 7/2003 |
| JP | 2007522837 | A | 8/2007 |
| WO | 2005072402 | A2 | 8/2005 |
| WO | 2011031448 | A2 | 3/2011 |
| WO | 2016054140 | A1 | 4/2016 |

OTHER PUBLICATIONS

Conmed, "Hall Powered Instruments System Product Catalog", http://www.wemed1.com/downloads/dl/file/id/4807/product/1451/specs_for_hall_power_catalog.pdf, 2014, 118 pages.
Desoutter Medical, "Accessories for Surgical Powered Instruments Brochure", http://www.de-soutter.com/gallery/Catalogues/Accessories%20162-EN.pdf, 2016, 20 pages.
English language abstract and machine-assisted English translation for DE 202 005 018 372 U1 extracted from espacenet.com database on Dec. 2, 2021, 10 pages.
English language abstract for JP 2003-520078 A extracted from espacenet.com database on Dec. 2, 2021, 2 pages.
International Search Report for Application No. PCT/US2018/016840 dated Mar. 23, 2018, 3 pages.
Medtronic ENT, "Otologic Drills and Burs Brochure", http://www.tkbbv.org.tr/tkbbvData/Document/23122014174645-TUR-UCU-KATALOGU.pdf, 2012, 24 pages.
Stryker Neuro Spine ENT, "Signature Elite Attachments Brochure", https://neurosurgical.stryker.com/wp-content/uploads/2016/09/Signature-Portfolio-Elite-attachments-brochure.pdf, 2016, 2 pages.
English language abstract for JPH 10-513379 A extracted from espacenet.com database on Jun. 20, 2025, 1 page.
English language abstract for JP 2007-522837 A extracted from espacenet.com database on Jun. 20, 2025, 1 page.

* cited by examiner

SURGICAL INSTRUMENT SYSTEM AND IRRIGATION SLEEVE

CROSS-REFERENCE TO RELATED APPLICATIONS

The subject patent application is a continuation of U.S. application Ser. No. 17/865,885, filed Jul. 15, 2022, which is a continuation of U.S. application Ser. No. 16/633,202, filed Jan. 23, 2020, which issued as U.S. Pat. No. 11,413,051 on Aug. 16, 2022, which was the National Stage of International Patent Application No PCT/US2018/016840, filed Feb. 5, 2018, which claims priority to, and all the benefits of, U.S. Provisional Patent Application No. 62/536,733, filed Jul. 25, 2017, the entire contents of which are incorporated by reference herein.

TECHNICAL FIELD

The disclosure set forth herein relates, generally, to surgical systems and, more specifically, to irrigation sleeves for use with surgical systems. The disclosure also relates to methods of manufacturing irrigation sleeves for use with surgical systems.

BACKGROUND

Conventional medical procedures routinely involve the use of surgical tools to assist medical professionals in approaching, viewing, manipulating, or otherwise effecting treatment at localized surgical sites. In certain applications, such as those which involve the use of high-speed drills, rotating burs, open-window shavers, and the like necessarily results in the accumulation of heat and debris at the surgical site. Here, surgical systems employ irrigation systems which generally comprise an irrigation source connected to an irrigator via a flexible line. The irrigator typically employs one or more clips or fasteners to facilitate attachment to the surgical tool for concurrent movement. Irrigation systems also typically employ a user input to control the flow of fluid out of the irrigator fluid towards the surgical site during use.

Conventional irrigation systems have a tendency to produce a dripping effect out of the irrigator during use, which causes fluid to accumulate on rotating cutting instruments, resulting in splashing at the surgical site. Here, there is a tendency for fluid to splash onto endoscopes used during the surgical procedure. It will be appreciated that splashing of the endoscope can obstruct the medical professional's view of the surgical site.

In order to mitigate the splashing effect described above, certain surgical systems may comprise additional valves or user input controls positioned close to the irrigator. However, these surgical systems tend to be expensive, difficult to clean and/or sterilize, and add complexity to preparing for and carrying out the medical or surgical procedure. Other surgical systems attempt to mitigate the splashing effect by positioning the irrigator further away from the surgical tool, for example by moving the irrigator away from the rotational axis of the cutting accessory. However, this arrangement adds handling bulk to the surgical tool and necessitates exposing a larger surgical site, which is undesirable and may be incompatible with certain medical and surgical procedures, such as those used in connection with minimally invasive surgery.

There remains a need in the art for a surgical irrigation system which overcomes the disadvantages mentioned above, which can be used in connection with different types of surgical tools used in a broad array of medical and surgical procedures, and which strikes a substantial balance between usability, functionality, and manufacturing cost while, at the same time, affording consistent and reliable irrigation in use.

SUMMARY

In one aspect, a surgical instrument system usable with an irrigation source. The surgical instrument system may comprise an endoscope having an elongated housing extending between a proximal instrument end and a distal instrument end. The surgical instrument system may further comprise an irrigation sleeve. The irrigation sleeve may comprise a sleeve body, a first lumen, and a second lumen. The sleeve body may extend between a proximal sleeve end and a distal sleeve end. The first lumen may be formed in the sleeve body for receiving at least a portion of the elongated housing of the endoscope with the distal instrument end arranged adjacent to the distal sleeve end. The second lumen may be formed in the sleeve body and extending between a lumen inlet adapted for fluid communication with the irrigation source and a lumen outlet arranged to direct irrigation fluid toward the distal instrument end. The second lumen may be spaced out of fluid communication with the first lumen.

In another aspect, an irrigation sleeve for use with a surgical system. The surgical system may comprise an irrigation source and a surgical instrument having a housing extending to a distal end. The irrigation sleeve may comprise a sleeve body extending between a proximal sleeve end and a distal sleeve end. The irrigation sleeve may further comprise a first lumen and a second lumen. The first lumen may be formed in the sleeve body for receiving at least a portion of the surgical instrument. The second lumen may be formed in the sleeve body and spaced from the first lumen. The second lumen may comprise a proximal lumen region and a distal lumen region, the proximal lumen region extending from a lumen inlet adapted for fluid communication with the irrigation source to a lumen transition, and the distal lumen region extending from the lumen transition to a lumen outlet. The proximal lumen region may have a larger cross-sectional area than the distal lumen region taken at the lumen transition. The distal lumen region of the second lumen may be spaced out of fluid communication with the first lumen.

Other features and advantages of the present disclosure will be readily appreciated, as the same becomes better understood, after reading the subsequent description taken in conjunction with the accompanying drawings.

DETAILED DESCRIPTION

Figure 1:
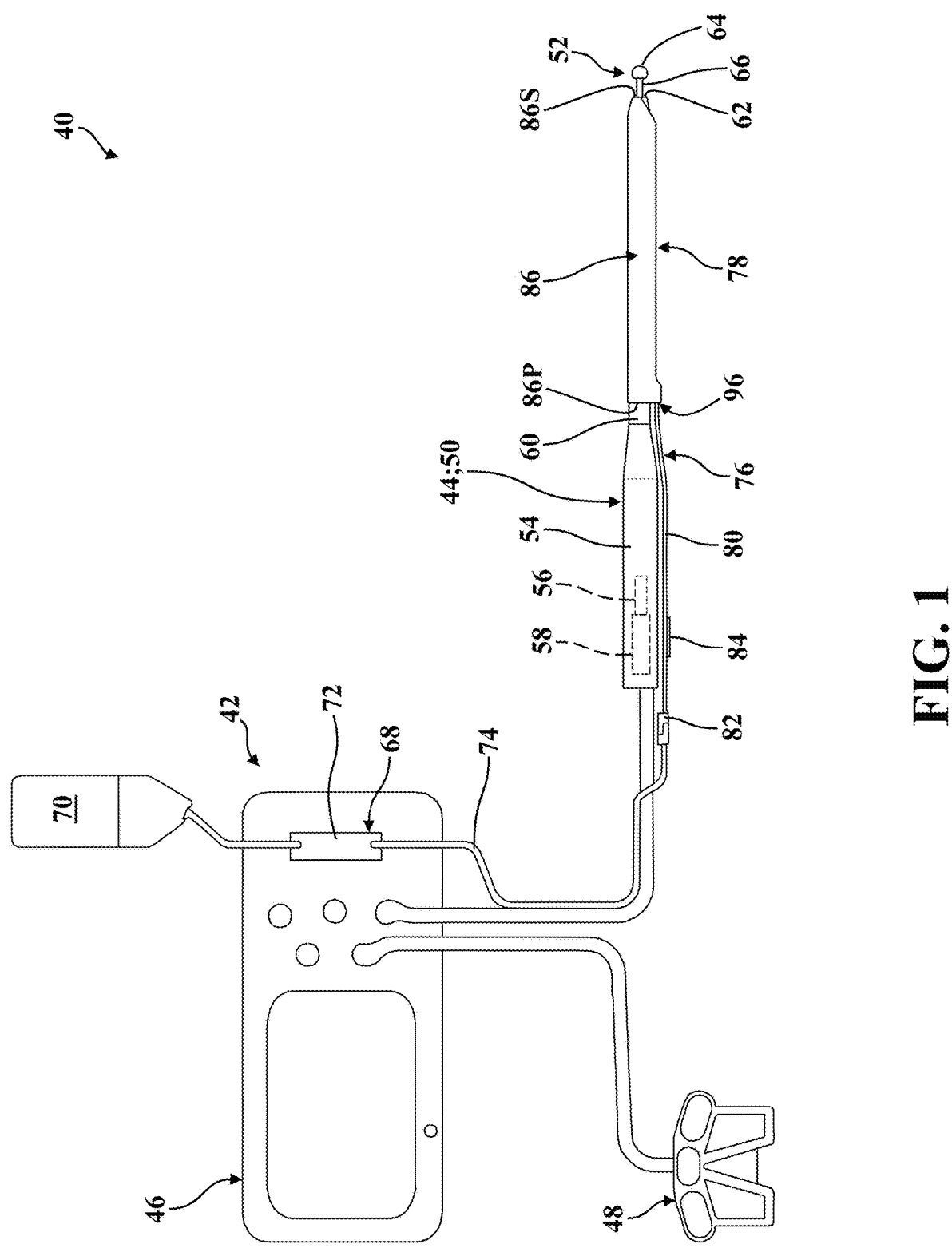
FIG. 1 is a schematic view of a surgical system comprising a console, an irrigation source, and a rotary instrument with a cutting accessory, shown with an irrigation sleeve assembly according to one embodiment coupled to the rotary instrument and disposed in fluid communication with the irrigation source.

With reference now to the drawings, wherein like numerals indicate like parts throughout the several views, a surgical system is shown at 40 in FIG. 1. The surgical system 40 generally comprises an irrigation system 42 and a surgical tool 44, each of which will be described in greater detail below. A console 46 is employed to control both the irrigation system 42 and the surgical tool 44 via a footswitch 48. However, as will be appreciated from the subsequent description below, both the irrigation system 42 and the surgical tool 44 could be configured and/or controlled in a number of different ways. By way of non-limiting example, the surgical tool 44 and the irrigation system 42 could be controlled independently, such as by discrete consoles or input devices.

Figure 2:
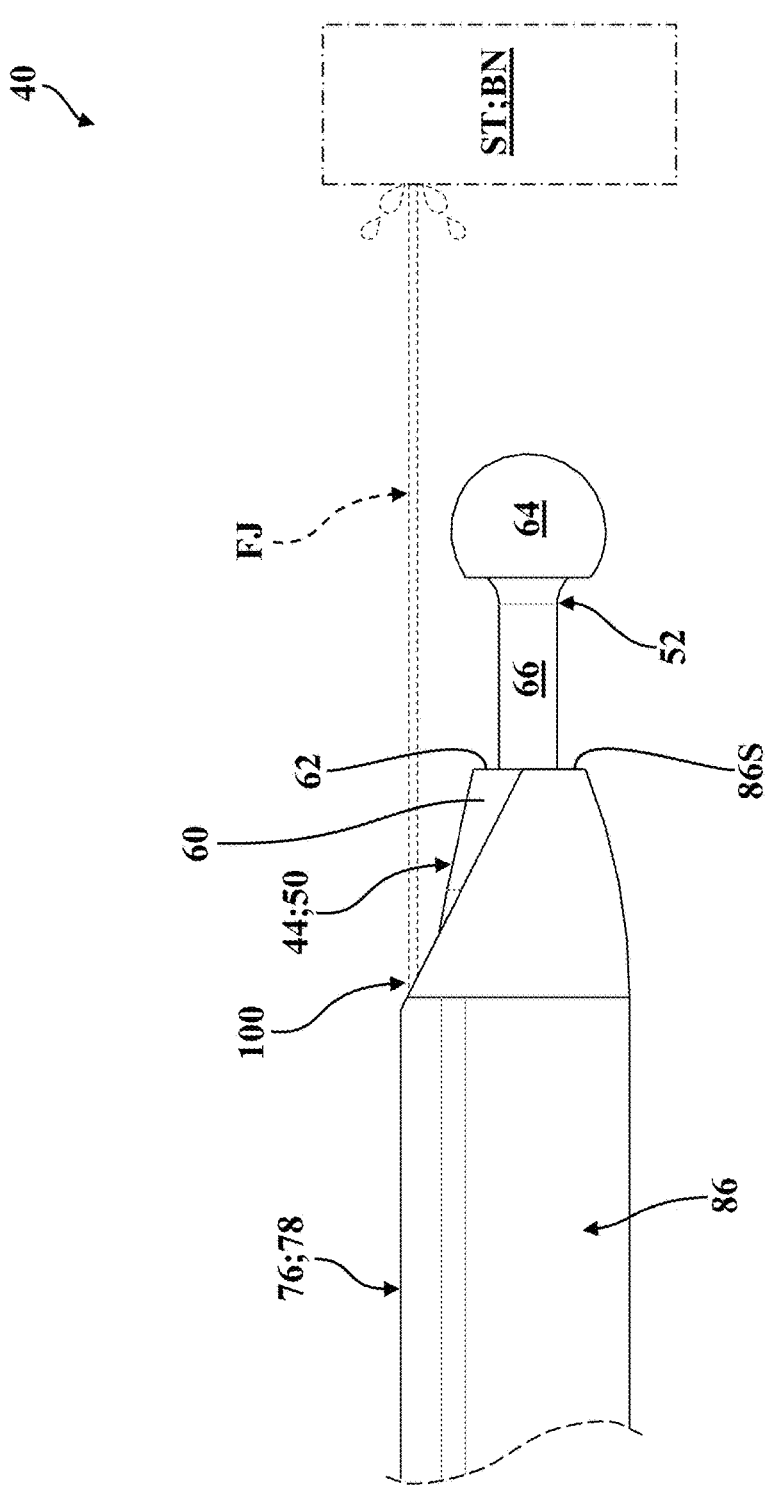
FIG. 2 is partial, right-side view of the rotary instrument, the cutting accessory, and the irrigation sleeve assembly of FIG. 1, shown with a jet of fluid projecting, from an irrigation outlet of the irrigation sleeve assembly, next to and beyond the cutting accessory towards an illustrative surgical site.
Figure 3:
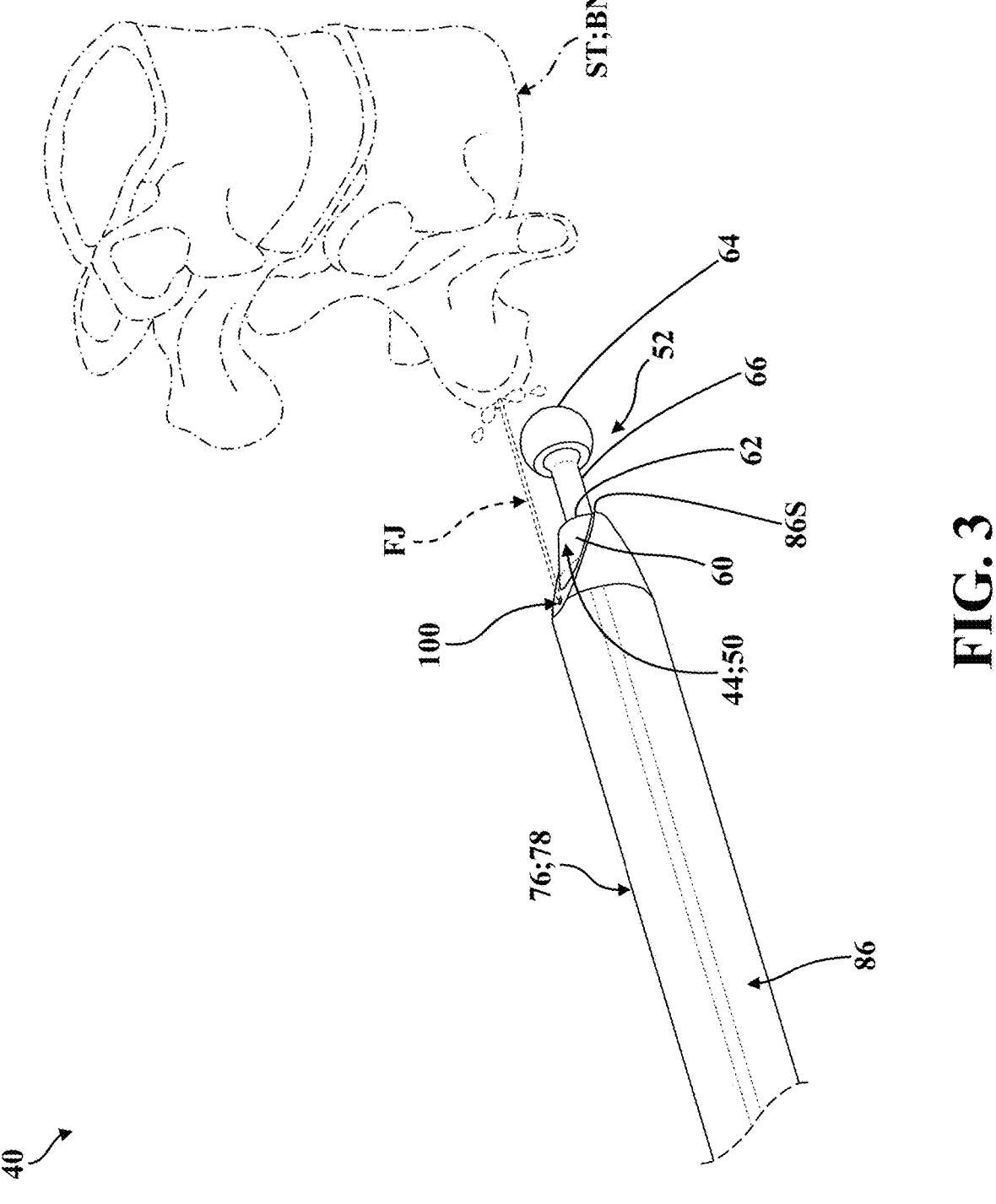
FIG. 3 is a partial perspective view of the rotary instrument, the cutting accessory, and the irrigation sleeve assembly of FIG. 2, shown with the jet of fluid projecting next to and beyond the cutting accessory towards an illustrative surgical site comprising vertebral bone.
Figure 4:
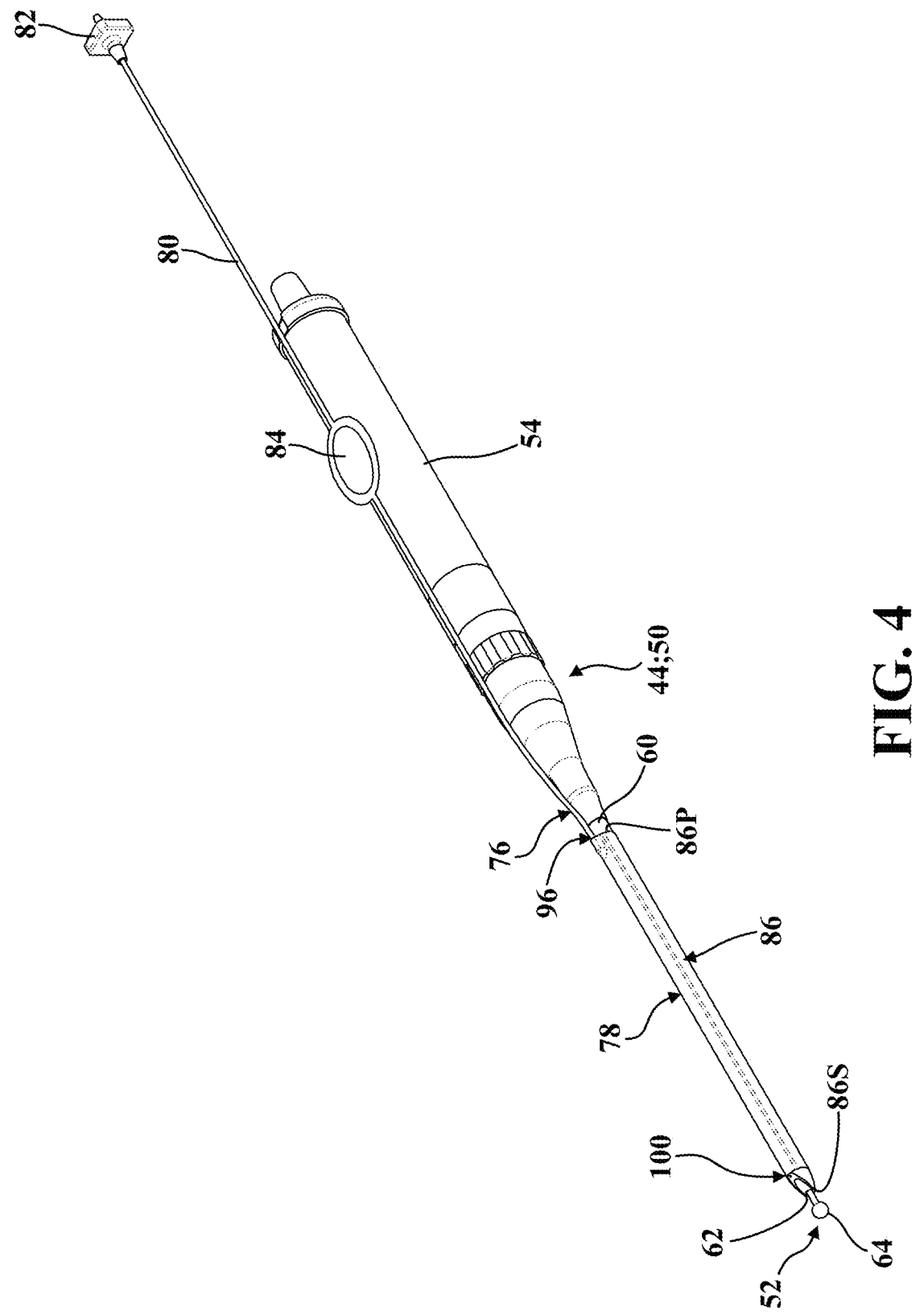
FIG. 4 is a perspective view of the rotary instrument, the cutting accessory, and the irrigation sleeve assembly of FIGS. 1-3.
Figure 5:
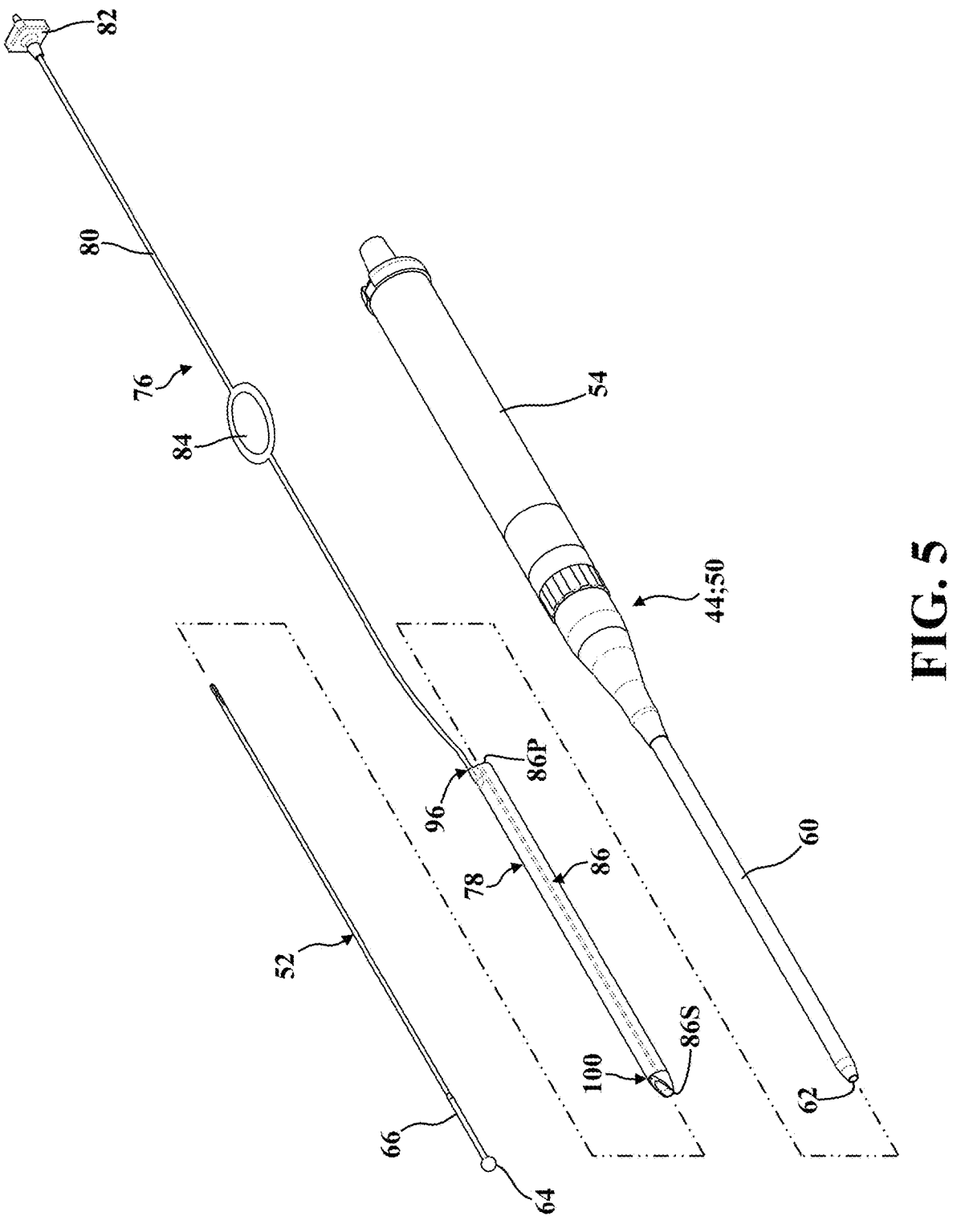
FIG. 5 is an exploded perspective view of the rotary instrument, the cutting accessory, and the irrigation sleeve assembly of FIG. 4.

Referring now to FIGS. 1-3, in the representative embodiment illustrated herein, the surgical tool 44 is realized as a rotary instrument 50 which drives a cutting accessory, generally indicated at 52. Here, the cutting accessory 52 is adapted to assist a medical professional in approaching and/or manipulating a surgical site ST by effecting the removal of tissue, bone, and the like. To this end, the cutting accessory 52 is depicted throughout the drawings as a bur. However, those having ordinary skill in the art will appreciate that the cutting accessory 52 could be of a number of different types or configurations. By way of non-limiting example, the cutting accessory 52 could be a drill, a shaver, and the like. Moreover, while the representative surgical tool 44 illustrated herein is realized as a rotary instrument 50, those having ordinary skill in the art will appreciate that the surgical tool 44 could be configured in a number of different ways, including but not limited to an endoscope, a reciprocating tool, and the like, from any number of components controlled in any suitable way sufficient to cooperate with the irrigation system 42 as described in greater detail below.

The rotary instrument 50 generally comprises a housing 54 which supports a coupling 56 and a motor 58 therein (depicted schematically in FIG. 1). The motor 58 generates rotational torque which is translated to the coupling 56 which, in turn, is configured to releasably secure the cutting accessory 52 for concurrent rotation with the motor 58. The rotary instrument 50 further comprises a tube, generally indicated at 60, which extends from the housing 54 to a distal tube end 62. The cutting accessory 52, in turn, comprises a head 64 and a shank 66 extending from the head 64. The shank 66 is adapted to be rotatably supported by the tube 60 of the rotary instrument 50, and is secured axially to the rotary instrument 50 via the coupling 56 (not shown in detail). In the exemplary cutting accessory 52 illustrated herein, the head 64 is realized as a bur, but could be of any suitable type or configuration, as noted above.

In the exemplary rotary instrument 50 illustrated herein, the motor 58 is powered via a wired electrical connection with the console 46 and is controlled via the footswitch 48, which is similarly disposed in electrical communication with the console 46. However, those having ordinary skill in the art will appreciate that the rotary instrument 50 could be configured in a number of different ways, with or without a wired motor 58 controlled by a console 46. By way of non-limiting example, the rotary instrument 50 could be powered pneumatically or could be driven by a motor disposed within the console. Similarly, while the footswitch 48 is employed to effect control of the motor 58 via the console 46, other types of user inputs are contemplated. For example, buttons, switches, and the like could be operatively attached to the housing 54 of the rotary instrument 50 to control rotation of the motor 58, or the console 46 could control rotation of the motor 58 without the footswitch 48.

Those having ordinary skill in the art will appreciate that the use of high-speed drills, rotating burs, open-window shavers, and the like necessarily results in the accumulation of debris at the surgical site ST. Here, the surgical system 40 employs the irrigation system 42 to directs fluid towards the surgical site ST to loosen, float, and/or displace debris for subsequent removal (for example, by suction). The irrigation system 42 may also be used to ensure proper operation of surgical tools 44 during procedures by clearing debris from endoscopes, cooling cutting accessories, preventing the accumulation of debris on cutting accessories, and the like.

The irrigation system 42 of the surgical system 40 is configured to direct fluid from an irrigation source 68 towards the surgical site ST. In FIG. 1, the irrigation source 68 comprises a fluid reservoir 70 realized as a bag of saline solution disposed in fluid communication with a motor-driven pump cassette 72 which, in turn, is disposed in fluid communication with a line 74. Here, the pump cassette 72 is operatively attached to the console 46, is controlled via the footswitch 48, and is configured to direct fluid from the fluid reservoir 70 to the line 74. The line 74, in turn, is adapted to releasably attach to an irrigation sleeve assembly, generally indicated at 76, to direct fluid towards the surgical site ST as described in greater detail below in connection with FIGS. 2-3.

It will be appreciated that conventional irrigation systems 42 can be used in connection with a number of different types of surgical tools 44. As such, irrigation systems 42 are generally adjustable in terms of fluid flowrate or pump speed. Thus, depending on the type of medical or surgical procedure, the specific configuration of the surgical tool 44 being used, and/or the preferences of the medical professional, the irrigation system 42 may be configured to supply fluid at a particular, adjustable flowrate (for example, by selecting a certain pump speed). Those having ordinary skill in the art will appreciate that irrigation systems 42 can be configured and/or controlled in a number of different ways. Specifically, the irrigation system 42 could be controlled via a discrete console, as noted above. Moreover, while the pump cassette 72 is advantageously driven with an electric motor via the console 46, other arrangements of irrigation sources 68 are contemplated herein. For example, displacement of fluid from the fluid reservoir 70 towards the irrigation sleeve assembly 76 could be achieved via a manually-actuated pump. Furthermore, it will be appreciated that the irrigation system 42 and/or the surgical tool 44 could incorporate, or otherwise cooperate with, a suction system or other systems, tools, and the like utilized in connection with medical and/or surgical procedures.

Referring now to FIGS. 1 and 4-6, the illustrated irrigation sleeve assembly 76 comprises an irrigation sleeve 78, a feeder tube 80, a connector 82, and an adhesive member 84. As will be appreciated from the subsequent description below, the irrigation sleeve assembly 76 can accommodate different types of surgical tools 44, irrigation systems 42, surgical systems 40, and the like, and may be configured as a disposable, single-use product may can be configured as a cleanable and/or serializable, multi-use product.

As is described in greater detail below, the irrigation sleeve 78 is adapted to be coupled to the tube 60 of the rotary instrument 50 and, in certain configurations, is configured to project a fluid jet FJ next to and beyond the head 64 of the cutting accessory 52 towards the surgical site ST (see FIGS. 2-3). To this end, the feeder tube 80 is interposed in fluid communication between the connector 82 and the irrigation sleeve 78, and the connector 82 is adapted for attachment to the line 74 of the irrigation system 42 described above. Thus, fluid displaced by the pump cassette 72 flows from the irrigation source 68 through the line 74 and the feeder tube 80 to the irrigation sleeve 78 which, in turn, projects the fluid jet FJ, as noted above and as is described in greater detail below.

It will be appreciated that the feeder tube 80 can be coupled to the irrigation sleeve 78 and to the connector 82 in a number of different ways, such as via ultraviolet bonding, gluing, a barbed connection, and the like. While the connector 82 is adapted for releasable attachment to the line 74 described above, other configurations are contemplated. For example, the feeder tube 80 could be of various lengths and may be adapted for attachment directly to the irrigation source 68, directly to the pump cassette 72, to a valve interface, and the like. The adhesive member 84 is coupled to the feeder tube 80 and is configured to secure the feeder tube 80 to the housing 54 of the rotary instrument 50 during use (see FIG. 5; adhesion not shown in detail). Furthermore, it will be appreciated that irrigation sleeve assembly 76 may employ irrigation sleeves 78 of different styles, lengths, configurations, and the like consistent with the present disclosure. By way of non-limiting example, the embodiment of the irrigation sleeve 78 illustrated in FIGS. 1-14 has a generally "tapered" distal profile, and the embodiment of the irrigation sleeve 78 illustrated in FIGS. 21-28 has a generally "flat" distal profile. The specific differences between the illustrated embodiments will be described in greater detail below.

Referring now to FIGS. 1-14 and 21-28, the illustrated embodiments of the irrigation sleeve 78 are adapted to be coupled to the tube 60 of the rotary instrument 50, as noted above (see FIGS. 4-6). To this end, in one configuration, the irrigation sleeve 78 comprises a sleeve body 86 which extends between a proximal sleeve end 86P and a distal sleeve end 86S. A first lumen 88 is formed in the sleeve body 86 for receiving at least a portion of the tube 60 of the rotary instrument 50, such that the head 64 of the cutting accessory 52 is arranged adjacent to the distal sleeve end 86S (sec FIGS. 2, 3, and 6). As will be appreciated from the subsequent description below, the irrigation sleeve 78 may be first positioned onto the tube 60 of the rotary instrument 50, and then the cutting accessory 52 may be subsequently secured to the rotary instrument 50. A second lumen 90, spaced from the first lumen 88, is also formed in the sleeve body 86 and is isolated from the first lumen 88 such that no fluid communication occurs between the first lumen 88 and the second lumen 90. The illustrated embodiments of the irrigation sleeve 78 employ a unitary, one-piece sleeve body 86 in which with the first lumen 88 and the second lumen 90 are formed.

Figure 6:
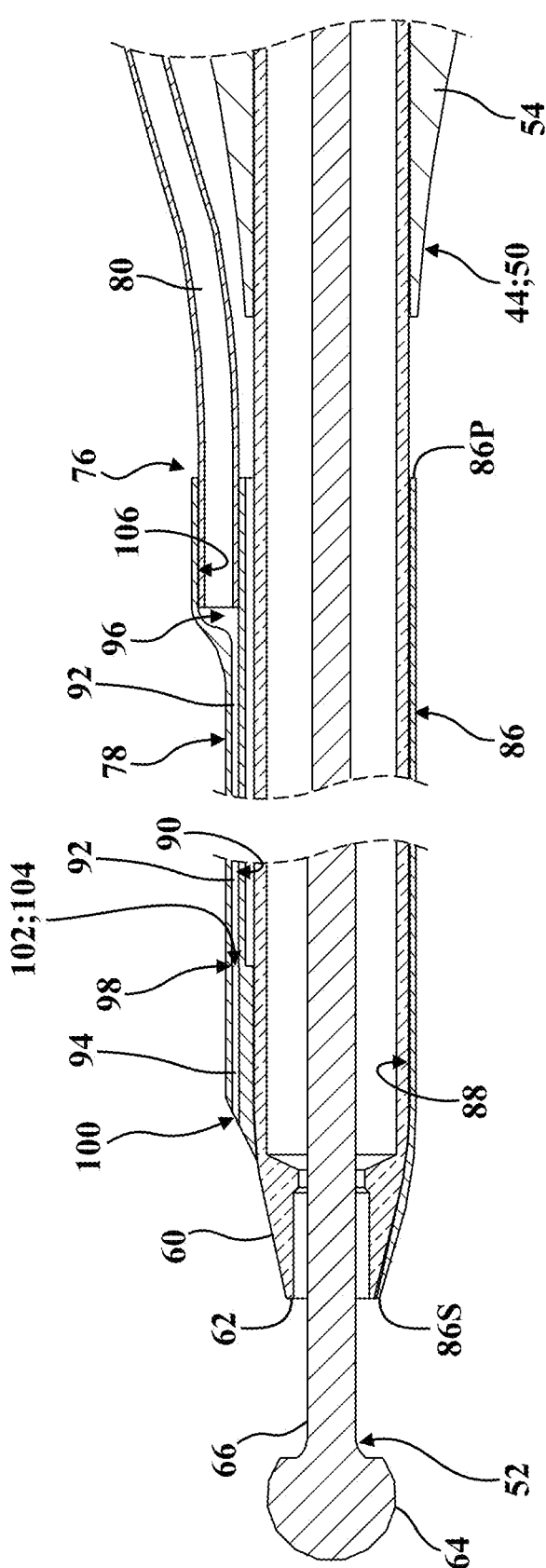
FIG. 6 is a partial, broken sectional view taken longitudinally through the rotary instrument, the cutting accessory, and the irrigation sleeve assembly as illustrated in FIG. 4.
Figure 7:
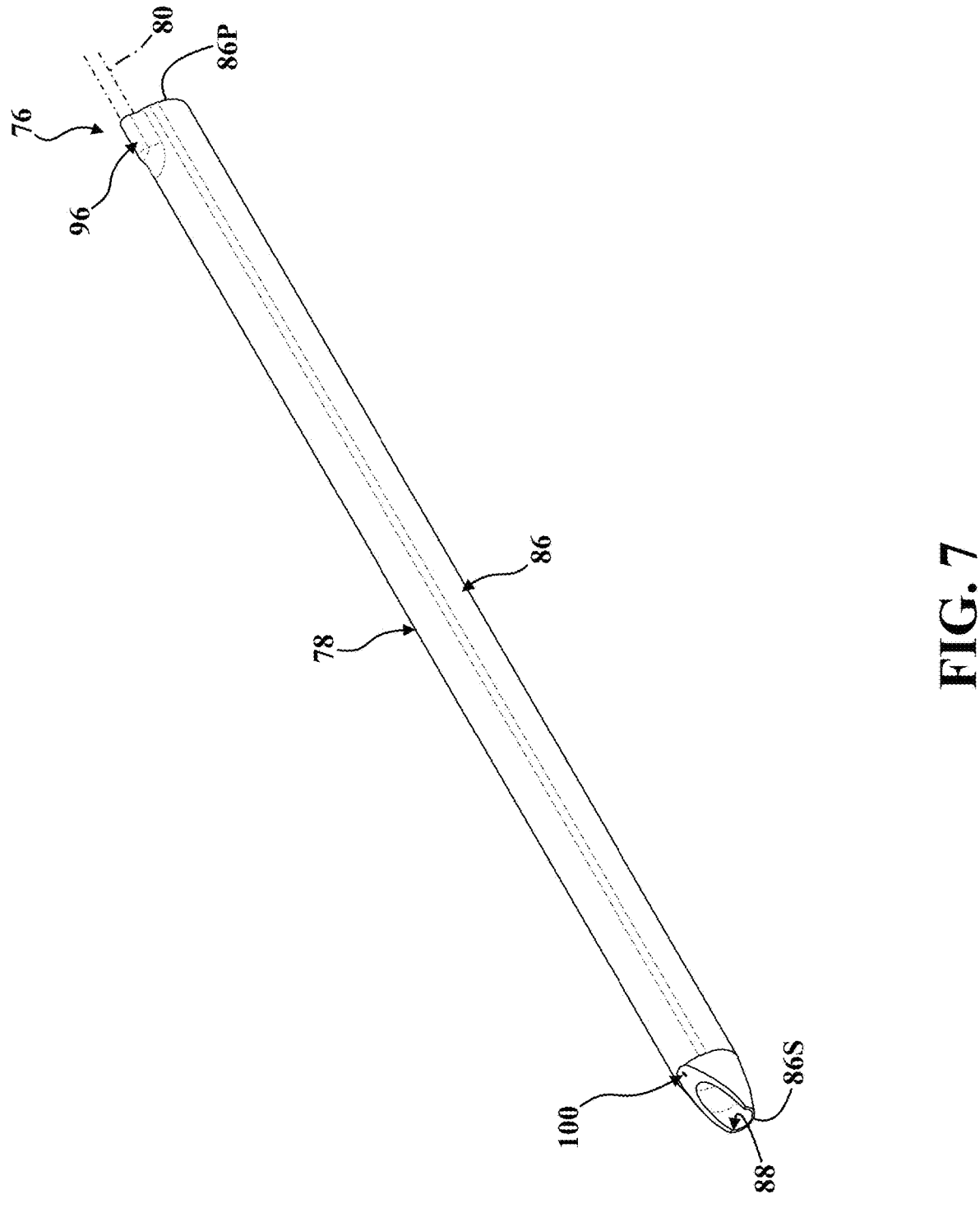
FIG. 7 is a perspective view of one embodiment of an irrigation sleeve of the irrigation sleeve assembly depicted in FIGS. 1-6.
Figure 8:
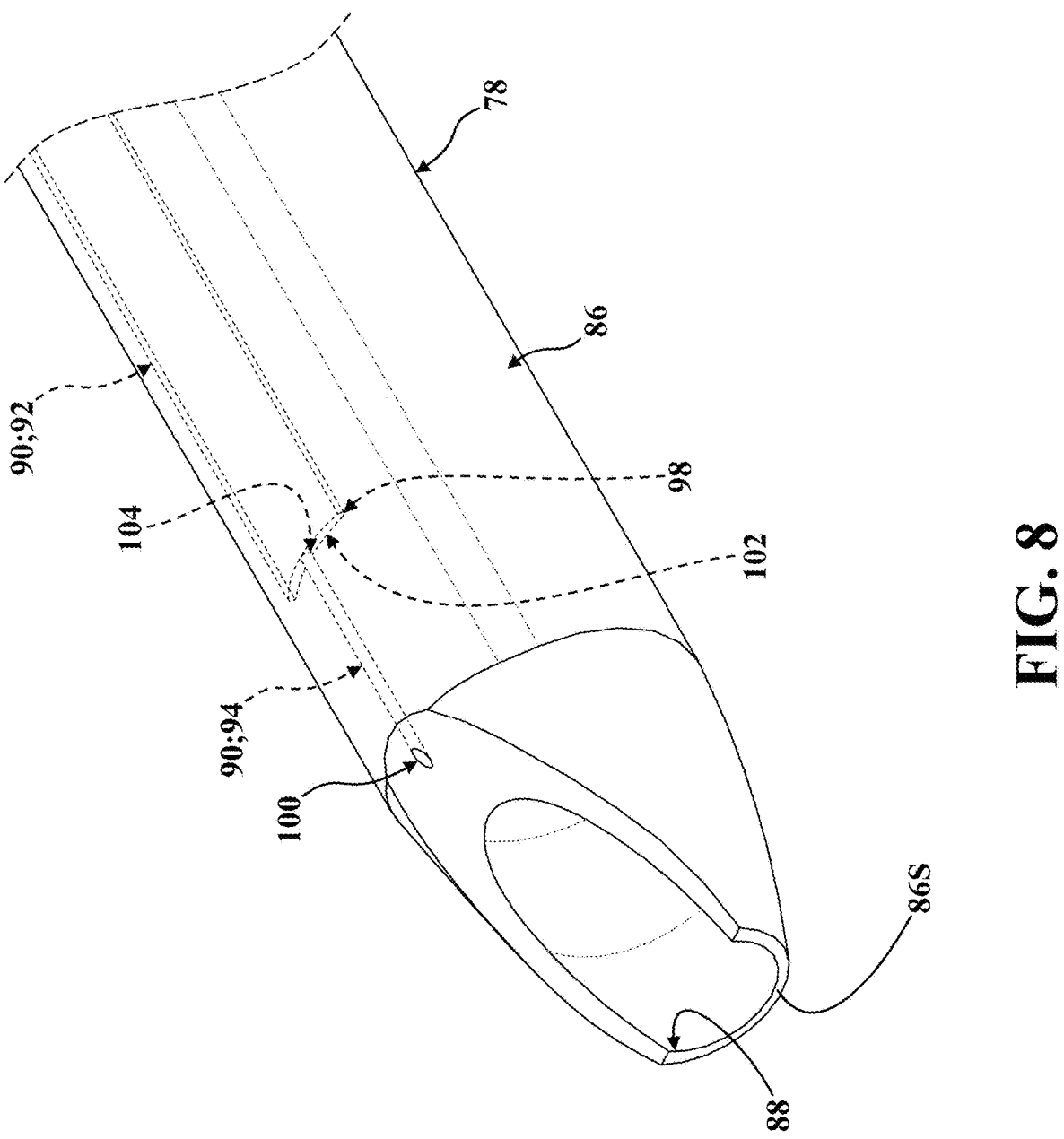
FIG. 8 is an enlarged, partial perspective view of the irrigation sleeve of FIG. 7, shown comprising first and second lumens, with the second lumen illustrated in phantom and shown comprising distal and proximal lumen regions spaced from the first lumen.
Figure 22:
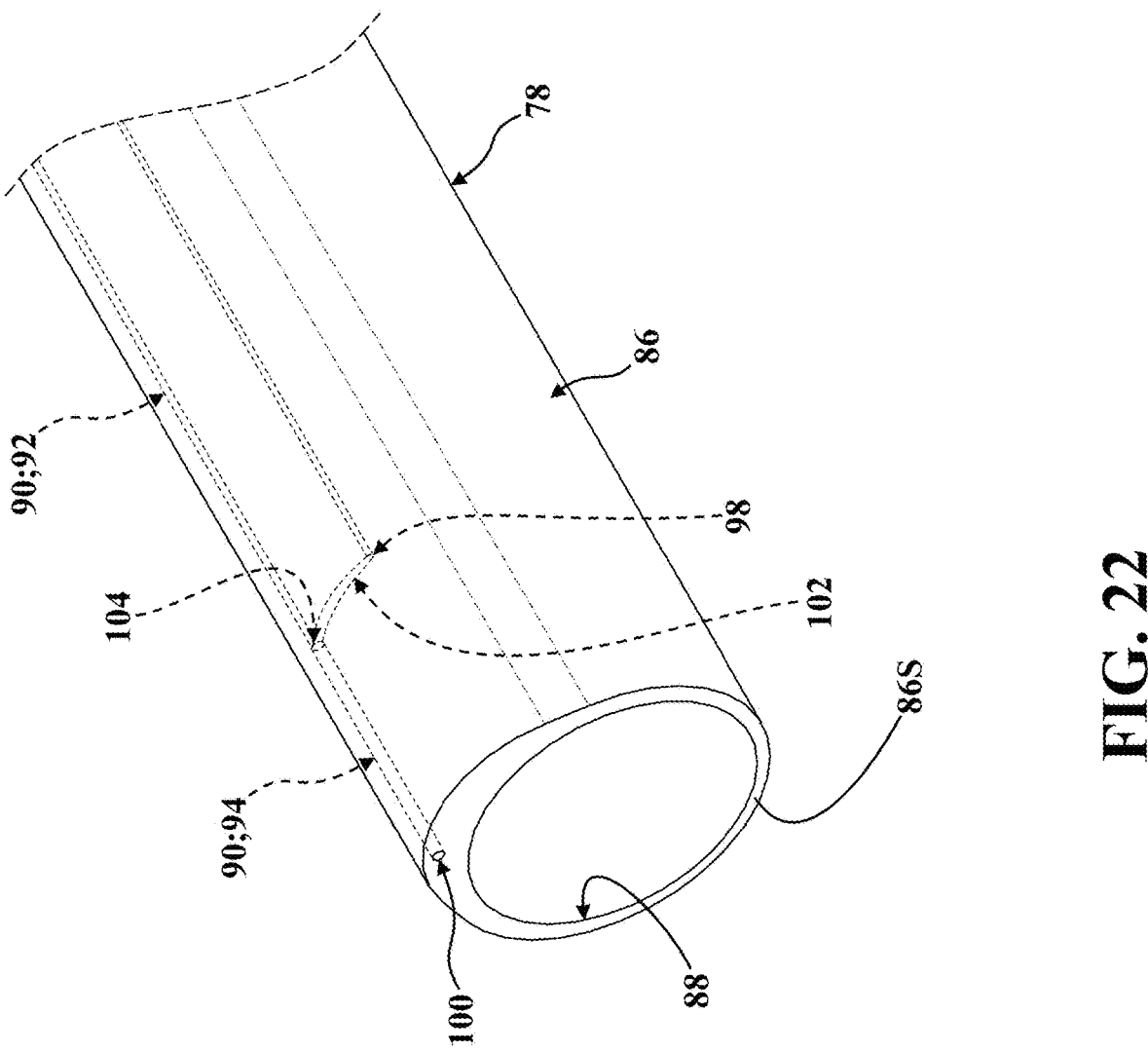
FIG. 22 is an enlarged, partial perspective view of the irrigation sleeve of FIG. 21, shown comprising first and second lumens, with the second lumen illustrated in phantom and shown comprising distal and proximal lumen regions spaced from the first lumen.

With reference to FIGS. 6, 8, and 22, the second lumen 90 of the sleeve body 86 comprises a proximal lumen region 92 and a distal lumen region 94. As is described in greater detail below, the distal lumen region 94 is configured differently from the proximal lumen region 92 such that the fluid FJ is projected in a consistent and reliable fashion and under a number of different operating conditions. In certain configurations, the distal lumen region 94 promotes projecting the fluid jet FJ away from the shank 66 of the cutting accessory 52. In certain configurations, the distal lumen region 94 promotes projecting the fluid jet FJ substantially parallel with the shank 66 of the cutting accessory 52. Other configurations are contemplated herein.

With continued reference to FIGS. 6, 8, and 22, the proximal lumen region 92 extends from a lumen inlet 96 (see FIG. 6) to a lumen transition 98. The lumen inlet 96 is adapted for fluid communication with the irrigation source 68 via the feeder tube 80 and the line 74 (see FIG. 1). The distal lumen region 94 extends from the lumen transition 98 to a lumen outlet 100. The lumen outlet 100 is arranged to direct fluid adjacent to the head 64 of the cutting accessory 52, as described in greater detail below. In some configurations, the lumen transition 98 defines a transition surface 102 (see also FIGS. 13-14 and 27-28), and the distal lumen region 94 extends in fluid communication between the lumen outlet 100 and the transition surface 102. To this end, and as is best shown in FIGS. 8 and 22, the distal lumen region 94 comprises a transition inlet 104 defined in the transition surface 102 such that the distal lumen region 94 extends in fluid communication between the transition inlet 104 and the lumen outlet 100. The first lumen 88, the second lumen 90, the proximal lumen region 92, the distal lumen region 94, the lumen inlet 96, the lumen transition 98, the lumen outlet 100, the transition surface 102, and the transition inlet 104 will each be described in greater detail below.

The irrigation sleeve 78 may be manufactured from a transparent or semi-transparent material so as to promote visibility of the rotary instrument 50 during use. In one configuration, the irrigation sleeve 78 is manufactured from a resilient, compliant, or otherwise expandable material, such as a soft plastic or rubber, to help the irrigation sleeve 78 conform to the shape of the tube 60 of the rotary instrument 50. To this end, the first lumen 88 is advantageously sized and dimensioned to closely fit over the tube 60 of the rotary instrument 50. Here, an inner surface of the first lumen 88 may be provided with a non-slip or high coefficient of friction coating (for example, a co-extruded and tacky thermoplastic elastomer) to prevent inadvertent movement between the irrigation sleeve 78 and the tube 60 of the rotary instrument 50. Conversely, the outer surface of the irrigation sleeve 78 may be provided with a smooth coating (for example, polytetrafluoroethylene), or may be covered with a water-activated lubricant, to help the irrigation sleeve 78 move towards the surgical site ST. In one configuration, the irrigation sleeve 78 is manufactured from a sterilizable material. However, those having ordinary skill in the art will appreciate that the irrigation sleeve 78 could be manufactured from any suitable material or combination or materials.

As noted above, the lumen inlet 96 of irrigation sleeve 78 is adapted for fluid communication with the irrigation source 68. To this end, as shown in FIG. 6, the lumen inlet 96 is arranged adjacent to the proximal sleeve end 86P of the sleeve body 86 and is coupled to the feeder tube 80. Here, the irrigation sleeve 78 is provided with a tube receptacle, generally indicated at 106, which is shaped to receive a portion of the feeder tube 80 therein so as to facilitate fluid communication between the feeder tube 80 and the distal lumen region 94 of the second lumen 90. In the irrigation sleeves 78 illustrated throughout the drawings, the tube receptacle 106 is formed integrally with the sleeve body 86 to define the lumen inlet 96, such as by widening the proximal lumen region 92 of the second lumen 90 adjacent to the proximal sleeve end 86P of the sleeve body 86 (sec FIGS. 9-12 and 23-26). However, those having ordinary skill in the art will appreciate that the lumen inlet 96 could be formed in any suitable way sufficient to facilitate fluid communication between the irrigation source 68 and the second lumen 90 of the irrigation sleeve 78. Furthermore, while the irrigation sleeves 78 illustrated herein comprise a single second lumen 90 with a single proximal lumen region 92 and a single distal lumen region 94, it will be appreciated that multiple proximal lumen regions 92 could be disposed in communication with a single distal lumen region 94. Similarly, a single proximal lumen region 92 could be disposed in communication with multiple distal lumen regions 94. Moreover, it will be appreciated that multiple second lumens 90 could be utilized.

Referring now to FIGS. 9-14 and 23-28, the first lumen 88 is aligned about a first lumen path 108 (see FIGS. 10-13 and 24-27), and the proximal lumen region 92 of the second lumen 90 is arranged about a second lumen path 110 (see FIGS. 11 and 25) spaced from the first lumen path 108. In the representative embodiments of the irrigation sleeve 78 illustrated herein, the first lumen path 108 and the second lumen path 110 are both linear, and the second lumen path 110 is radially spaced from and is aligned in parallel fashion with the first lumen path 108. This arrangement compliments the configuration of the tube 60 of the rotary instrument 50, which is illustrated throughout the drawings as having a generally straight-cylindrical profile. However, as noted above, the rotary instrument 50 could be configured in a number of different ways and, thus, could employ tubes 60 with different shapes, configurations, profiles, and the like. By way of non-limiting example, the tube could have a curved, cylindrical profile, wherein the first lumen path 108 and the second lumen path 110 here would be non-linear (curved) so as to compliment the profile of the tube. Here too in this example, the first lumen path 108 and the second lumen path 110 could be spaced from and aligned with respect to each other. However, irrespective of the specific configuration of the tube 60, those having ordinary skill in the art will appreciate that the first lumen path 108 and/or the second lumen path 110 could be arranged, disposed, or otherwise defined in any suitable way.

With continued reference to FIGS. 9-14 and 23-28, in one configuration, the distal lumen region 94 of the second lumen 90 is arranged about a third lumen path 112 which, like the second lumen path 110, is generally linear and is radially spaced in parallel fashion from the first lumen path 108. In the embodiment of the irrigation sleeve 78 illustrated in FIGS. 7-14, the third lumen path 112 is generally coincident with the second lumen path 110 (see FIGS. 13-14). However, in the embodiment of the irrigation sleeve 78 illustrated in FIGS. 21-28, the third lumen path 112 is radially spaced from the second lumen path 110 (see FIGS. 27-28). Here too, it will be appreciated that the third lumen path 112 may be arranged, disposed, or otherwise defined in a number of different ways.

In the illustrated embodiments of the irrigation sleeve 78 depicted throughout the drawings, and as is best shown in FIGS. 10-12 and 24-26, the first lumen 88 has a generally cylindrical profile which is complimentarily to the shape of the tube 60 of the rotary instrument 50. While the first lumen 88 is illustrated with a closed, circular periphery (e.g., an unbroken cylindrical profile), it is conceivable that the first lumen 88 could be slotted and/or could be configured with a different shape, profile, and the like. Other configurations are contemplated, and it will be appreciated that the first lumen 88 could have any suitable profile sufficient to receive a portion of the tube 60 of the rotary instrument 50.

Figure 17:
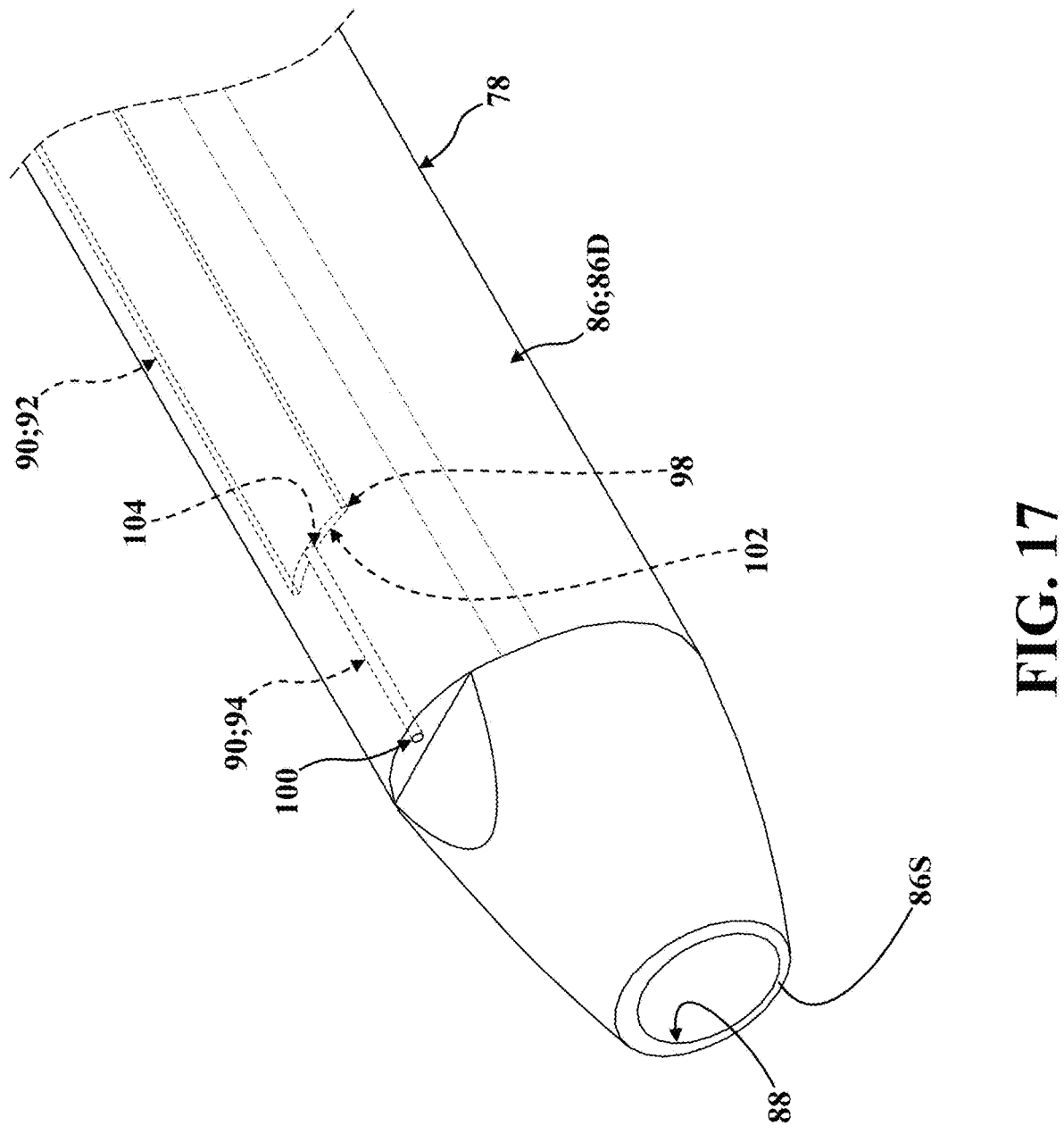
FIG. 17 is an enlarged, partial perspective view of a distal sleeve end of a sleeve body comprising first and second lumens, with the second lumen illustrated in phantom and shown comprising a proximal lumen region having a crescent-shaped profile and a distal lumen region having a cylindrical profile, and with the distal sleeve end of the sleeve body shown having a tapered profile through which a skive has been made to define a lumen outlet in fluid communication with the distal lumen region.
Figure 18:
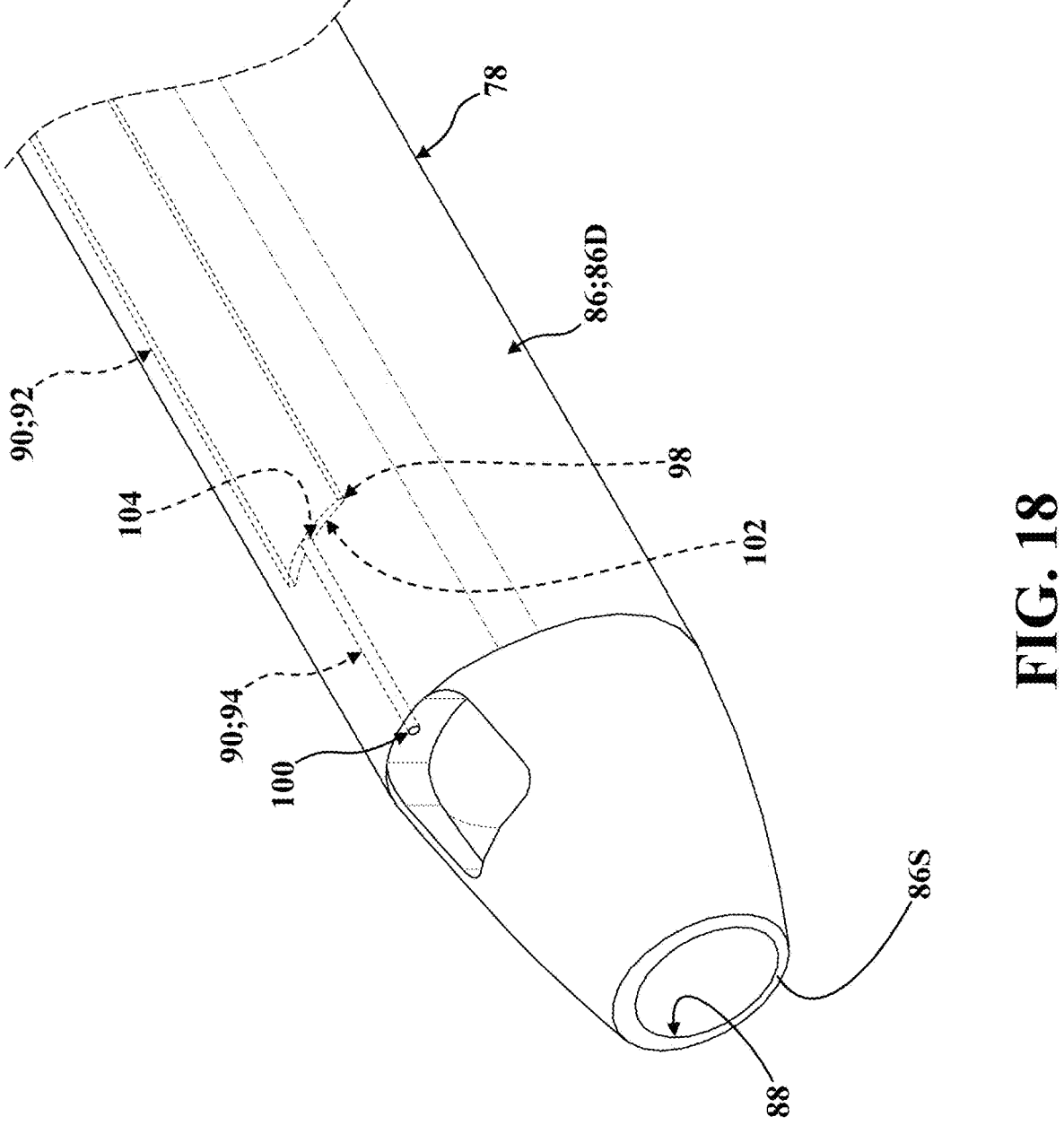
FIG. 18 is an enlarged, partial perspective view of a distal sleeve end of a sleeve body comprising first and second lumens, with the second lumen illustrated in phantom and shown comprising a proximal lumen region having a crescent-shaped profile and a distal lumen region having a cylindrical profile, and with the distal sleeve end of the sleeve body shown having a tapered profile through which a punch has been made to define a lumen outlet in fluid communication with the distal lumen region.

In the embodiment of the irrigation sleeve 78 depicted in FIGS. 7-14, the first lumen 88 has a generally tapered profile adjacent to the distal sleeve end 86S of the sleeve body 86, which is shaped complimentarily to the distal tube end 62 of the tube 60 of the rotary instrument 50, which likewise has a tapered and generally frustoconical profile (see also FIGS. 1-6). In the embodiment of the irrigation sleeve 78 illustrated in FIGS. 7-14, the distal sleeve end 86S of the sleeve body 86 has been chamfer cut through both the first lumen 88 and the distal lumen region 94 of the second lumen 90 such that the lumen outlet 100 is arranged between the lumen transition 98 and the distal sleeve end 86S of the sleeve body 86. However, in the embodiment of the irrigation sleeve 78 illustrated in FIGS. 21-28, the distal sleeve end 86S of the sleeve body 86 has been cut transversely through both the first lumen 88 and the distal lumen region 94 of the second lumen 90 such that the lumen outlet 100 is arranged at the distal sleeve end 86S of the sleeve body 86. As noted above, the sleeve body 86 could have other profiles, configurations, and the like (see, for example, FIGS. 17-19).

Figures 9, 10, 11, 12:
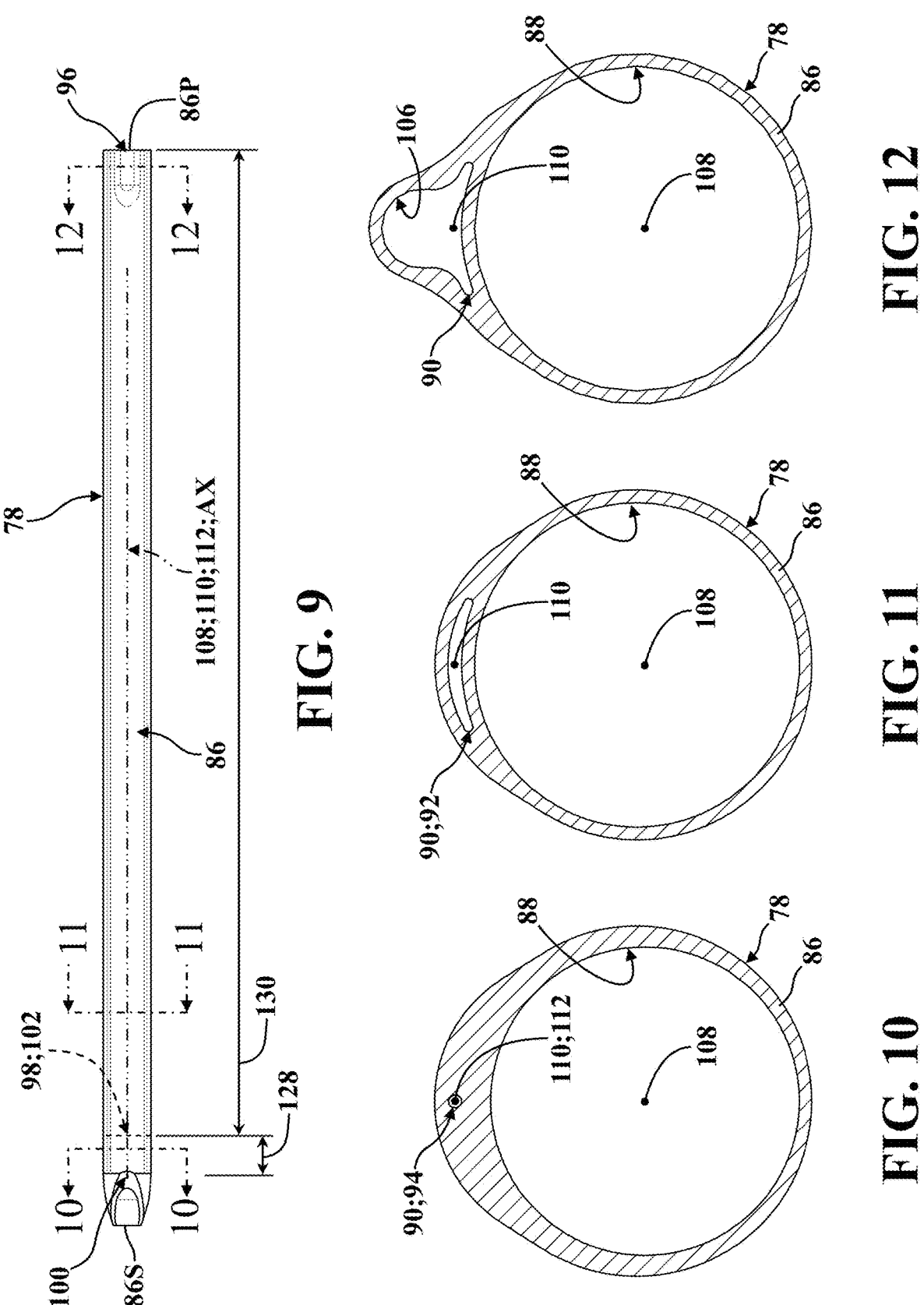
FIG. 9 is a top-side plan view of the irrigation sleeve of FIGS. 7-8.
FIG. 10 is a slice-section view taken along line 10-10 in FIG. 9.
FIG. 11 is a slice-section view taken along line 11-11 in FIG. 9.
FIG. 12 is a slice-section view taken along line 12-12 in FIG. 9.
Figure 13:
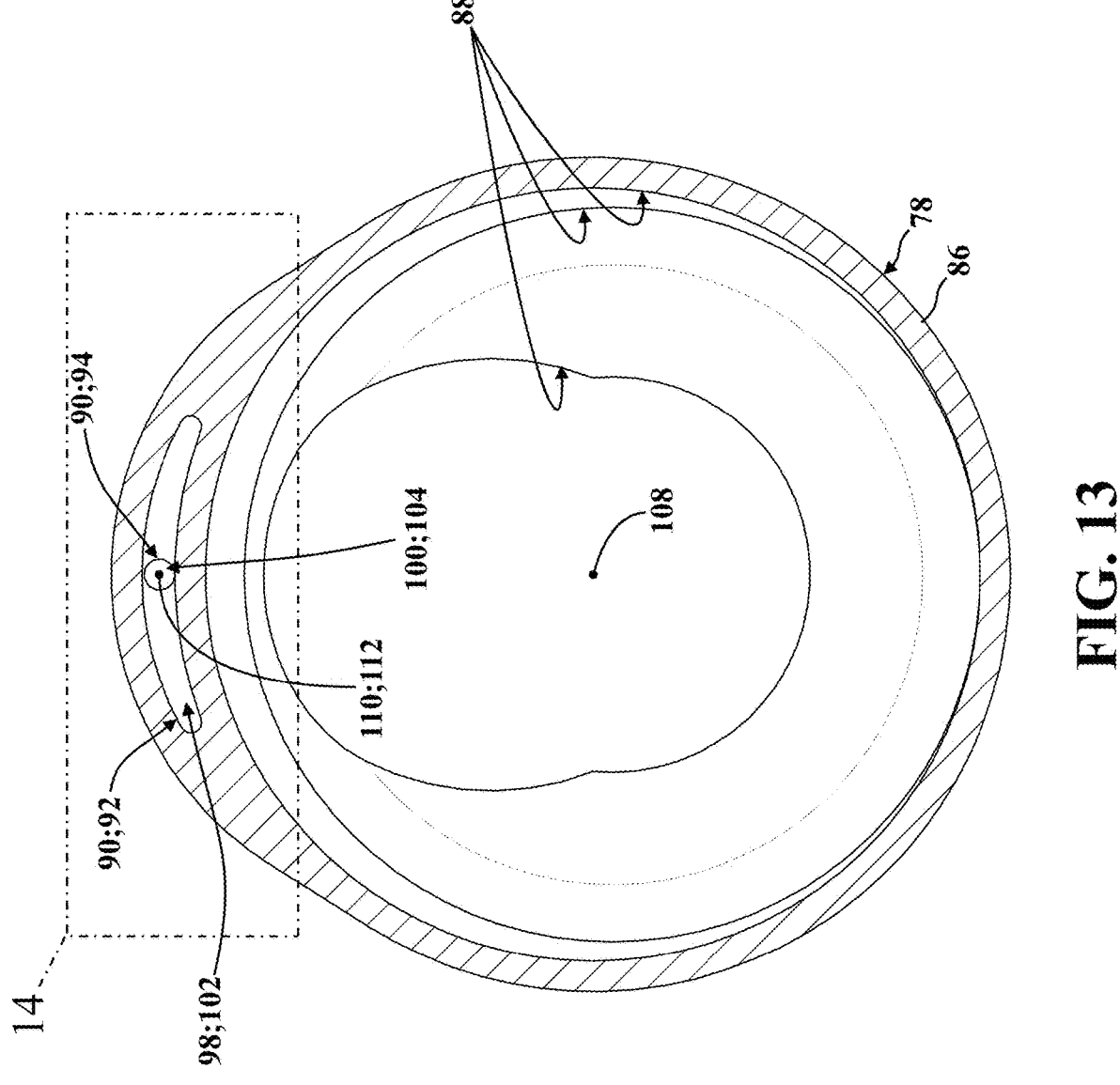
FIG. 13 is a sectional view taken along line 11-11 in FIG. 9.
Figures 23, 24, 25, 26:
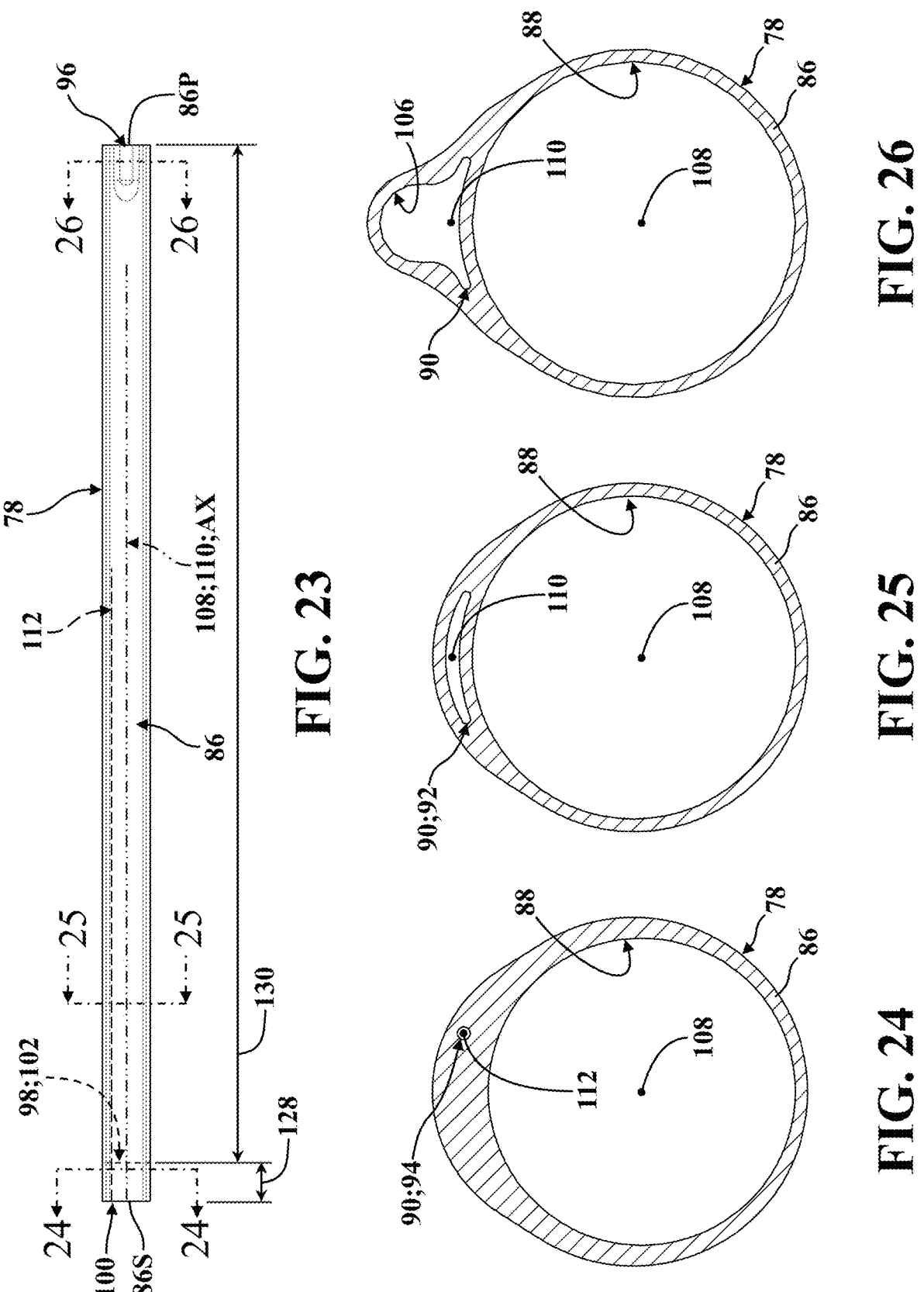
FIG. 23 is a top-side plan view of the irrigation sleeve of FIGS. 21-22.
FIG. 24 is a slice-section view taken along line 24-24 in FIG. 23.
FIG. 25 is a slice-section view taken along line 25-25 in FIG. 23.
FIG. 26 is a slice-section view taken along line 26-26 in FIG. 23.
Figure 27:
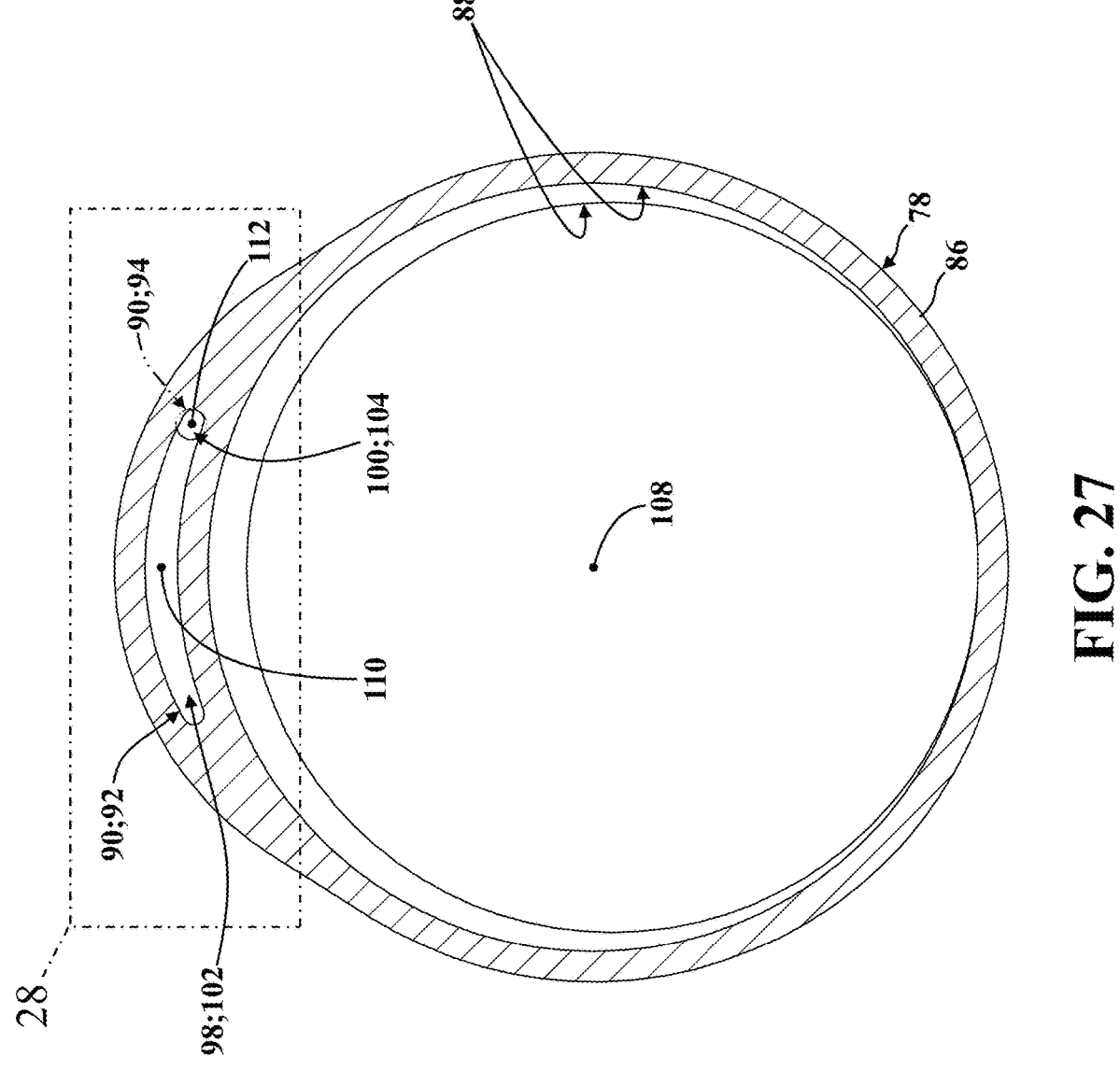
FIG. 27 is a sectional view taken along line 25-25 in FIG. 23.

In the embodiments of the irrigation sleeve 78 illustrated throughout the drawings, the proximal lumen region 92 of the second lumen 90 has a generally crescent-shaped profile (see FIGS. 11 and 25) and the distal lumen region 94 of the second lumen 90 has a generally cylindrical profile (see FIGS. 10 and 24). Here, the crescent-shaped profile of the proximal lumen region 92 is configured so as to accumulate fluid along the length of the sleeve body 86 to be provided to the distal lumen region 94 while, at the same time, efficiently positioning the fluid within the second lumen 90 of the irrigation sleeve 78 in close proximity to the tube 60 of the rotary instrument 50. It will be appreciated that this configuration affords significant advantages to the overall size of the irrigation sleeve 78. However, those having ordinary skill in the art will recognize that the proximal lumen region 92 could have different shapes, arrangements, and the like sufficient to direct fluid towards the distal lumen region 94 along the length of the sleeve body 86 and, thus, other proximal lumen region 92 profiles are contemplated, including but not limited to circular, polygonal, rectangular, and the like.

Referring now to FIGS. 8, 13-14, 22, and 27-28, as noted above, the lumen transition 98 defines the transition surface 102 such that the distal lumen region 94 extends in fluid communication between the lumen outlet 100 and the transition inlet 104 defined in the transition surface 102. As is best shown in FIGS. 8 and 22, the transition surface 102 is generally planar and acts as a "step" between the proximal lumen region 92 and the distal lumen region 94 of the second lumen 90. However, it will be appreciated that the transition surface 102 could be configured differently, such as with a "draft," so as to taper between the proximal lumen region 92 and the distal lumen region 94.

Figure 14:
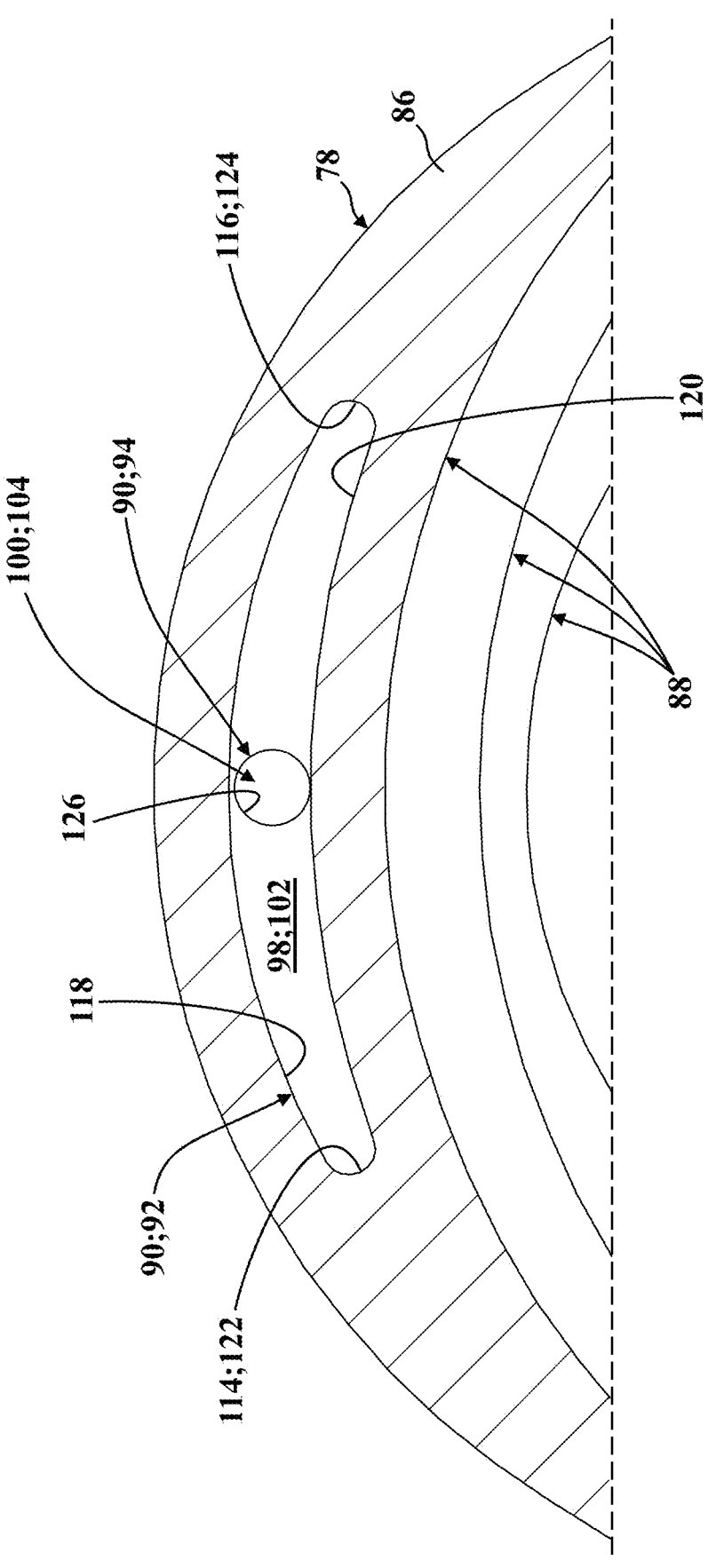
FIG. 14 is an enlarged, partial sectional view taken along indicia 14 in FIG. 13.
Figure 28:
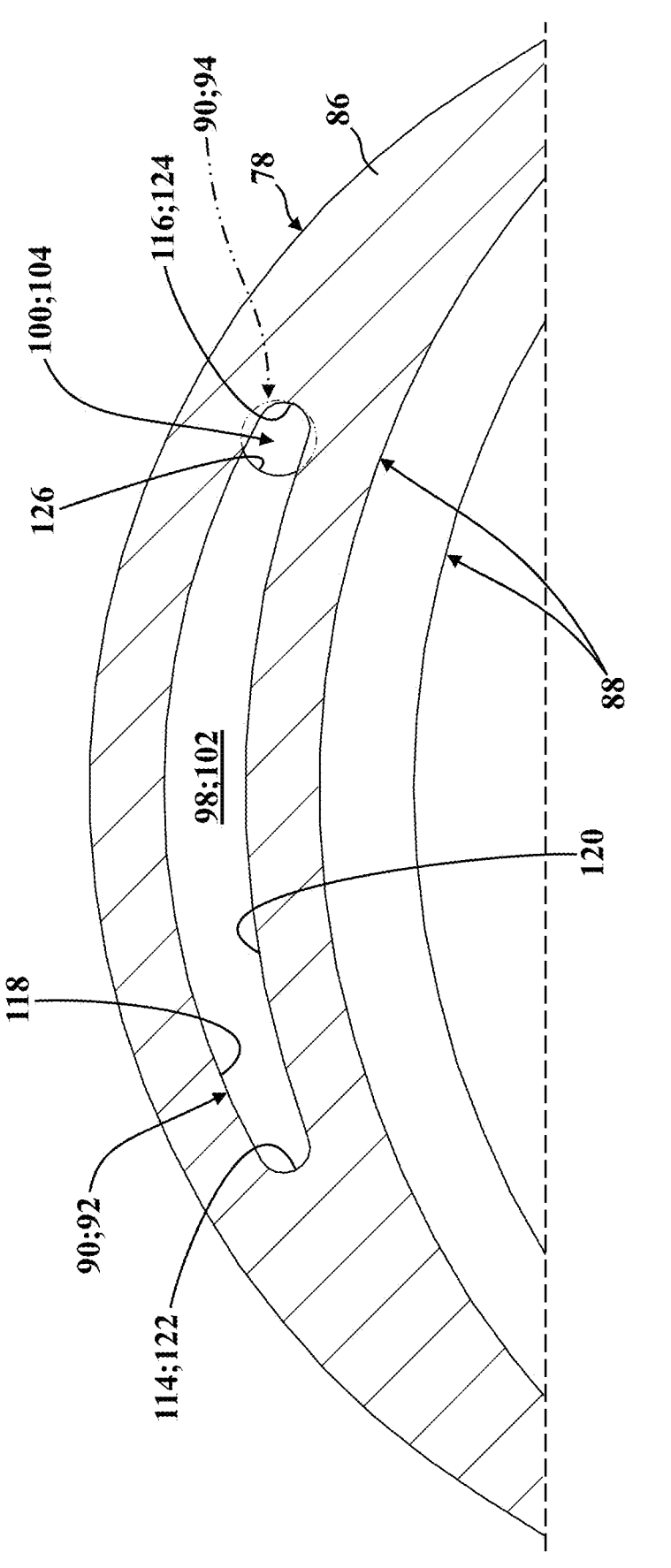
FIG. 28 is an enlarged, partial sectional view taken along indicia 28 in FIG. 27.

It will be appreciated that the outer periphery of the transition surface 102 is defined at least partially by the generally crescent-shaped profile of the the proximal lumen region 92 of the second lumen 90. More specifically, as shown in FIGS. 14 and 28, the proximal lumen region 92 of the second lumen 90 has a profile comprising a first lumen corner surface 114, a second lumen corner surface 116, a first arc surface 118, and a second arc surface 120. The first and second arc surfaces 118, 120 face towards each other and extend between the first and second lumen corner surfaces 114, 116. In the embodiments of the irrigation sleeve 78 depicted in FIGS. 14 and 28, the transition surface 102 has a profile comprising a first transition corner surface 122 which is arranged generally coincident with the first lumen corner surface 114 of the proximal lumen region 92. However, it will be appreciated that other alignments are contemplated (e.g, concentric alignment).

Referring specifically to the embodiment of the irrigation sleeve 78 depicted in FIG. 14, the transition surface 102 has a profile further comprising a second transition corner surface 124 which is similarly arranged so as to be generally coincident with the second lumen corner surface 116 of the proximal lumen region 92. Here too, other alignments are contemplated. Furthermore, in this embodiment, the transition inlet 104 has a generally cylindrical profile and is formed in the transition surface 102 so as to be arranged between the first transition corner surface 122 and the second transition corner surface 124. While the transition inlet 104 is generally illustrated as being disposed equidistantly between the first and second transition corner surfaces 122, 124, other configurations are contemplated.

Referring specifically to the embodiment of the irrigation sleeve 78 depicted in FIG. 28, the transition surface 102 has a profile further comprising an inlet corner surface 126 defined by the transition inlet 104, which is likewise illustrated with a generally cylindrical profile. Here, the transition inlet 104 is arranged so as to be generally coincident with the inlet corner surface 126 of the transition surface 102, and also generally coincident with the second lumen corner surface 116 of the proximal lumen region 92 of the second lumen 90. Here too, it will be appreciated that other alignments are contemplated.

As noted above, the proximal lumen region 92 and the distal lumen region 94 of the second lumen 90 are configured differently from each other. To this end, in one configuration, the proximal lumen region 92 has a larger cross sectional area than the distal lumen region 94 taken at the lumen transition 98 (see FIGS. 8, 14, 22, and 28). As will be appreciated from the subsequent description below, neither the cross sectional area of the proximal lumen region 92 nor the cross sectional area of the distal lumen region 94 varies substantially along the respective length of the sleeve body 86 in the illustrated embodiment of the irrigation sleeve 78. In light of the forgoing, for the embodiment of the irrigation sleeve 78 depicted in FIGS. 7-14, FIGS. 10 and 11 (which are for the purposes of this description shown at the same scale) comparatively illustrate the cross sectional areas of the distal lumen region 94 (see FIG. 10) and of the proximal lumen region 92 (see FIG. 11). Put differently, FIGS. 10 and 11 are representative of the cross sectional areas of the distal lumen region 94 and the proximal lumen region 92, respectively, taken adjacent to the lumen transition 98 in this embodiment (see also FIGS. 13-14). Furthermore and similarly, for the embodiment of the irrigation sleeve 78 depicted in FIGS. 21-28, FIGS. 24 and 25 (which are for the purposes of this description shown at the same scale) comparatively illustrate the cross sectional areas of the distal lumen region 94 (see FIG. 24) and of the proximal lumen region 92 (see FIG. 25). Put differently, FIGS. 24 and 25 are representative of the cross sectional areas of the distal lumen region 94 and the proximal lumen region 92, respectively, taken adjacent to the lumen transition 98 in this embodiment (see also FIGS. 27-28).

In one configuration, the cross sectional area of the proximal lumen region 92 is between two and twenty times larger than the larger than the cross sectional area of the distal lumen region 94. In one configuration, the cross sectional area of the proximal lumen region 92 is between five and fifteen times larger than the larger than the cross sectional area of the distal lumen region 94. In one configuration, the cross sectional area of the proximal lumen region 92 at least ten times larger than the cross sectional area of the distal lumen region 94.

Referring now to FIGS. 9 and 23, the lumen transition 98 is arranged closer to the distal sleeve end 86S than to the proximal sleeve end 86P. In one configuration, a first distance 128 is defined between the lumen outlet 100 and the lumen transition 98, and a second distance 130, larger than the first distance 128, is defined between the lumen transition 98 and the lumen inlet 96.

Those having ordinary skill in the art will appreciate that relatively long fluid paths with relatively small cross sectional areas resist fluid flow. Moreover, too much resistance to flow can adversely impact the ability of the irrigation source 68 to direct fluid towards the surgical site ST. Here, because of the differences in the profiles, cross sectional areas, and relative lengths of the proximal lumen region 92 and the distal lumen region 94 described above, fluid can travel along the proximal lumen region 92 towards the distal lumen region 94 without significant pressure increase, while, at the same time, ensuring that the fluid jet FJ projects from the lumen outlet 100 to beyond and adjacent to the head 64 of the cutting accessory 52 during use (see FIGS. 2-3).

Furthermore, it will be appreciated that the configuration of the irrigation sleeve 78 described above affords significant advantages for certain medical and surgical procedures where providing irrigation to the surgical site ST is otherwise difficult, such as in connection with minimally invasive surgical procedures (for example, minimally invasive spinal surgery), endoscopic surgical procedures (for example, endoscopic transnasal surgery), and the like.

Referring now to FIGS. 2-3, as noted above, the irrigation sleeve 78 can advantageously be used to promote irrigation of surgical sites ST, such as to irrigate bone BN. Here, it will be appreciated that contacting bone BN before the bur head 64 with the fluid jet FJ advantageously minimizes or otherwise prevents "splashing" of fluid across the surgical site ST which could otherwise be caused by fluid contacting the shank 66 of the cutting accessory 52, or by fluid which projects directly towards the bur head 64. However, depending on the preferences of the medical professional and the procedure being performed, it may be advantageous to "skim" the outer edge of the bur head 64 in certain applications, which can be achieved by adjusting the irrigation source 68 and/or by adjusting the relative position and/or orientation of the lumen outlet 100 relative to the bur head 64 by moving the irrigation sleeve 78 along the tube 60 of the rotary instrument 50.

The process of manufacturing the embodiment of the irrigation sleeve 78 illustrated in FIGS. 7-14 is disclosed and described below in connection with FIGS. 15A-20F, and the process of manufacturing the embodiment of the irrigation sleeve 78 illustrated in FIGS. 21-28 is disclosed and described below in connection with FIGS. 29-30I.

Figures 15A, 15B:
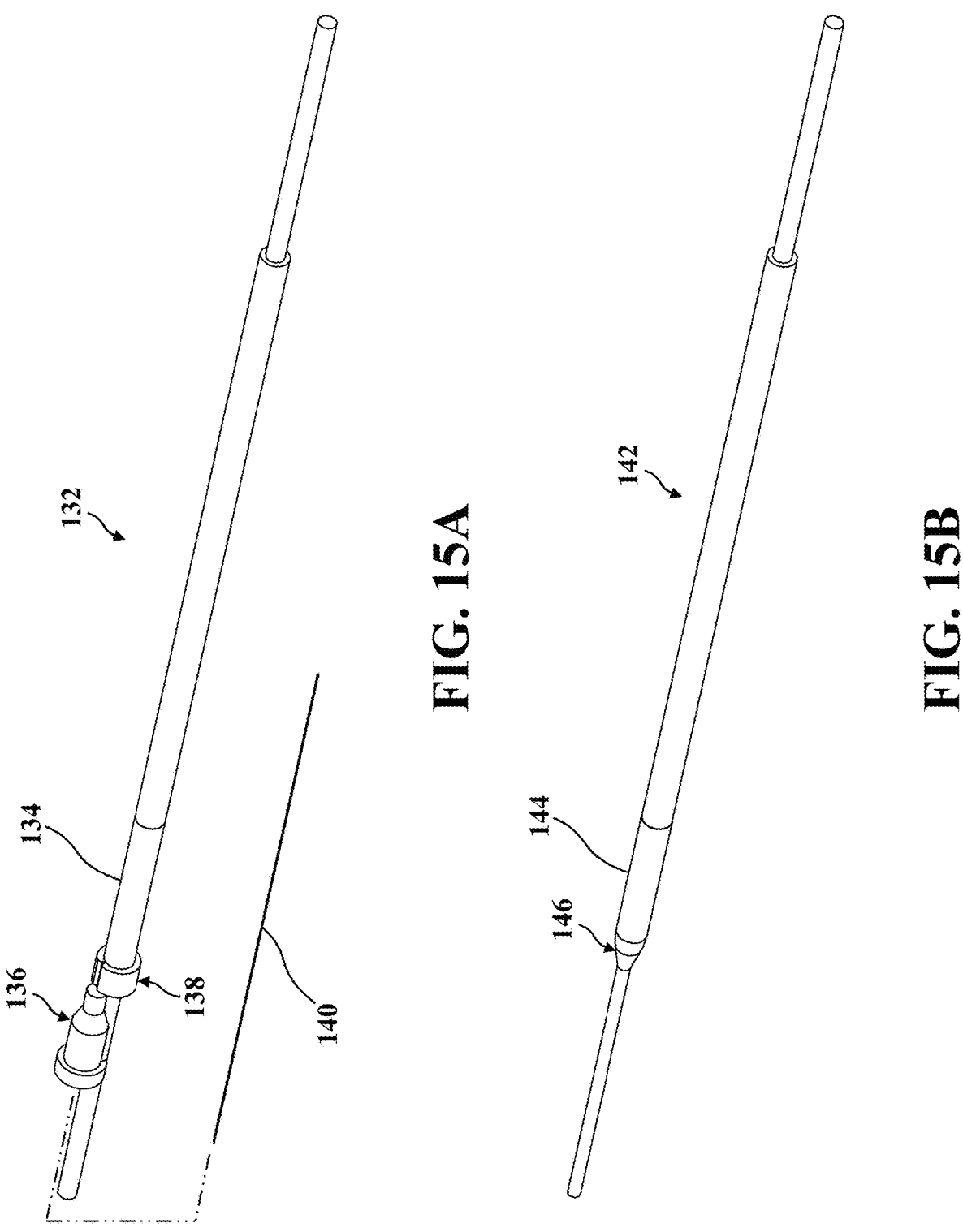
FIG. 15A is a partially-exploded perspective view of a first mandrel assembly, the first mandrel assembly shown comprising a first mandrel spaced from a shaft.
FIG. 15B is a perspective view of a second mandrel assembly.

Referring now to FIGS. 15A-20F, a first mandrel assembly, generally indicated at 132, is shown in FIG. 15A. The illustrated first mandrel assembly 132 comprises a first mandrel body 134, an insertion guide 136, a collar 138, and a shaft 140. Here, the first mandrel body 134 extends from the collar 138 which, in turn, supports the insertion guide 136. The insertion guide 136 has a hollow, tapered, "funnel" configuration and is shaped to support the shaft 140 therethrough. In FIG. 15B, a second mandrel assembly, generally indicated at 142, is shown comprising a second mandrel body 144 having a conical region 146. In FIGS. 16A-16D, the embodiment of the irrigation sleeve 78 described above in connection with FIGS. 7-14 is shown in progressive and/or alternative "steps" of manufacture, as described in greater detail below in connection with FIGS. 20A-20F.

Figure 16A:
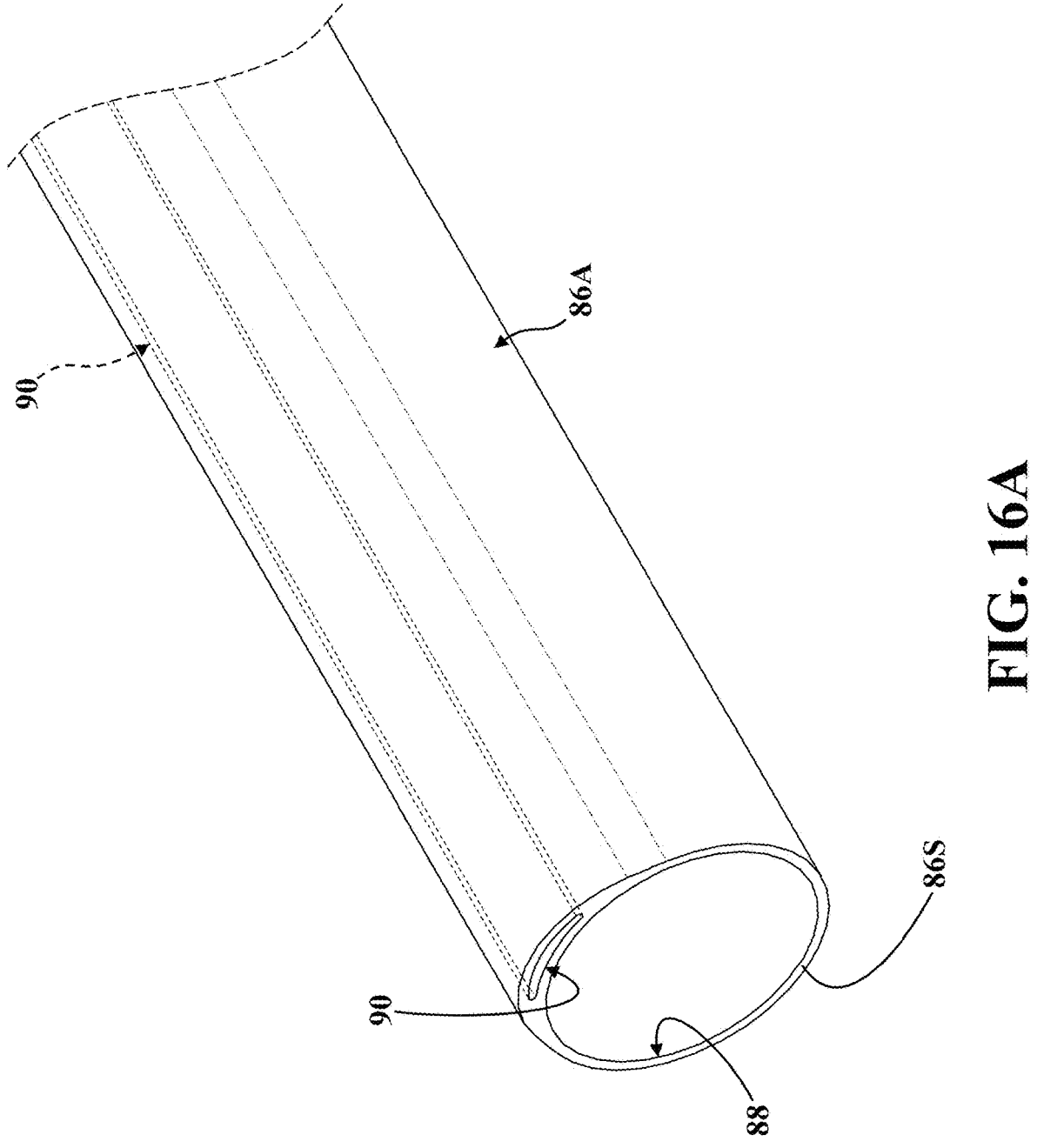
FIG. 16A is an enlarged, partial perspective view of a distal sleeve end of a sleeve body comprising first and second lumens, with the second lumen illustrated in phantom and shown having a crescent-shaped profile.

In FIG. 16A, a first sleeve body 86A is shown partially. Here, the first sleeve body 86A likewise extends between the distal sleeve end 86S and proximal sleeve end 86P (not shown). Here, too, the first lumen 88 and the second lumen 90 are formed in the first sleeve body 86A and are spaced from each other. At this step of manufacturing, and according to the representative embodiment illustrated herein, the second lumen 90 has the crescent-shaped profile along the entire length of the first sleeve body 86A between the distal sleeve end 86S and the proximal sleeve end 86P. However, as noted above, other profiles of the second lumen 90 are contemplated. Here, it will be appreciated that the first sleeve body 86A can advantageously be provided via an extrusion manufacturing process, which allows the longitudinal length of the first sleeve body 86A (and, thus, of the irrigation sleeve 78) to be easily adjusted for particular applications without a significant increase in manufacturing cost.

Figure 20A:
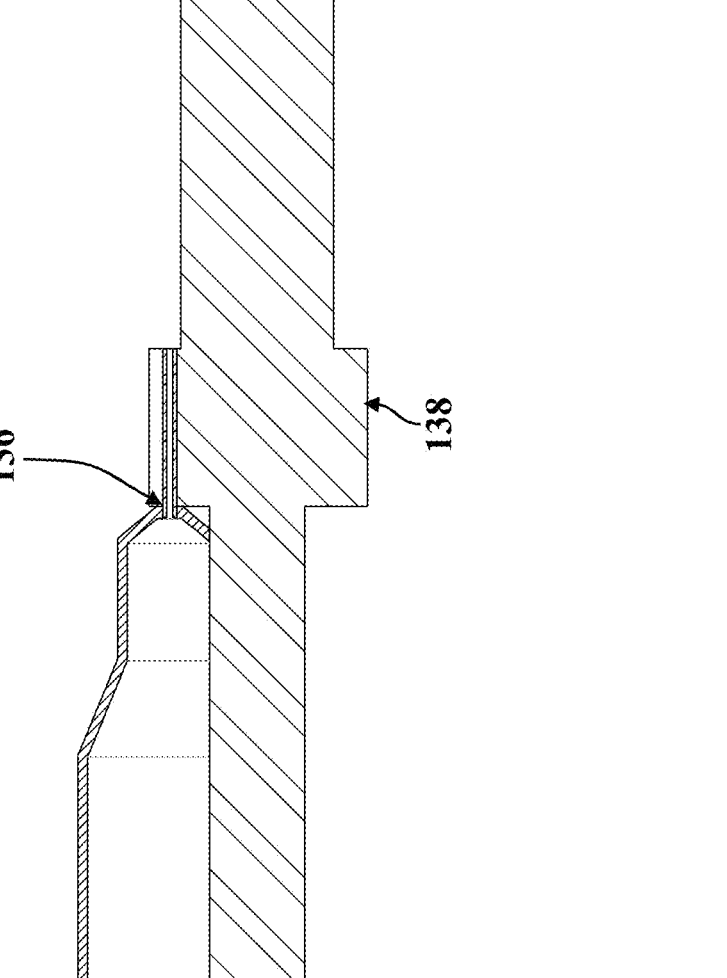
FIG. 20A is an enlarged, partial sectional view taken longitudinally through the first mandrel of the first mandrel assembly of FIG. 15A.
Figure 20B:
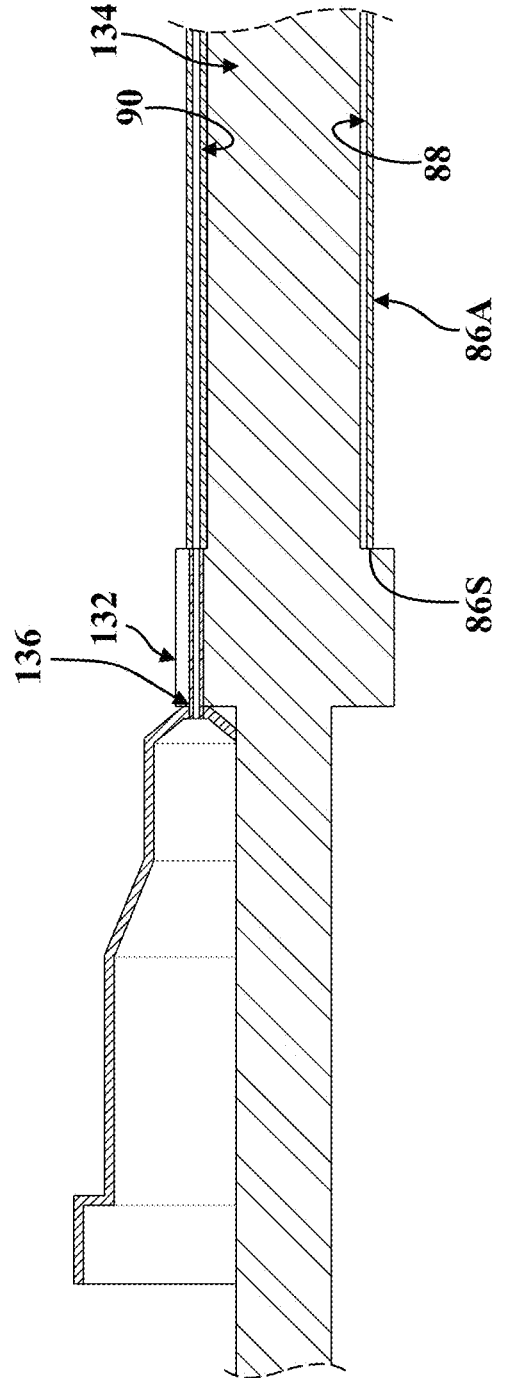
FIG. 20B is another enlarged, partial sectional view of the first mandrel assembly of FIG. 20A, shown supporting the distal sleeve end of the sleeve body depicted in FIG. 16A.
Figure 20C:
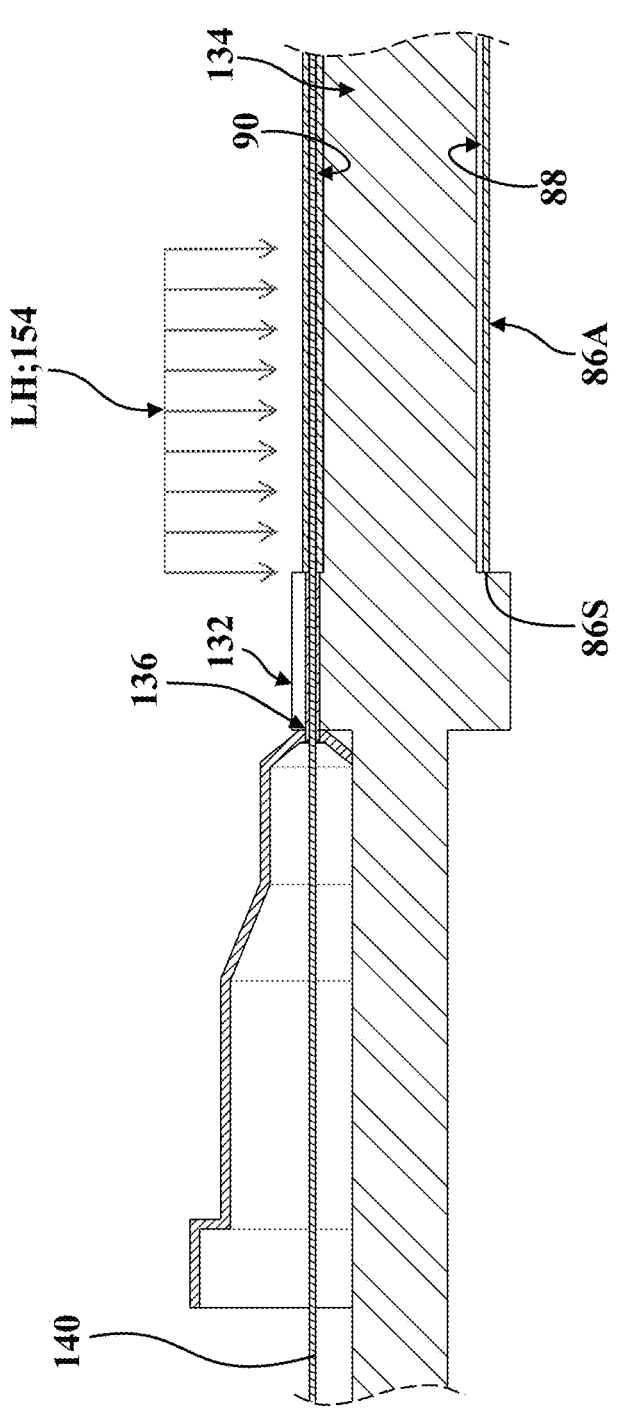
FIG. 20C is another enlarged, partial sectional view of the first mandrel assembly and the sleeve body of FIG. 20B, shown with the shaft of FIG. 15A positioned through an insertion guide of the first mandrel assembly and into the second lumen of the sleeve body depicted in FIG. 16A.

Referring now to FIGS. 20A-20C, portions of first mandrel assembly 132 are depicted in cross section. FIG. 20A shows the first mandrel body 134, the insertion guide 136, and the collar 138 of the first mandrel assembly 132. FIG. 20B illustrates a progressive step continuing from FIG. 20A, and shows the first sleeve body 86A described above as supported on a portion of the first mandrel body 134, which is positioned so as to extend through the first lumen 88 of the first sleeve body 86A. FIG. 20B also shows the distal sleeve end 86S of the sleeve body 86 abutting the collar 138 of the first mandrel assembly 132. FIG. 20C illustrates a progressive step continuing from FIG. 20B, and shows the shaft 140 of the first mandrel assembly 132 positioned extending through the insertion guide 136 and into the second lumen 90. Here, it will be appreciated that the first mandrel assembly 132 can be configured so as to allow the shaft 140 to be aligned in a number of different ways. Specifically, while the proximal lumen region 92 and the distal lumen region 94 of the second lumen 90 are generally aligned with each other in this embodiment (compare FIGS. 10 and 11, see also FIG. 14), different arrangements, alignments, and configurations are contemplated.

After the first sleeve body 86A has been positioned with respect to the first mandrel assembly 132 as illustrated in FIG. 20C, the first sleeve body 86A is reformed into a second sleeve body 86B, such as by applying localized heat LH to the first sleeve body 86A adjacent to the distal sleeve end 86S. Here, heat could be applied using various localized heating devices, such as laser heating, heat guns, and the like. As described in greater detail below in connection with FIGS. 30A-30I, heat-shrink tubing may be positioned over the first sleeve body 86A so as to apply hoop compression to the first sleeve body 86A as the material is reformed into the second sleeve body 86B. The second sleeve body 86B is best depicted in FIG. 16B and is described in greater detail below in connection with FIG. 20D.

Figure 16B:
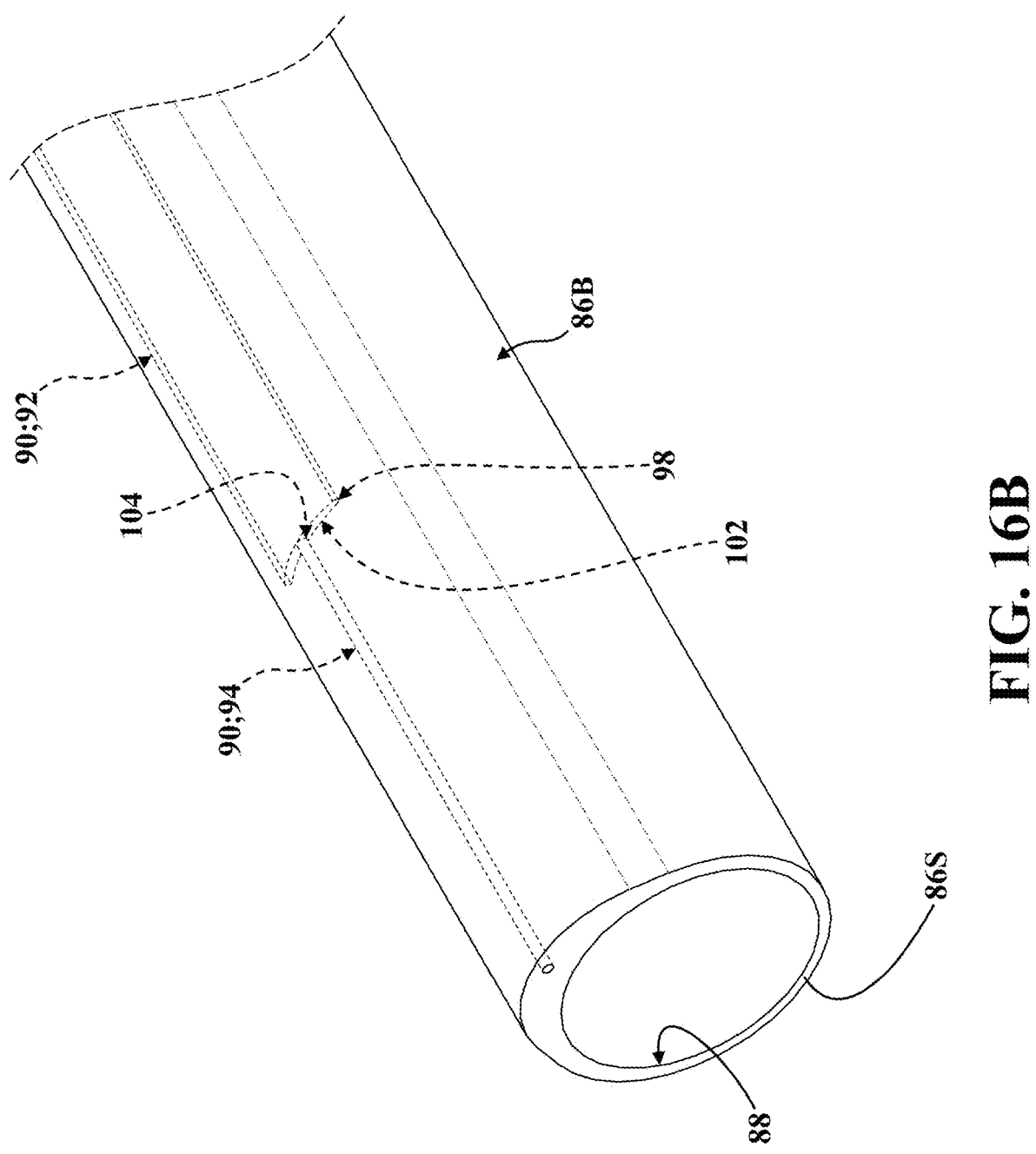
FIG. 16B is an enlarged, partial perspective view of a distal sleeve end of a sleeve body comprising first and second lumens, with the second lumen illustrated in phantom and shown comprising a proximal lumen region having a crescent-shaped profile and a distal lumen region having a cylindrical profile.
Figure 16C:
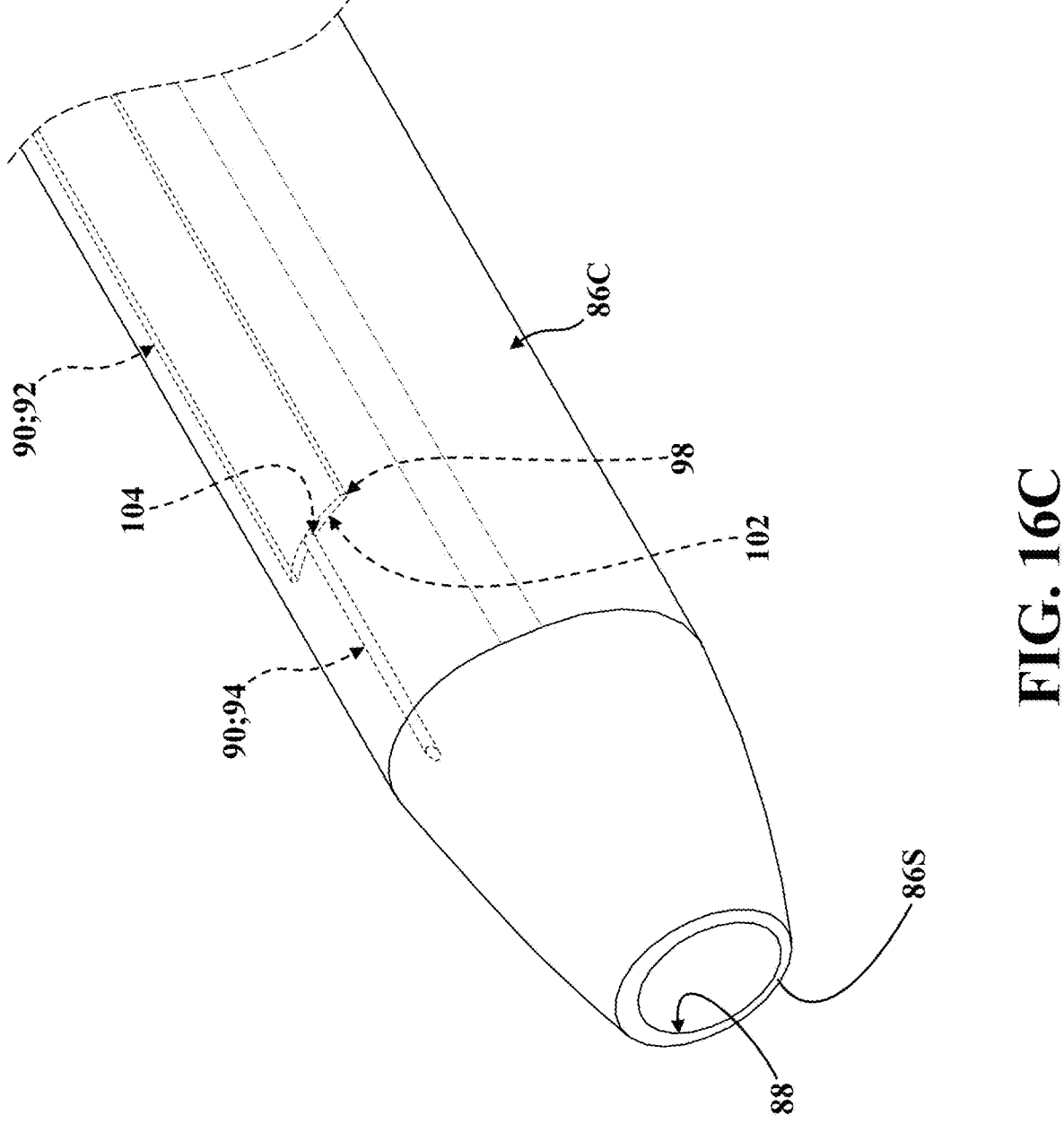
FIG. 16C is an enlarged, partial perspective view of a distal sleeve end of a sleeve body comprising first and second lumens, with the second lumen illustrated in phantom and shown comprising a proximal lumen region having a crescent-shaped profile and a distal lumen region having a cylindrical profile, and with the distal sleeve end of the sleeve body shown having a tapered profile.
Figure 16D:
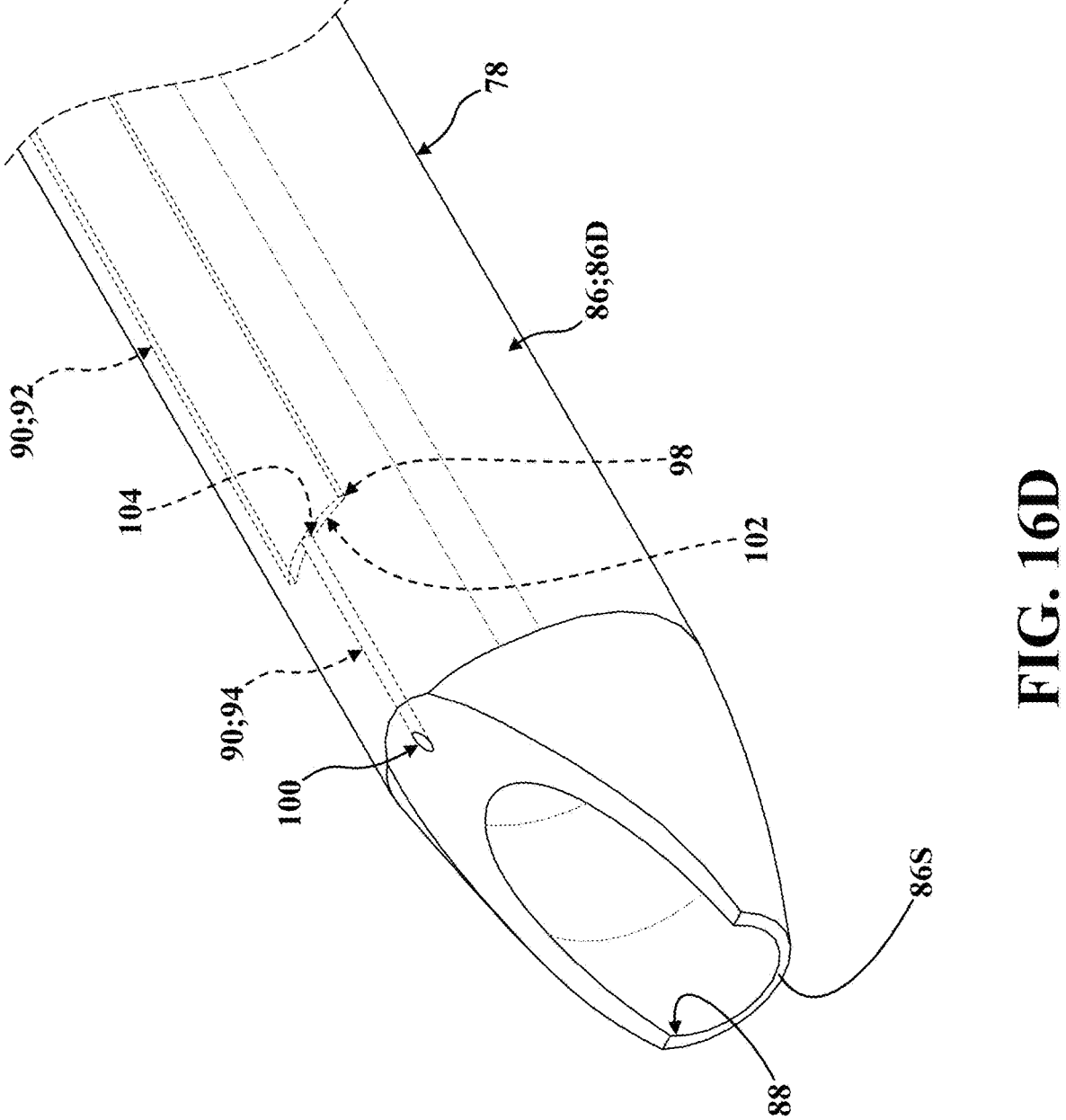
FIG. 16D is an enlarged, partial perspective view of a distal sleeve end of a sleeve body comprising first and second lumens, with the second lumen illustrated in phantom and shown comprising a proximal lumen region having a crescent-shaped profile and a distal lumen region having a cylindrical profile, and with the distal sleeve end of the sleeve body shown having a tapered profile through which a chamfer cut has been made to define a lumen outlet in fluid communication with the distal lumen region.

As shown in FIG. 16B, the second sleeve body 86B is configured such that at least a portion of the distal sleeve end 86S has been reformed around the shaft 140 of the first mandrel assembly 132 so as to differentiate the second lumen 90 into the distal lumen region 94 having a cylindrical profile defined by the shaft 140, and the proximal lumen region 92, which retains the crescent-shaped profile described above in connection with the first sleeve body 86A. At this point, the second sleeve body 86B is removed from the first mandrel body 134, the shaft 140 is removed from the second lumen 90, and the second sleeve body 86B is then supported on the second mandrel body 144 of the second mandrel assembly 142, as depicted in FIG. 20D.

Figure 20D:
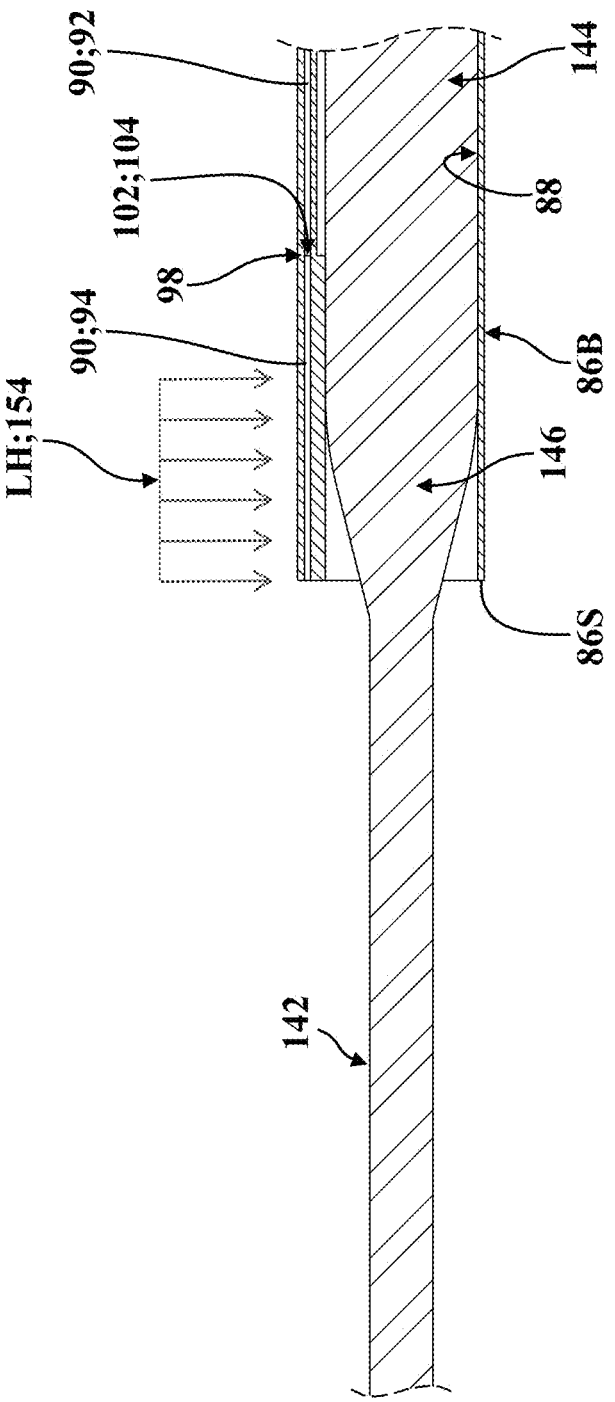
FIG. 20D is an enlarged, partial sectional view taken longitudinally through the second mandrel assembly of FIG. 15B, shown with the second mandrel assembly supporting the distal sleeve end of the sleeve body depicted in FIG. 16B.
Figure 20E:
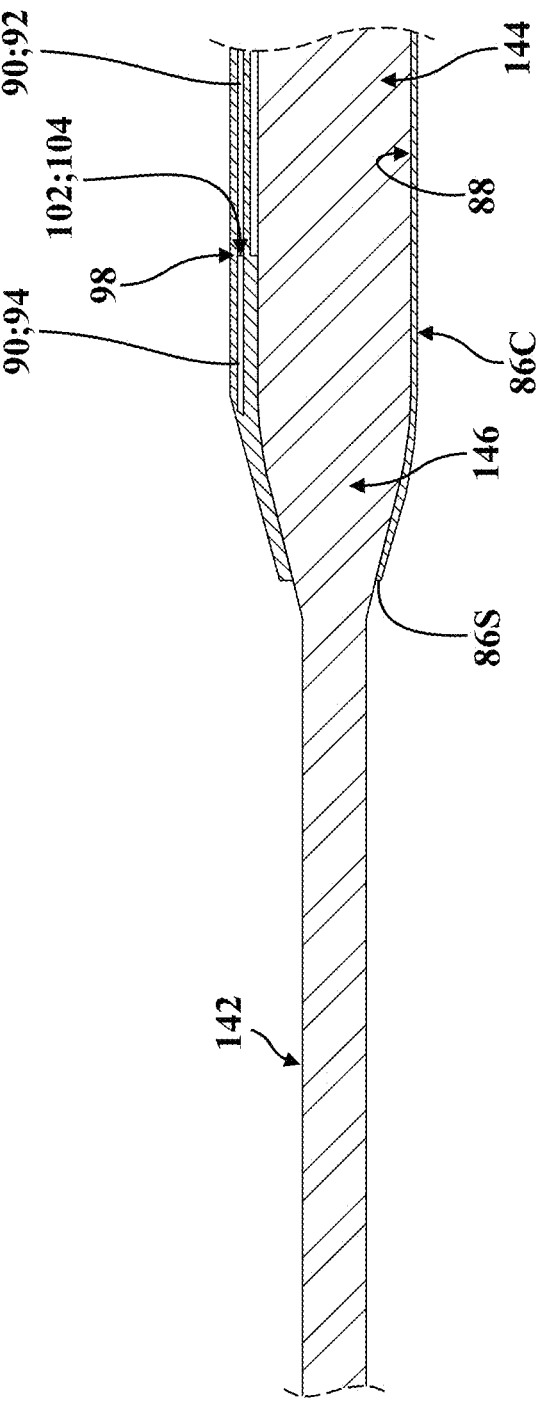
FIG. 20E is another enlarged, partial sectional view of the second mandrel assembly of FIG. 20D, shown with the second mandrel assembly supporting the distal sleeve end of the sleeve body depicted in FIG. 16C.

After the second sleeve body 86B has been positioned with respect to the second mandrel assembly 142 as illustrated in FIG. 20D, the second sleeve body 86B is reformed into a third sleeve body 86C (see FIG. 16C), such as by applying localized heat LH to the second sleeve body 86B adjacent to the distal sleeve end 86S to "shrink" the distal sleeve end 86S around the conical region 146. Specifically, FIG. 20E illustrates a progressive step continuing from FIG. 20D, and shows the third sleeve body 86C reformed around conical region 146 of the second mandrel assembly 142 so as to define a correspondingly-shaped tapered profile adjacent to the distal sleeve end 86S (see FIG. 16C). At this point, the third sleeve body 86C is removed from the second mandrel body 144 and is formed into a fourth sleeve body 86D (see FIGS. 16D and 20F).

Figure 20F:
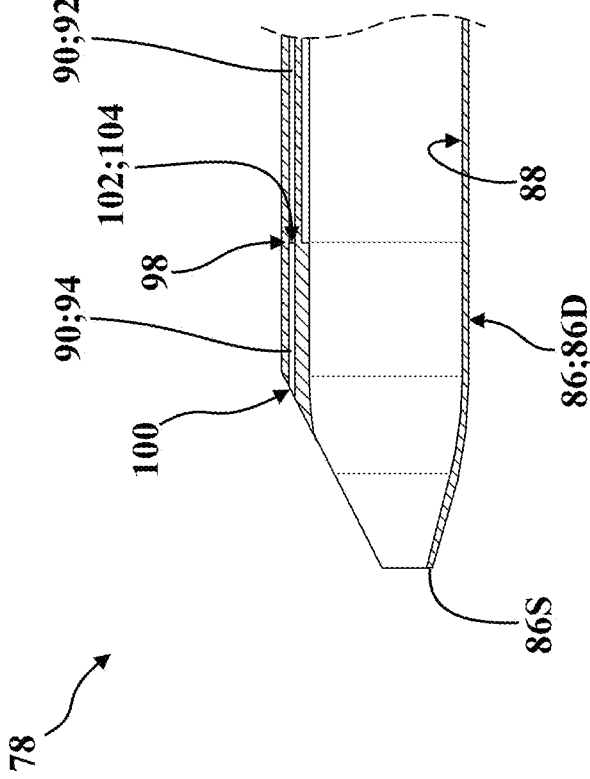
FIG. 20F is an enlarged, partial sectional view of the distal sleeve end of the sleeve body depicted in FIG. 16D.
Figure 21:
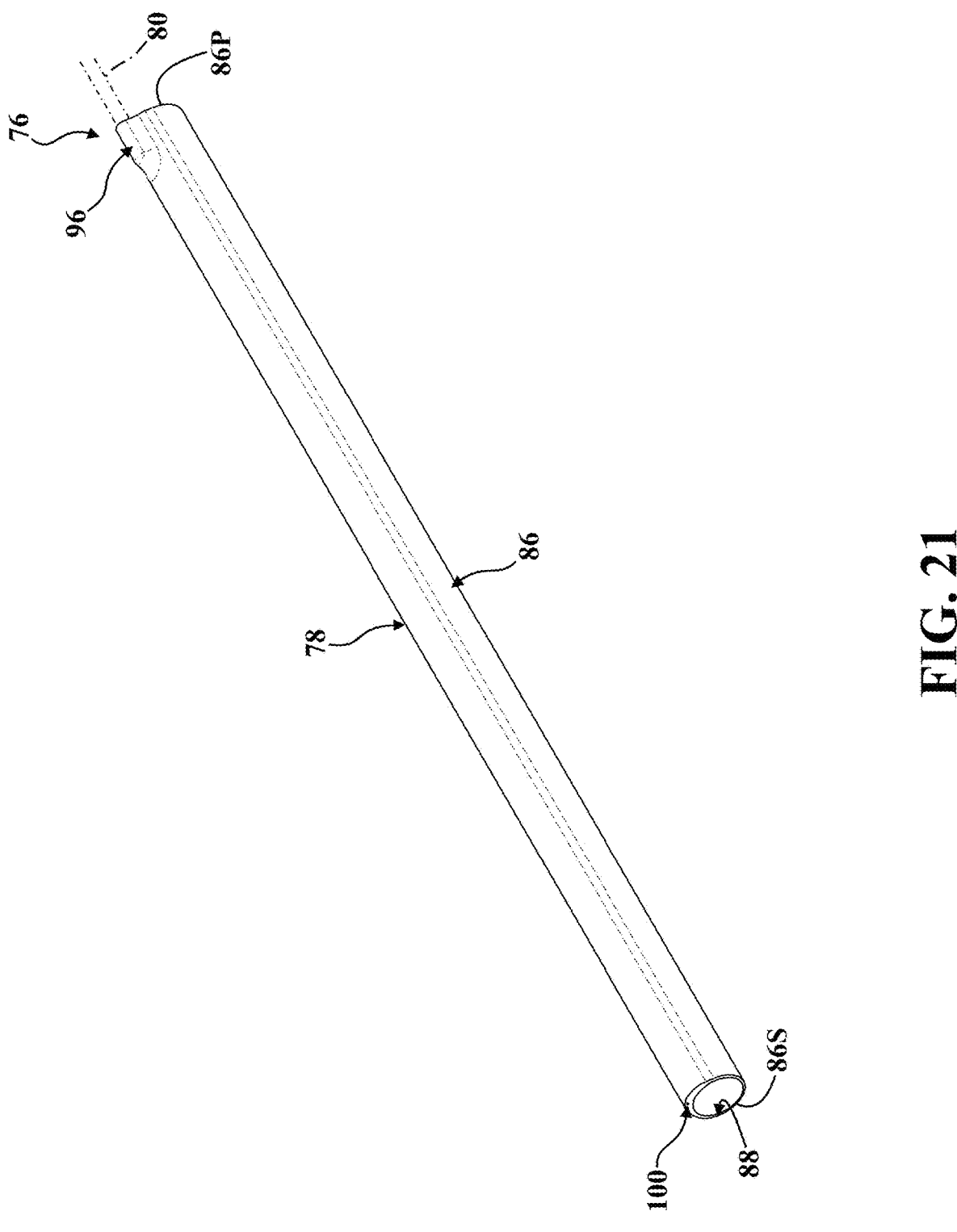
FIG. 21 is a perspective view of another embodiment of an irrigation sleeve of an irrigation sleeve assembly of a surgical system.

The fourth sleeve body 86D is formed by removing at least a portion of the reformed distal sleeve end 86S to define, expose, or otherwise reveal the lumen outlet 100 described above (compare FIG. 20E with FIG. 20F). To this end, the reformed distal sleeve end 86S can be chamfer cut (see FIG. 16D), skived (see FIG. 17) or punched (see FIG.

Figure 19:
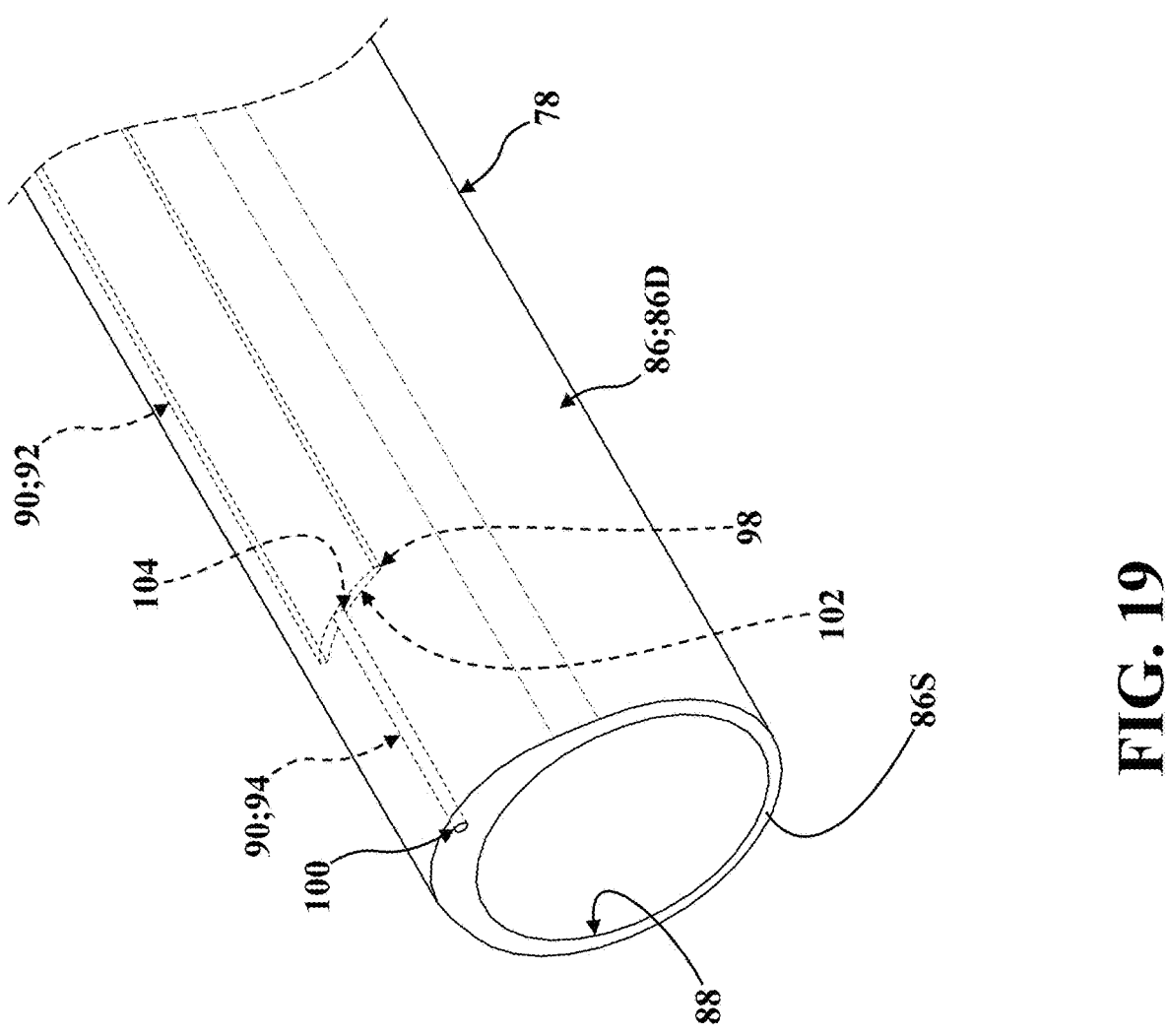
FIG. 19 is an enlarged, partial perspective view of a distal sleeve end of a sleeve body comprising first and second lumens, with the second lumen illustrated in phantom and shown comprising a proximal lumen region having a crescent-shaped profile and a distal lumen region having a cylindrical profile, and with the distal sleeve end of the sleeve body shown having a generally flat profile through which a transverse cut has been made to define a lumen outlet arranged at the distal sleeve end and disposed in fluid communication with the distal lumen region.

18) to expose the lumen outlet 100 so as to define the fourth sleeve body 86D. However, those having ordinary skill in the art will appreciate that the lumen outlet 100 can be exposed in other ways. Moreover, it will be appreciated that the irrigation sleeve 78 described herein can be manufactured in any suitable way consistent with the foregoing description. By way of non-limiting example, FIG. 19 depicts an embodiment of the sleeve body 86 which has been "flat cut" generally perpendicularly (or, "transversely" to expose the lumen outlet 100. Other configurations are contemplated.

Figure 29:
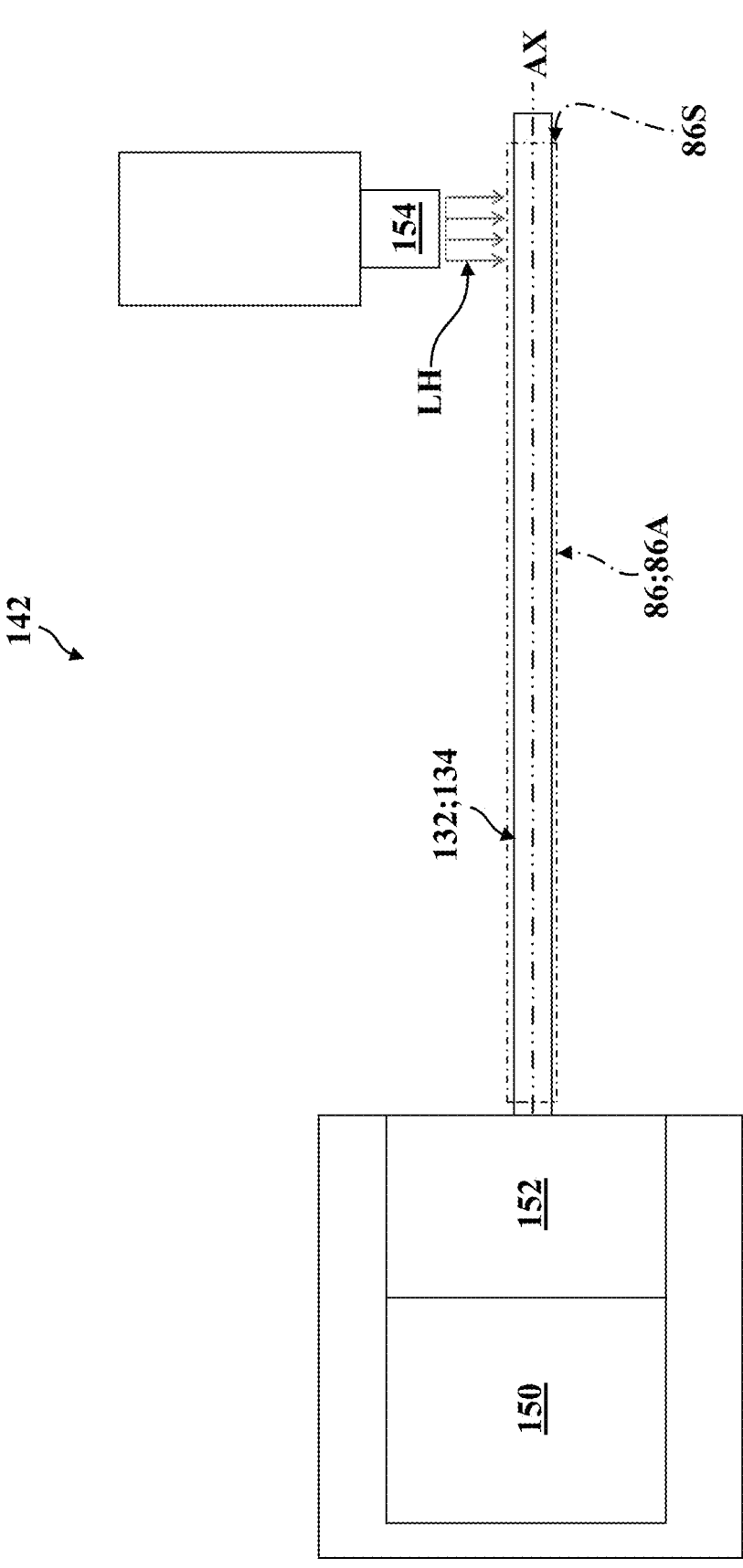
FIG. 29 is a schematic view of a manufacturing system for use in reforming sleeve bodies comprising first and second lumens to differentiate the second lumen into distal and proximal lumen regions, the manufacturing system shown having a first mandrel body supported for rotation about an axis.
Figure 30A:
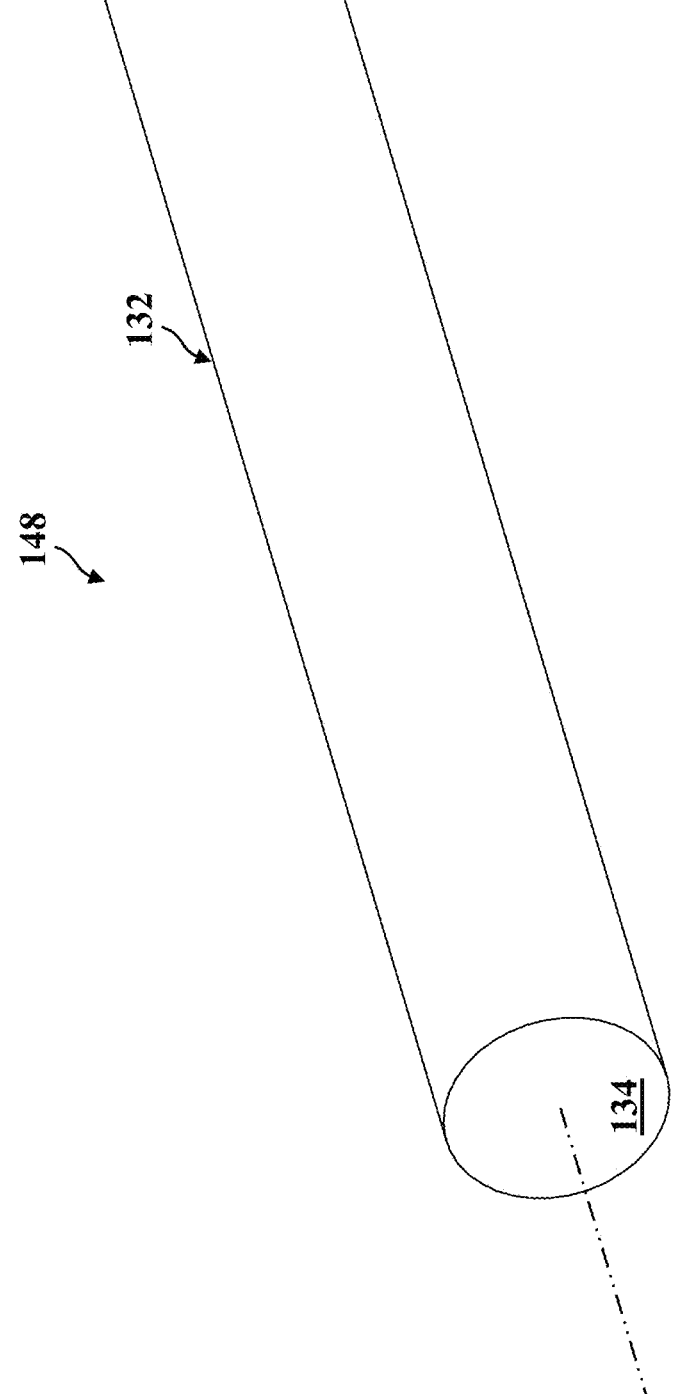
FIG. 30A is an enlarged, partial perspective view of the first mandrel body of the manufacturing system of FIG. 29.
Figure 30B:
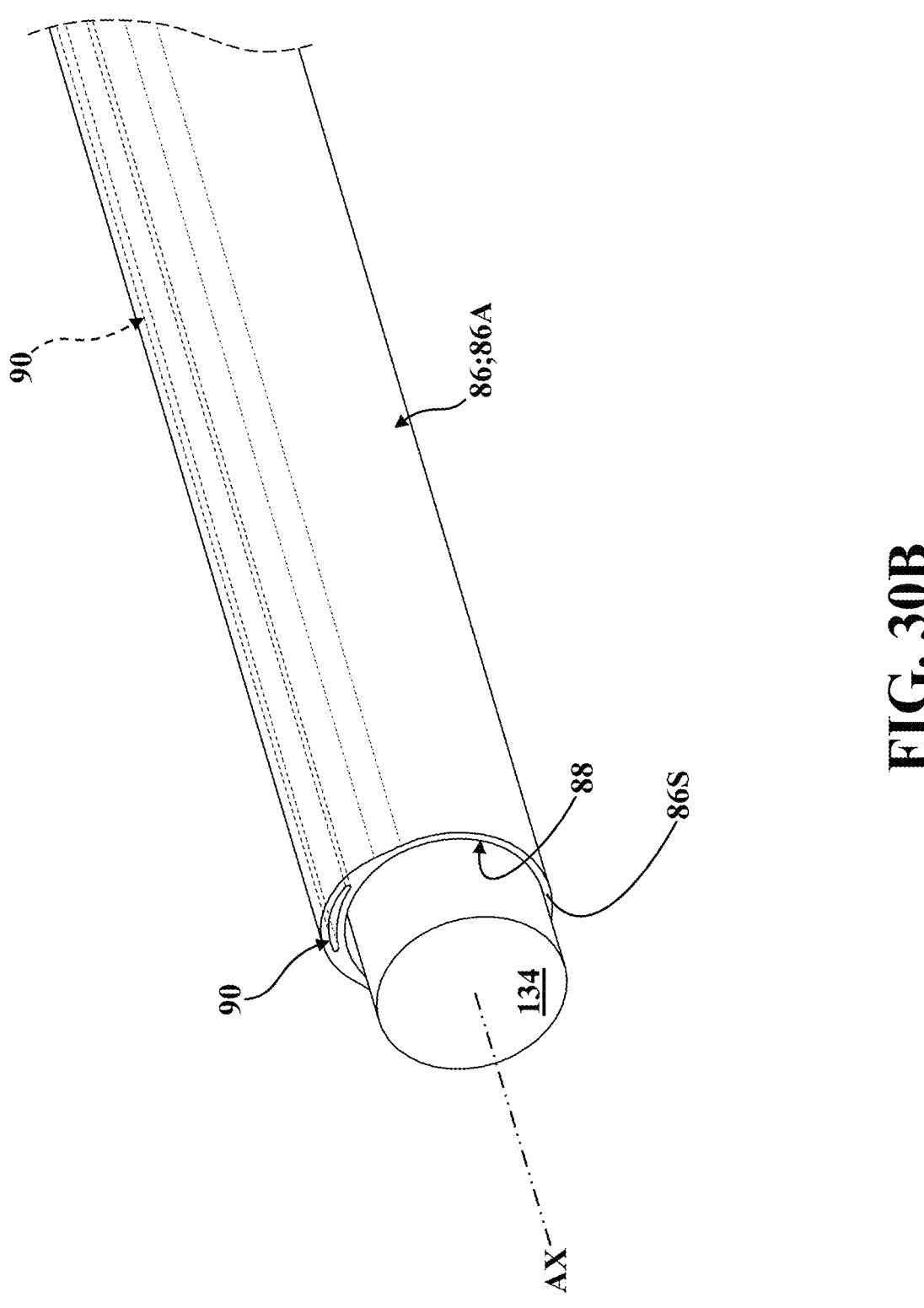
FIG. 30B is another enlarged, partial perspective view of the first mandrel body illustrated in FIG. 30A, further depicting a sleeve body comprising first and second lumens, and shown with the first mandrel body extending through the first lumen of the sleeve body, and with the second lumen illustrated in phantom and shown having a crescent-shaped profile.
Figure 30C:
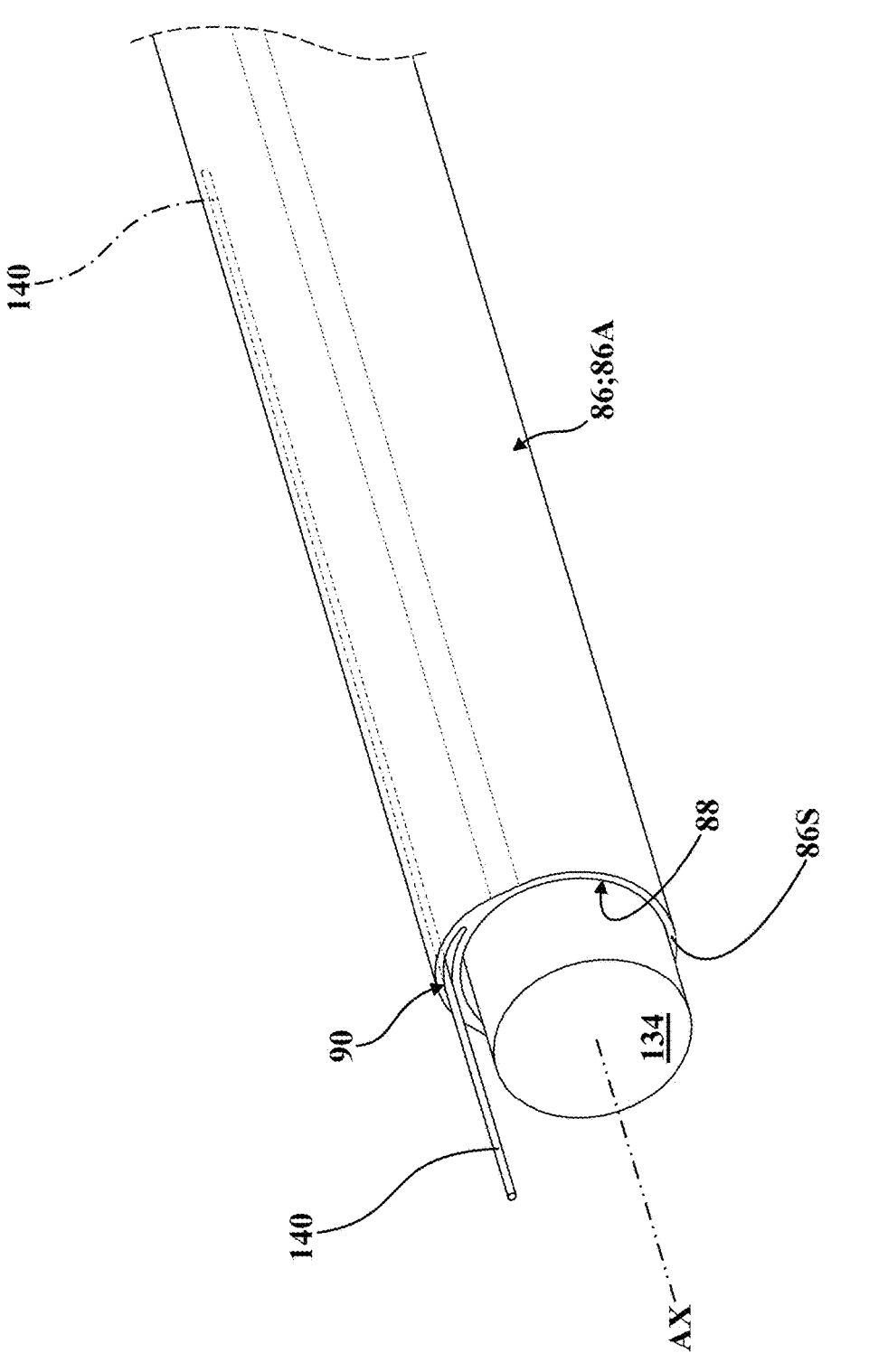
FIG. 30C is another enlarged, partial perspective view of the first mandrel body and the sleeve body illustrated in FIG. 30B, shown with a shaft positioned into the second lumen of the sleeve body.
Figure 30D:
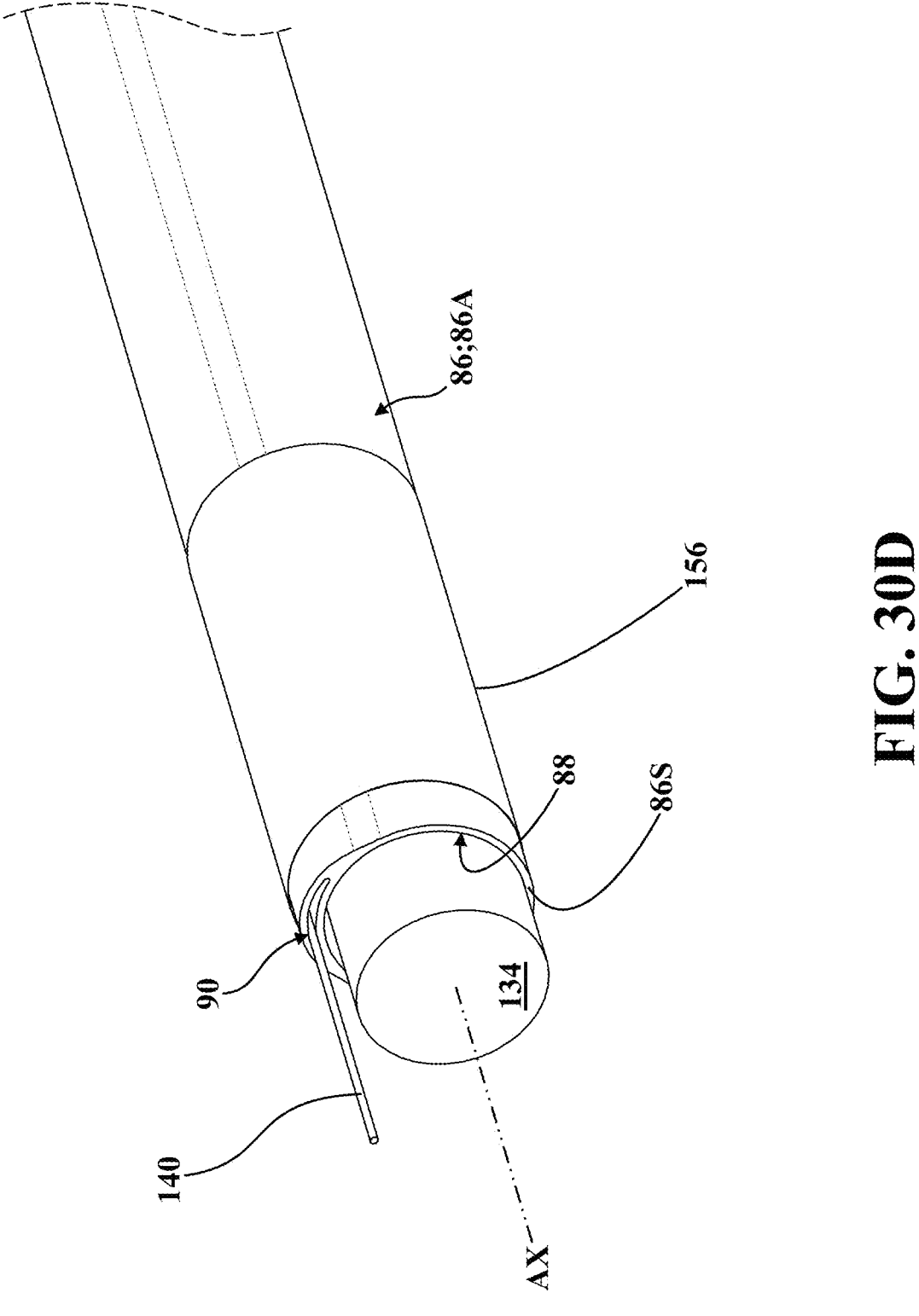
FIG. 30D is another enlarged, partial perspective view of the first mandrel body, the sleeve body, and the shaft illustrated in FIG. 30C, further depicting heat-shrink tubing disposed over a portion of the sleeve body adjacent to the distal sleeve end.
Figure 30E:
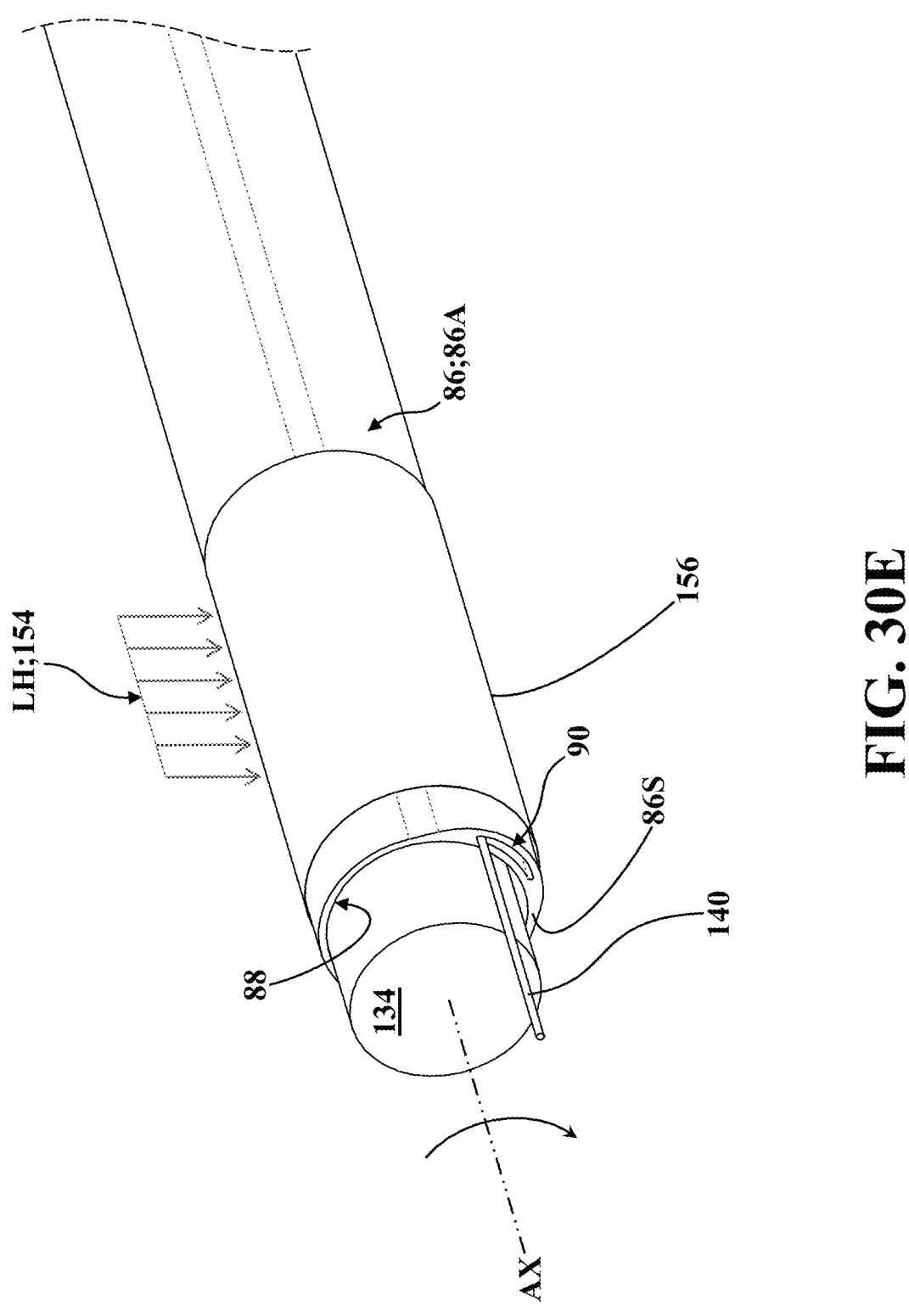
FIG. 30E is another enlarged, partial perspective view of the first mandrel body, the sleeve body, the shaft, and the heat-shrink tubing illustrated in FIG. 30D, shown rotating about the axis and being subjected to the application of localized heat.
Figure 30F:
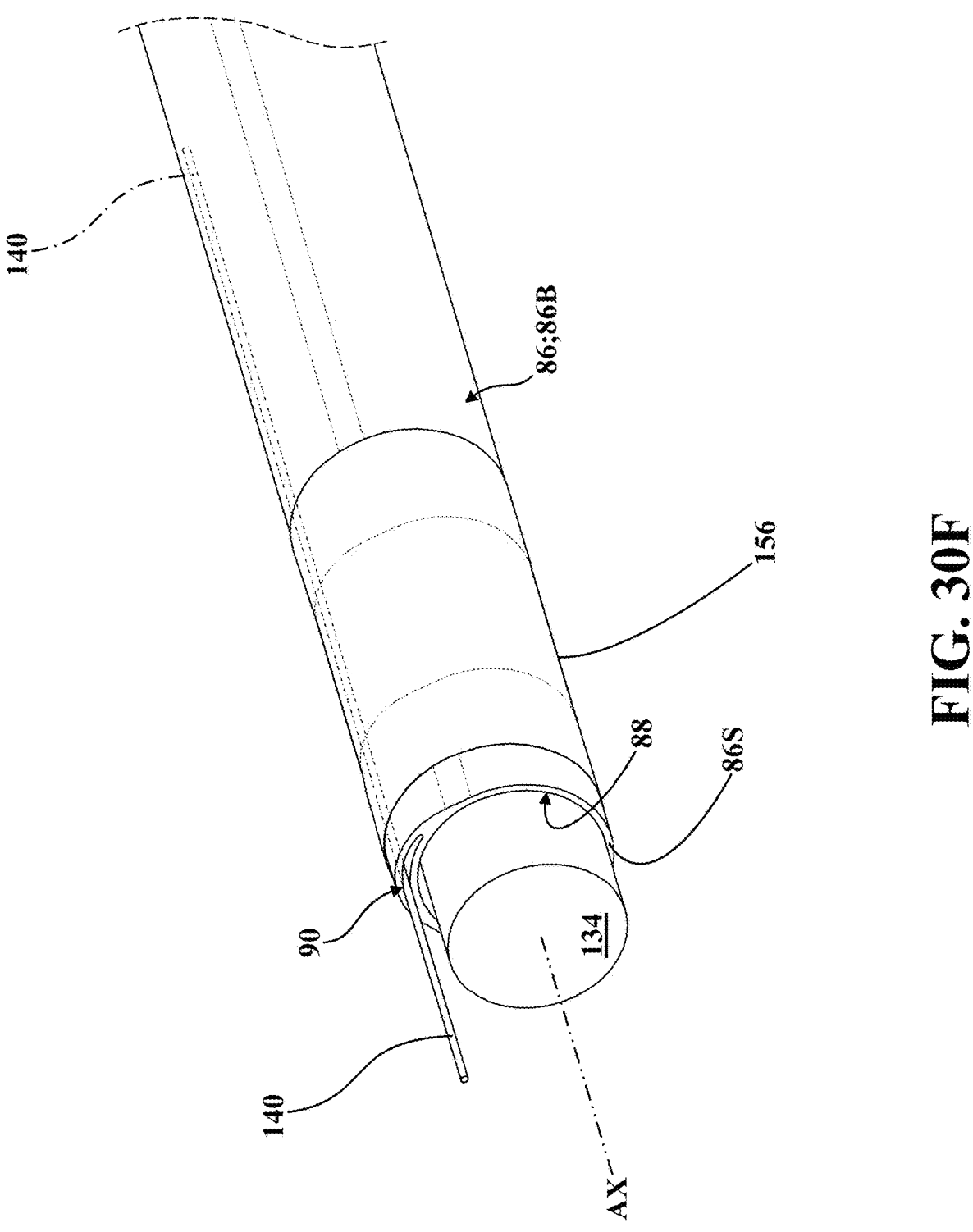
FIG. 30F is another enlarged, partial perspective view of the first mandrel body, the sleeve body, the shaft, and the heat-shrink tubing illustrated in FIGS. 30D-30E, shown with the heat-shrink tubing partially shrunk around the sleeve body in response to the application of localized heat.
Figure 30G:
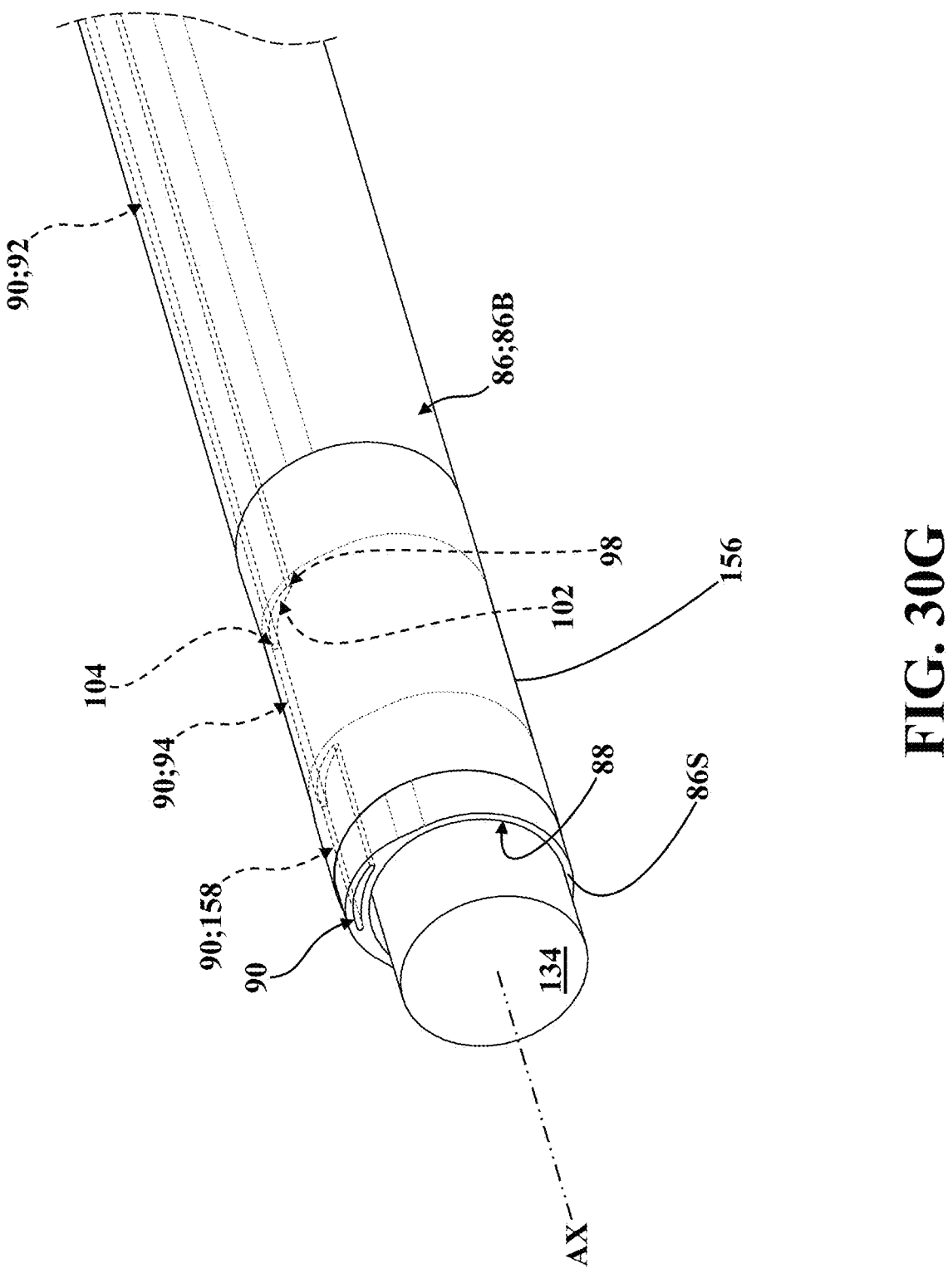
FIG. 30G is an enlarged, partial perspective view of the first mandrel body, the sleeve body, and the heat-shrink tubing of FIG. 30F, with the second lumen illustrated in phantom and shown comprising a scrap lumen region having a crescent-shaped profile, a proximal lumen region having a crescent-shaped profile, and a distal lumen region having a cylindrical profile
Figure 30H:
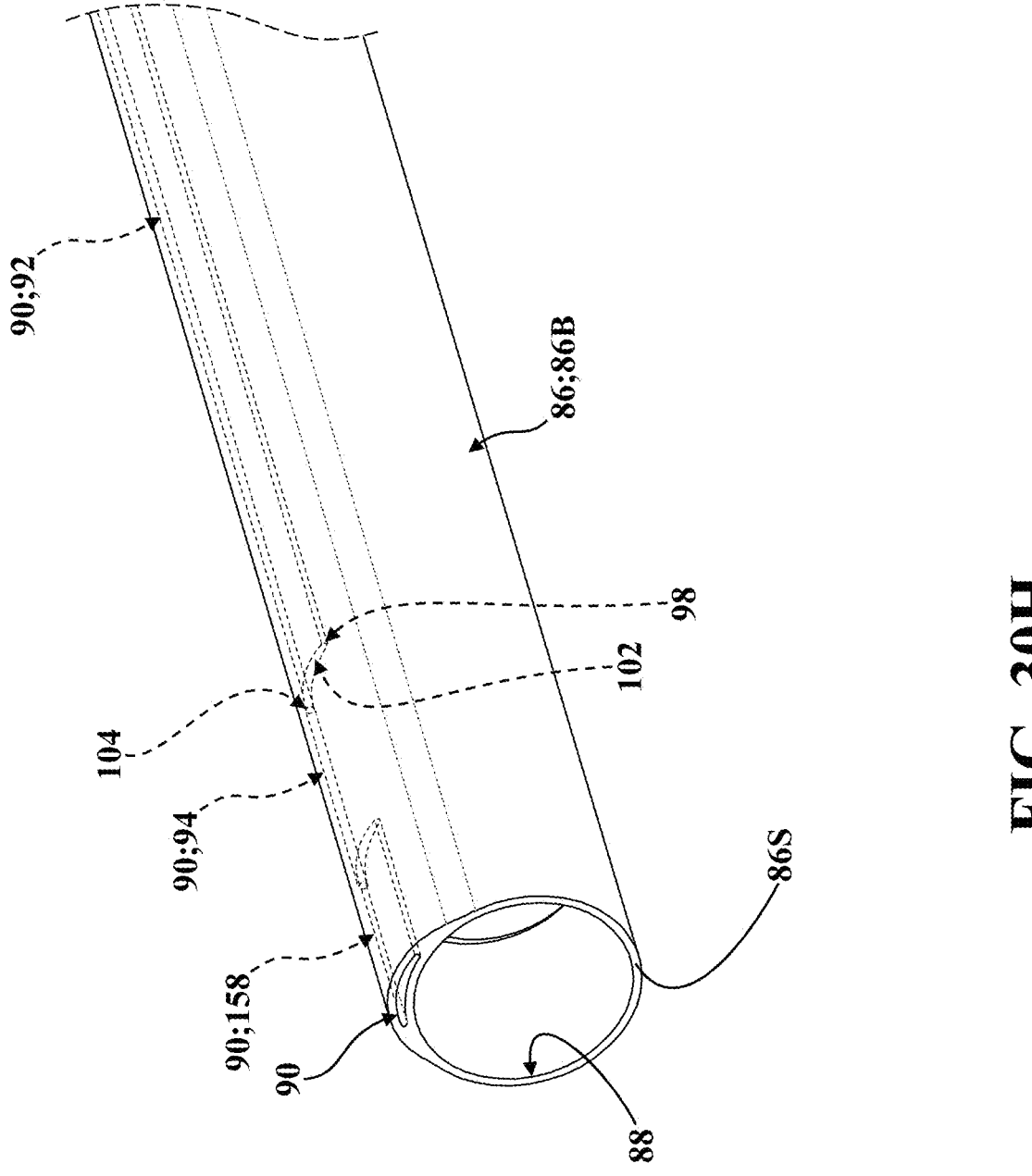
FIG. 30H is an enlarged, partial perspective view of the sleeve body of FIG. 30G, showing the cylindrical distal lumen region arranged between the crescent-shaped scrap and proximal lumen regions.
Figure 30I:
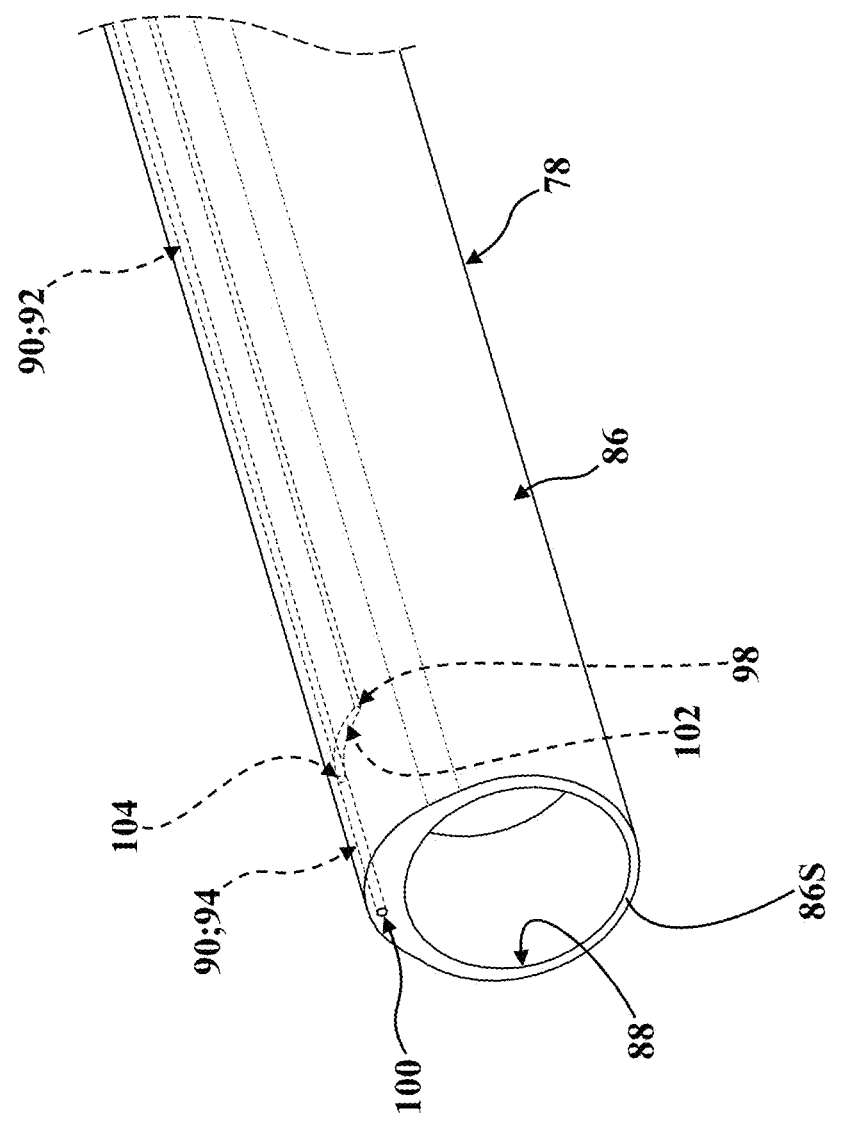
FIG. 30I is another enlarged, partial perspective view of the sleeve body of FIG. 30H, shown having a distal sleeve end with a generally flat profile defined by a transverse cut made through the sleeve body along the cylindrical distal lumen region to define a lumen outlet arranged at the distal sleeve end and disposed in fluid communication with the distal lumen region.

As noted above, the process of manufacturing the embodiment of the irrigation sleeve 78 illustrated in FIGS. 21-28 is disclosed in connection with FIGS. 29-30I.

Referring now to FIG. 29, a manufacturing system 148 is depicted schematically. The manufacturing system 148 generally comprises a driver 150, a gearset 152, and an energy applicator 154. The driver 150 is configured to selectively generate rotational torque which, in turn, is translated to the gearset 152 to rotate a cylindrical first mandrel body 134 about the axis AX. To this end, the driver 150 may be realized by an electric motor, and the gearset 152 may be a planetary gear reduction to adjust the rotational speed of the first mandrel body 134 about the axis. However, it will be appreciated that the driver 150 could be configured in a number of different ways sufficient to rotate the first mandrel body 134, with or without the use of a gearset 152. The energy applicator 154, likewise depicted schematically in FIG. 29, is configured to generate, direct, or otherwise apply localized heat LH, and may be realized as a laser heater, a heat gun, and the like.

Referring now to FIGS. 30A-30I, certain steps involved in the process of manufacturing the embodiment of the irrigation sleeve 78 depicted and described above in connection with FIGS. 21-28 are shown sequentially. In FIG. 30A, a portion of the generally cylindrical first mandrel body 134 is shown arranged for rotation about the axis AX, such as via torque selectively generated by the driver 150 (see FIG. 29).

In FIG. 30B, a portion of a first sleeve body 86A of the type described above in connection with FIG. 16A is shown. Here too, the first sleeve body 86A likewise extends between the distal sleeve end 86S and proximal sleeve end 86P (not shown), with the first and second lumens 88, 90 pre-formed in the first sleeve body 86A. At this step of manufacturing, and the second lumen 90 similarly has the crescent-shaped profile along the entire length of the first sleeve body, provided such as via an extrusion manufacturing process. The first sleeve body 86A is supported by the first mandrel body 134 by positioning the first mandrel body 134 within the first lumen 88 of the first sleeve body 86A.

In FIG. 30C, the shaft 140 is shown inserted into the second lumen 90 of the first sleeve body 86A, and is positioned adjacent to or otherwise in abutment with the first lumen corner surface 114. However, as noted above, because the shaft 140 effectively defines the distal lumen region 94 of the second lumen 90, it will be appreciated that the shaft 140 could be positioned within the second lumen 90 in other ways besides in abutment with the first lumen corner surface 114 of the second lumen 90.

In FIG. 30D, a section of heat-shrink tubing 156 is shown placed over the first sleeve body 86A. As noted above, heat-shrink tubing 156 allows for the application of hoop compression to the first sleeve body 86A in response to the application of localized heat LH, such as from the energy applicator 154 (see FIG. 29).

In FIG. 30E, the first mandrel body 134, the first sleeve body 86A, the shaft 140, and the heat-shrink tubing 156 are shown rotating generally concurrently about the axis AX (compare FIG. 30E with FIG. 30D), such as via torque generated by the driver 150 (see FIG. 30), while localized heat LH is applied adjacent to the heat-shrink tubing 156 to reform the material of the first sleeve body 86A around the first mandrel body 134 and the shaft 140. More specifically, the rotation about the axis AX and the application of localized heat LH causes the heat-shrink tubing 156 to "shrink" and apply hoop compression, which helps reform the first sleeve body 86A into a second sleeve body 86B in an efficient and relatively evenly-distributed fashion.

In FIG. 30F, the rotation about the axis AX and the application of localized heat LH have ceased, and the second sleeve body 86B is shown supported on the first mandrel body 134, with the shaft 140 still positioned within the second lumen 90, and with the heat-shrink tubing 156 partially "shrunk" around a portion of the second sleeve body 86B. In FIG. 30G, the shaft 140 has been removed from the second lumen 90, and the second lumen 90 has is shown as having been differentiated into the proximal lumen region 92 with the crescent-shaped profile, the distal lumen region 94 with the cylindrical profile defined by the shaft 140, and scrap lumen region 158. Here, the distal lumen region 94 effectively aligns with the portion of the "shrunk" heat-shrink tubing 156 that was exposed to localized heat LH, and is arranged longitudinally between the proximal lumen region 92 and the scrap lumen region 158.

In FIG. 30H, the second sleeve body 86B is shown having been removed from the first mandrel body 134 and with the heat-shrink tubing 156 removed. In FIG. 30I, the second sleeve body 86B has been cut transversely through the first lumen 88 and a portion of the reformed distal lumen region 94 of the second lumen 90 to define the distal sleeve end 86S and the lumen outlet 100 (compare FIG. 30I with FIG. 30H). The lumen outlet 100 is arranged at the distal sleeve end 86S in this embodiment, as noted above.

In this way, the embodiments of the irrigation sleeves 78 of the irrigation sleeve assembly 76 described above allow for consistent, reliable irrigation of surgical sites ST, under a number of different operating conditions. Specifically, those having ordinary skill in the art will appreciate that the irrigation sleeves 78 facilitate fluid projection next to and beyond the head 64 of the cutting accessory 52 when irrigation is desired (such as by activating the footswitch 48) and, at the same time, prevent excessive fluid from projecting out of the lumen outlet 100 and "splashing" against the shank 66 of the cutting accessory 52 when irrigation is ceased (such as by deactivating the footswitch 48). Moreover, it will be appreciated that the low-profile of the irrigation sleeve 78 affords significant advantages in connection with medical and/or surgical procedures where irrigation is desirable but the surgical site ST is small, difficult to access, and the like (e.g., when used in connection with trans-nasal approaches). Furthermore, those having ordinary skill in the art will appreciate that the irrigation sleeves 78 described herein can be used in connection with a number of different types of surgical tools 44, in particular those types of surgical tools 44 which are employed for use in confined surgical sites ST, and are adapted for use with a number of different types of conventional irrigation systems 42.

It will be further appreciated that the terms "include," "includes," and "including" have the same meaning as the terms "comprise," "comprises," and "comprising." Moreover, it will be appreciated that terms such as "first," "second," "third," and the like are used herein to differentiate certain structural features and components for the non-limiting, illustrative purposes of clarity and consistency.

Several configurations have been discussed in the foregoing description. However, the configurations discussed herein are not intended to be exhaustive or limit the invention to any particular form. The terminology which has been used is intended to be in the nature of words of description rather than of limitation. Many modifications and variations are possible in light of the above teachings and the invention may be practiced otherwise than as specifically described.

The invention is intended to be defined in the independent claims, with specific features laid out in the dependent claims, wherein the subject-matter of a claim dependent from one independent claim can also be implemented in connection with another independent claim.

The present disclosure also comprises the following clauses, with specific features laid out in dependent clauses, that may specifically be implemented as described in greater detail with reference to the configurations and drawings above.

Clauses

I. An irrigation sleeve for use with a surgical system comprising an irrigation source, a rotary instrument having a tube extending to a distal tube end, and a cutting accessory having a head and a shank extending from the head and adapted to be rotatably supported by the tube of the rotary instrument, said irrigation sleeve comprising: a sleeve body extending between a proximal sleeve end and a distal sleeve end; a first lumen formed in said sleeve body for receiving at least a portion of the tube of the rotary instrument with the head of the cutting accessory arranged adjacent to said distal sleeve end; and a second lumen formed in said sleeve body, spaced from said first lumen, and comprising a proximal lumen region and a distal lumen region, said proximal lumen region extending from a lumen inlet adapted for fluid communication with the irrigation source to a lumen transition, and said distal lumen region extending from said lumen transition to a lumen outlet arranged to direct fluid adjacent to the head of the cutting accessory, said proximal lumen region having a larger cross sectional area than said distal lumen region taken at said lumen transition.

II. The irrigation sleeve as set forth in clause I, wherein said first lumen has a cylindrical profile.

III. The irrigation sleeve as set forth in any one of clauses I-II, wherein said proximal lumen region of said second lumen has a crescent-shaped profile.

IV. The irrigation sleeve as set forth in any one of clauses I-III, wherein said distal lumen region of said second lumen has a profile different from said crescent-shaped profile of said proximal lumen region.

V. The irrigation sleeve as set forth in any one of clauses I-IV, wherein said distal lumen region of said second lumen has a cylindrical profile.

VI. The irrigation sleeve as set forth in any one of clauses I-V, wherein said lumen outlet is arranged between said lumen transition and said distal sleeve end.

VII. The irrigation sleeve as set forth in any one of clauses I-VI, wherein said lumen transition defines a transition surface with said distal lumen region extending in fluid communication between said lumen outlet and said transition surface.

VIII. The irrigation sleeve as set forth in any one of clauses I-VII, wherein a first distance is defined between said lumen outlet and said lumen transition; and wherein a second distance, larger than said first distance, is defined between said lumen transition and said lumen inlet.

IX. The irrigation sleeve as set forth in any one of clauses I-VIII wherein said first lumen is aligned about a first lumen path, and said second lumen is aligned about a second lumen path spaced from said first lumen path.

X. The irrigation sleeve as set forth in clause IX, wherein said first lumen path is linear.

XI. The irrigation sleeve as set forth in any one of clauses IX-X, wherein said second lumen path is radially spaced from said first lumen path.

XII. The irrigation sleeve as set forth in any one of clauses IX-XI, wherein said second lumen path is linear and is parallel to said first lumen path.

XIII. The irrigation sleeve as set forth in any one of clauses IX-XII, wherein said first lumen path is aligned with said second lumen path.

XIV. An irrigation sleeve for use with a surgical system comprising an irrigation source, a rotary instrument having a tube extending to a distal tube end, and a cutting accessory having a head and a shank extending from the head and adapted to be rotatably supported by the tube of the rotary instrument, said irrigation sleeve comprising: a sleeve body extending between a proximal sleeve end and a distal sleeve end; a first lumen formed in said sleeve body for receiving at least a portion of the tube of the rotary instrument with the head of the cutting accessory arranged adjacent to said distal sleeve end; and a second lumen formed in said sleeve body, spaced from said first lumen, and comprising a proximal lumen region and a distal lumen region, said proximal lumen region extending from a lumen inlet adapted for fluid communication with the irrigation source to a lumen transition, and said distal lumen region extending from said lumen transition to a lumen outlet arranged to direct fluid adjacent to the head of the cutting accessory, said proximal lumen region having a crescent-shaped profile and said distal lumen region having a profile different from said crescent-shaped profile of said proximal lumen region.

XV. The irrigation sleeve as set forth in clause XIV, wherein said first lumen has a cylindrical profile.

XVI. The irrigation sleeve as set forth in any one of clauses XIV-XV, wherein said distal lumen region of said second lumen has a cylindrical profile.

XVII. The irrigation sleeve as set forth in any one of clauses XIV-XVI, wherein said proximal lumen region of said second lumen has a larger cross sectional area than said distal lumen region taken at said lumen transition.

XVIII. The irrigation sleeve as set forth in any one of clauses XIV-XVII, wherein said lumen outlet is arranged between said lumen transition and said distal sleeve end.

XIX. The irrigation sleeve as set forth in any one of clauses XIV-XVIII, wherein said lumen transition defines a transition surface with said distal lumen region extending in fluid communication between said lumen outlet and said transition surface.

XX. The irrigation sleeve as set forth in any one of clauses XIV-XIX, wherein a first distance is defined between said lumen outlet and said lumen transition; and wherein a second distance, larger than said first distance, is defined between said lumen transition and said lumen inlet.

XXI. The irrigation sleeve as set forth in any one of clauses XIV-XX, wherein said first lumen is aligned about a first lumen path, and said second lumen is aligned about a second lumen path spaced from said first lumen path.

XXII. The irrigation sleeve as set forth in clause XXI, wherein said first lumen path is linear.

XXIII. The irrigation sleeve as set forth in any one of clauses XXI-XXII, wherein said second lumen path is radially spaced from said first lumen path.

XXIV. The irrigation sleeve as set forth in any one of clauses XXI-XXIII, wherein said second lumen path is linear and is parallel to said first lumen path.

XXV. The irrigation sleeve as set forth in any one of clauses XXI-XXIV, wherein said first lumen path is aligned with said second lumen path.

XXVI. A method of manufacturing an irrigation sleeve, said method comprising; forming a sleeve body between a proximal sleeve end and a distal sleeve end, the sleeve body having a first lumen and a second lumen spaced from the first lumen, the second lumen having a crescent-shaped profile; positioning a shaft into the second lumen at the distal sleeve end; reforming the sleeve body around the shaft adjacent to the distal sleeve end to differentiate the second lumen into a distal lumen region having a cylindrical profile defined by the shaft and a proximal lumen region having the crescent-shaped profile.

XXVII. The method as set forth in clause XXVI, further comprising: providing a first mandrel assembly having an insertion guide shaped to support the shaft; supporting the sleeve body with the first mandrel assembly; and positioning the shaft into the insertion guide of the first mandrel assembly.

XXVIII. The method as set forth in any one of clauses XXVI-XXVII, further comprising: removing the shaft from the distal lumen region of the second lumen.

XXIX. The method as set forth in any one of clauses XXVI-XXVIII, further comprising: providing a second mandrel assembly having a conical region; supporting the sleeve body with the second mandrel assembly; and reforming at least a portion of the sleeve body adjacent to the distal sleeve end around the conical region of the second mandrel assembly.

XXX. The method as set forth in clause XXIX, further comprising: removing at least a portion of the sleeve body adjacent to the distal sleeve end to define a lumen outlet in fluid communication with the distal lumen region.

XXXI. A method of irrigating bone at a surgical site, said method comprising: providing a rotary instrument, a cutting accessory having a bur head, and an irrigation sleeve having a sleeve body extending between a proximal sleeve end and a distal sleeve end with a first lumen formed in the sleeve body and with a second lumen formed in the sleeve body spaced from the first lumen; positioning the rotary instrument in the first lumen of the irrigation sleeve such that the bur head of the cutting accessory extends beyond the distal sleeve end; engaging bone with the bur head of the cutting accessory; and directing fluid through the second lumen of the irrigation sleeve such that fluid exiting the second lumen adjacent to the distal sleeve end projects next to and beyond the bur head towards bone.

What is claimed is:

1. A method of manufacturing an irrigation sleeve, said method comprising:

forming a sleeve body between a proximal sleeve end and a distal sleeve end, the sleeve body having a first lumen and a second lumen spaced from the first lumen, the second lumen having a generally crescent-shaped profile;

positioning a shaft into the second lumen at the distal sleeve end; and reforming the sleeve body around the shaft adjacent to the distal sleeve end to differentiate the second lumen into a distal lumen region having a cylindrical profile defined by the shaft and a proximal lumen region having the crescent-shaped profile.

2. The method as set forth in claim 1, further comprising:

providing a first mandrel assembly having an insertion guide shaped to support the shaft;

supporting the sleeve body with the first mandrel assembly; and positioning the shaft into the insertion guide of the first mandrel assembly.

3. The method as set forth in claim 1, further comprising removing the shaft from the distal lumen region of the second lumen.

4. The method as set forth in claim 1, further comprising:

providing a second mandrel assembly having a conical region;

supporting the sleeve body with the second mandrel assembly; and reforming at least a portion of the sleeve body adjacent to the distal sleeve end around the conical region of the second mandrel assembly.

5. The method as set forth in claim 4, further comprising removing at least a portion of the sleeve body adjacent to the distal sleeve end to define a lumen outlet in fluid communication with the distal lumen region.

6. The method as set forth in claim 1, wherein the proximal lumen region of the second lumen extends from a lumen inlet adapted for fluid communication with an irrigation source to a lumen transition, and the distal lumen region of the second lumen extends from the lumen transition to a lumen outlet arranged to direct fluid adjacent to a head of a cutting accessory, the proximal lumen region having a larger cross-sectional area than the distal lumen region taken at the lumen transition.

7. The method as set forth in claim 6, wherein the lumen transition defines a transition surface, and wherein the distal lumen region comprises a transition inlet defined in the transition surface such that the distal lumen region extends in fluid communication between the transition inlet and the lumen outlet.

8. The method as set forth in claim 7, wherein the lumen outlet is arranged between the lumen transition and the distal sleeve end.

9. The method as set forth in claim 7, wherein the lumen outlet is arranged at the distal sleeve end.

10. The method as set forth in claim 7, wherein the transition surface has an outer periphery defined at least partially by the generally crescent-shaped profile of the proximal lumen region.

11. The method as set forth in claim 7, wherein the proximal lumen region of the second lumen has a profile comprising a first lumen corner surface and a second lumen corner surface; and wherein the transition surface has a profile comprising a first transition corner surface arranged generally coincident with the first lumen corner surface of the proximal lumen region.

12. A method of manufacturing an irrigation sleeve, said method comprising:

forming a sleeve body between a proximal sleeve end and a distal sleeve end, the sleeve body having a first lumen and a second lumen spaced from the first lumen;

positioning a shaft into the second lumen at the distal sleeve end; and reforming the sleeve body around the shaft adjacent to the distal sleeve end to differentiate the second lumen into a distal lumen region having a cylindrical profile defined by the shaft and a proximal lumen region;

wherein the second lumen is spaced out of fluid communication with the first lumen.

13. The method as set forth in claim 12, further comprising:

providing a first mandrel assembly having an insertion guide shaped to support the shaft;

supporting the sleeve body with the first mandrel assembly; and positioning the shaft into the insertion guide of the first mandrel assembly.

14. The method as set forth in claim 12, further comprising removing the shaft from the distal lumen region of the second lumen.

15. The method as set forth in claim 12, further comprising:

providing a second mandrel assembly having a conical region;

supporting the sleeve body with the second mandrel assembly; and reforming at least a portion of the sleeve body adjacent to the distal sleeve end around the conical region of the second mandrel assembly.

16. The method as set forth in claim 15, further comprising removing at least a portion of the sleeve body adjacent to the distal sleeve end to define a lumen outlet in fluid communication with the distal lumen region.

17. The method as set forth in claim 12, wherein the proximal lumen region of the second lumen extends from a lumen inlet adapted for fluid communication with an irrigation source to a lumen transition, and the distal lumen region of the second lumen extends from the lumen transition to a lumen outlet arranged to direct fluid adjacent to a head of a cutting accessory, the proximal lumen region having a larger cross-sectional area than the distal lumen region taken at the lumen transition.

18. The method as set forth in claim 17, wherein the lumen transition defines a transition surface, and wherein the distal lumen region comprises a transition inlet defined in the transition surface such that the distal lumen region extends in fluid communication between the transition inlet and the lumen outlet.

19. The method as set forth in claim 17, wherein the lumen outlet is arranged between the lumen transition and the distal sleeve end.

20. The method as set forth in claim 18, wherein the transition surface has an outer periphery defined at least partially by a generally crescent-shaped profile of the proximal lumen region, and wherein the proximal lumen region of the second lumen has a profile comprising a first lumen corner surface and a second lumen corner surface; and wherein the transition surface has a profile comprising a first transition corner surface arranged generally coincident with the first lumen corner surface of the proximal lumen region.

* * * * *